US009066919B2

(12) United States Patent
Brown

(10) Patent No.: US 9,066,919 B2
(45) Date of Patent: *Jun. 30, 2015

(54) HYALURONAN AS A CHEMO-SENSITIZER IN THE TREATMENT OF CANCER

(75) Inventor: Tracey J. Brown, Flemington (AU)

(73) Assignee: Alchemia Oncology Pty Limited, Eight Mile Plains, Queensland (AU)

( * ) Notice: Subject to any disclaimer, the term of this patent is extended or adjusted under 35 U.S.C. 154(b) by 2328 days.

This patent is subject to a terminal disclaimer.

(21) Appl. No.: 11/198,663

(22) Filed: Aug. 5, 2005

(65) Prior Publication Data
US 2006/0178342 A1 Aug. 10, 2006

Related U.S. Application Data

(63) Continuation-in-part of application No. 10/088,774, filed as application No. PCT/AU01/00849 on Jul. 13, 2001, now abandoned.

(30) Foreign Application Priority Data

Jul. 14, 2000 (AU) ..................................... PQ 8795

(51) Int. Cl.
A61K 47/00 (2006.01)
A61K 9/00 (2006.01)
A61K 31/337 (2006.01)
A61K 31/4745 (2006.01)
A61K 31/525 (2006.01)
A61K 31/704 (2006.01)
A61K 31/7048 (2006.01)
A61K 31/728 (2006.01)
A61K 45/06 (2006.01)
A61K 47/36 (2006.01)

(52) U.S. Cl.
CPC ............ A61K 31/337 (2013.01); A61K 9/0014 (2013.01); A61K 9/0019 (2013.01); A61K 31/4745 (2013.01); A61K 31/525 (2013.01); A61K 31/704 (2013.01); A61K 31/7048 (2013.01); A61K 31/728 (2013.01); A61K 45/06 (2013.01); A61K 47/36 (2013.01)

(58) Field of Classification Search
None
See application file for complete search history.

(56) References Cited

U.S. PATENT DOCUMENTS

| 4,141,973 A | 2/1979 | Balazs |
| 4,160,452 A | 7/1979 | Theeuwes |
| 4,256,108 A | 3/1981 | Theeuwes |
| 4,265,874 A | 5/1981 | Bonsen et al. |
| 4,522,811 A | 6/1985 | Eppstein et al. |
| 4,665,107 A | 5/1987 | Micale |
| 4,736,024 A | 4/1988 | Della Valle et al. |
| 4,851,521 A | 7/1989 | della Valle et al. |
| 4,965,353 A | 10/1990 | della Valle et al. |
| 5,095,037 A | 3/1992 | Iwamitsu et al. |
| 5,128,450 A | 7/1992 | Urdal et al. |
| 5,202,431 A | 4/1993 | della Valle et al. |
| 5,208,020 A | 5/1993 | Chari et al. |
| 5,284,656 A | 2/1994 | Platz et al. |
| 5,416,071 A | 5/1995 | Igari et al. |
| 5,442,053 A | 8/1995 | della Valle et al. |
| 5,475,092 A | 12/1995 | Chari et al. |
| 5,585,499 A | 12/1996 | Chari et al. |
| 5,662,895 A | 9/1997 | Welte et al. |
| 5,676,964 A | 10/1997 | della Valle et al. |
| 5,733,891 A | 3/1998 | Akima et al. |
| 5,744,155 A | 4/1998 | Friedman et al. |
| 5,756,475 A | 5/1998 | Inomata et al. |
| 5,756,537 A | 5/1998 | Gill |
| 5,776,925 A | 7/1998 | Young et al. |
| 5,827,834 A | 10/1998 | Falk et al. |
| 5,830,882 A | 11/1998 | Falk et al. |
| 5,840,673 A | 11/1998 | Buckbinder et al. |
| 5,846,545 A | 12/1998 | Chari et al. |
| 5,847,002 A | 12/1998 | Willoughby et al. |
| 5,852,002 A | 12/1998 | Falk et al. |
| 5,968,972 A | 10/1999 | Broder et al. |
| 5,977,088 A | 11/1999 | Harper et al. |
| 5,985,850 A | 11/1999 | Falk et al. |
| 5,985,851 A | 11/1999 | Falk et al. |
| 6,027,741 A | 2/2000 | Cialdi et al. |
| 6,069,135 A * | 5/2000 | Falk et al. ........................ 514/54 |
| 6,087,350 A | 7/2000 | Johnson et al. |
| 6,214,860 B1 | 4/2001 | Sola et al. |
| 6,232,301 B1 | 5/2001 | Takahashi et al. |
| 6,242,457 B1 * | 6/2001 | Penco et al. .................. 514/283 |
| 6,299,900 B1 | 10/2001 | Reed et al. |
| 6,475,795 B1 | 11/2002 | Turley et al. |
| 6,552,184 B1 | 4/2003 | Pallado et al. |
| 6,579,978 B1 | 6/2003 | Renier et al. |
| 6,620,927 B2 | 9/2003 | Bulpitt et al. |
| 6,831,172 B1 | 12/2004 | Barbucci et al. |
| 7,420,033 B2 | 9/2008 | Varadhachary et al. |
| 8,287,894 B2 * | 10/2012 | Brown et al. ................. 424/422 |
| 8,388,993 B2 | 3/2013 | Brown |
| 8,623,354 B2 | 1/2014 | Brown et al. |
| 8,741,970 B2 * | 6/2014 | Brown .......................... 514/777 |
| 2002/0015724 A1 * | 2/2002 | Yang et al. ................... 424/443 |
| 2003/0087877 A1 | 5/2003 | Calias et al. |
| 2003/0180382 A1 | 9/2003 | Brown et al. |
| 2005/0042303 A1 | 2/2005 | Brown et al. |
| 2005/0267069 A1 | 12/2005 | Brown et al. |

(Continued)

FOREIGN PATENT DOCUMENTS

CA 612307 A 1/1961
CA 1227427 A1 9/1987

(Continued)

OTHER PUBLICATIONS

Sakurai et al. (Japanese Kokai Patent Document No. 61000017, Sho 61[1986]-17, English translation provided).*

(Continued)

Primary Examiner — Anna Pagonakis
(74) Attorney, Agent, or Firm — Morrison & Foerster LLP

(57) ABSTRACT

This application provides methods and compositions for the treatment of cancer. The application provides compositions including hyaluronic acid and a chemotherapeutic agent such as irinotecan that are useful in the treatment of cancer.

23 Claims, 23 Drawing Sheets

(56) References Cited

U.S. PATENT DOCUMENTS

| | | | |
|---|---|---|---|
| 2006/0263395 A1 | 11/2006 | Brown et al. | |
| 2007/0148734 A1 | 6/2007 | Chaudhuri et al. | |
| 2008/0063727 A1 | 3/2008 | Kim et al. | |
| 2009/0054537 A1 | 2/2009 | Brown | |
| 2009/0220497 A1 | 9/2009 | Brown et al. | |
| 2009/0306012 A1 | 12/2009 | Brown et al. | |
| 2013/0197103 A1 | 8/2013 | Brown | |

FOREIGN PATENT DOCUMENTS

| | | | |
|---|---|---|---|
| CA | 2089621 A1 | 8/1994 | |
| CA | 2122519 | 10/1995 | |
| CA | 2208924 A | 1/1999 | |
| CA | 2370003 A1 | 7/2000 | |
| CA | 2387058 A1 | 4/2001 | |
| CA | 2387058 C | 4/2001 | |
| EP | 0 138 572 A2 | 4/1985 | |
| EP | 0 138 572 A3 | 4/1985 | |
| EP | 0 138 572 B1 | 4/1985 | |
| EP | 0 216 453 A2 | 4/1987 | |
| EP | 0 216 453 A3 | 4/1987 | |
| EP | 0 216 453 B1 | 4/1987 | |
| EP | 0 265 116 B1 | 4/1988 | |
| EP | 0 341 745 A1 | 11/1989 | |
| EP | 0 341 745 B1 | 11/1989 | |
| EP | 0 433 817 B1 | 6/1991 | |
| EP | 0626863 A | 12/1994 | |
| EP | 1 598 371 A1 | 11/2005 | |
| JP | 61000017 | 1/1986 | |
| JP | 61-91986 U | 6/1986 | |
| JP | 4-504579 A | 8/1992 | |
| JP | 2002-534484 A | 10/2002 | |
| JP | 2003-518510 A | 6/2003 | |
| WO | WO-91/04058 A2 | 4/1991 | |
| WO | WO-93/16733 A1 | 9/1993 | |
| WO | WO-94/15640 A1 | 7/1994 | |
| WO | WO-94/23725 A1 | 10/1994 | |
| WO | WO-95/30423 A2 | 11/1995 | |
| WO | WO-95/30423 A3 | 11/1995 | |
| WO | WO-95/30439 A2 | 11/1995 | |
| WO | WO-95/30439 A3 | 11/1995 | |
| WO | WO-96/06622 A1 | 3/1996 | |
| WO | WO-97/20564 A1 | 6/1997 | |
| WO | WO 97/40841 A1 | 11/1997 | |
| WO | WO-98/17320 A1 | 4/1998 | |
| WO | WO-98/23648 A1 | 6/1998 | |
| WO | WO-99/02151 A1 | 1/1999 | |
| WO | WO-00/20642 A1 | 4/2000 | |
| WO | WO-00/41730 A1 | 7/2000 | |
| WO | WO-01/36656 A2 | 5/2001 | |
| WO | WO-01/47561 A1 | 7/2001 | |
| WO | WO-02/05852 A1 | 1/2002 | |
| WO | WO-02/090390 A1 | 11/2002 | |
| WO | WO-03/018062 A1 | 3/2003 | |
| WO | WO-2004/076491 A1 | 9/2004 | |
| WO | WO-2006/107124 A1 | 10/2006 | |
| WO | WO-2007/012133 A1 | 2/2007 | |
| WO | WO-2007/028196 A1 | 3/2007 | |

OTHER PUBLICATIONS

Taguchi et al. An early phase II study of CPT-11 (irinotecan hydrochloride) in patients with advanced breast cancer. Gan To Kagaku Ryoho. Jan. 1994; 21(1): 83-90.*

Bucci et al. Will the real hyaluronan please stand up.? Journal of Applied Nutrition, vol. 54, No. 1, 2004.*

Avis, K.E. (1975). "Parenteral Preparations," Chapter 84 in *Remington's Pharmaceutical Sciences*, 15$^{th}$ Edition, Easton: Mack Publishing Company, pp. 1461-1487.

Bernatchez, S.F. et al. (1994). "Sodium Hyaluronate as a Vehicle for an Improved Tolerance of 5-Fluorouracil Administered Subconjunctivally to Rabbits," *International Journal of Pharmaceutics* 106:161-166.

Canadian Office Action mailed Apr. 15, 2009, for CA Application No. 2,458,856, two pages.

Deardorff, D.L. (1975). "Isotonic Solutions," Chapter 79 in *Remington's Pharmaceutical Sciences*, 15$^{th}$ Edition, Easton: Mack Publishing Company, pp. 1405-1412.

European Search Report mailed Sep. 26, 2005, for EP Application No. 01951219.3, four pages.

Final Office Action mailed Oct. 30, 2008, for U.S. Appl. No. 09/889,203, filed Mar. 13, 2002, 13 pages.

Final Office Action mailed May 11, 2009, for U.S. Appl. No. 11/191,407, filed Jul. 27, 2005, 12 pages.

International Search Report dated Jul. 22, 1994, for PCT Application No. PCT/CA94/00207, filed Apr. 15, 1994, three pages.

International Search Report mailed Apr. 14, 2000, for PCT Application No. PCT/AU00/00004, filed Jan. 6, 2000, six pages.

International Search Report mailed Aug. 22, 2001, for PCT Application No. PCT/AU01/00849, filed Jul. 13, 2001, eight pages.

International Search Report mailed Oct. 14, 2002, for PCT Application No. PCT/AU02/01160, filed Aug. 27, 2002, three pages.

International Search Report mailed Sep. 22, 2006, for PCT Application No. PCT/AU2006/001059, filed Jul. 27, 2006, eight pages.

International Search Report mailed Oct. 17, 2006, for PCT Application No. PCT/AU2006/001293, filed Sep. 4, 2006, three pages.

Izawa, O.N. et al. (1992). "Hyaluronic Acid Derivative Synthesis and Properties (II)—Synthesis of Hyaluronic Acid Derivative with Thymine 5FU," *41$^{st}$ Society of Polymer Science Japan Conference Proceedings, Polymer Preprints*, Japan 42(3):479. (with English translation, eight pages.).

Japanese Office Action mailed Jul. 7, 2009, for JP Application No. 2003-522577, with English translation, five pages.

Klein, E.S. et al. (1994). "Effects of Hyaluronic Acid on Experimental Tumor Uptake of 5-Flurouracil," *Reg. Cancer Treat.* 7:163-164.

Langer, R. (Sep. 28, 1990). "New Methods of Drug Delivery," *Science* 249:1527-1533.

Luo, Y. et al. (1999, e-pub. Jul. 27, 1999). "Synthesis and Selective Cytotoxicity of Hyaluronic Acid-Antitumor Bioconjugate," *Bioconjugate Chemistry* 10:755-763.

Maucher, A. et al. (1994). "Antitumor Activity of Coumarin and 7-Hydroxycoumarin Against 7,12-dimethylbenz[a]anthracene-Induced Rat Mammary Carcinomas," *J. Cancer Res. Clin. Oncol.* 120:502-504.

Non-Final Office Action mailed May 14, 2009, for U.S. Appl. No. 11/415,612, filed May 1, 2006, four pages.

O'Neil, M.J. et al. eds. (2001). Definition of Irinotecan, Entry 5108, The Merck Index, Thirteenth Edition, Merck & Co., Inc.: Whitehouse Station, NJ, p. 915.

Ouchi, T. et al. (1991). "Design of Polysaccharide-5-Fluorouracil Conjugates Exhibiting Antitumour Activities," Chapter 8 *In American Chemical Society Symposium Series*, 469(Polymeric Drugs and Drug Delivery Systems):71-83.

Reynolds, J.E.F. ed. (1993). *Martindale: The Extra Pharmacopoeia*, 30$^{th}$ Edition, The Pharmaceutical Press: London, England, pp. 480-482.

Rivory, L.P. et al. (1996). "Conversion of Irinotecan (CPT-11) to Its Active Metabolite, 7-Ethyl-10-hydroxycamptothecin (SN-38), by Human Liver Carboxylesterase," *Biochemical Pharmacology* 52:1103-1111.

Rosenthal, M.A. et al. (2005, e-pub. May 9, 2005). "Phase I and Pharmacokinetic Evaluation of Intravenous Hyaluronic Acid in Combination with Doxorubicin or 5-Fluorouracil," *Chemotherapy* 51:132-141.

Takasuna, K. et al. (Aug. 15, 1996). "Involvement of β-Glucuronidase in Intestinal Microflora in the Intestinal Toxicity of the Antitumor Camptothecin Derivative Irinotecan Hydrocholoride (CPT-11) in Rats," *Cancer Research* 56:3752-3757.

Turley, E.A. (Mar. 1992). "Hyaluronan and Cell Locomotion," *Cancer and Metastasis Reviews* 11(1):21-30.

U.S. Appl. No. 09/889,203, filed Jan. 6, 2000, by Brown.

U.S. Appl. No. 12/482,870, filed Jun. 11, 2009, by Brown et al.

Yamamoto, O.H. et al. (1993). "Synthesis of the Conjugate of Adriamycin with Oxidized Hyaluronic Acid," *42$^{nd}$ Society of Polymer Science Japan Annual Conference Proceedings, Polymer Preprints*, Japan 42(3):898. (with English translation, eight pages.).

(56) References Cited

OTHER PUBLICATIONS

Yomota, C. (Jul. 3, 1997). "Research for Property Evaluation and Application of Hyaluronic Acid as a Biomedical Polymer," *1996 Human Science Fundamental Research Enterprise, Human Science Enterprise*, 16 pages (with English translation, 32 pages.).
Mürdter, T.E. et al. (Jun. 15, 1997, e-published Jun. 1, 1997). "Enhanced Uptake of Doxorubicin into Bronchial Carcinoma: β-Glucuronidase Mediates Release of Doxorubicin froma Glucuronide Prodrug (HMR 1826) at the Tumor Site," *Cancer Research* 57:2440-2445.
Tsatas, D. et al. (2002). "EGF Receptor Modifies Cellular Responses to Hyaluronan in Glioblastoma Cells Lines," *Journal of Clinical Neuroscience* 9(3):282-288.
Non-Final Office Action mailed Apr. 15, 2011, for U.S. Appl. No. 11/996,733, Internationally filed Jul. 27, 2006, 31 pages.
Final Office Action mailed May 2, 2011, for U.S. Appl. No. 11/191,407, filed Jul. 27, 2005, 13 pages.
Anonymous. (1957). "British Standard Methods for the Determination of the Viscosity of Liquids in C.G.S. Units," *British Standards Institution*, British Standards House, London, 4 pages.
Anonymous. (Jul. 2008). "Sodium Hyaluronate," *European Pharmacopoeia* 62:3835-3837.
Barrow, G.M. (1979). *Physical Chemistry, Fourth Edition*, Jackson, D.C. eds., McGraw-Hill Kogakusha, Ltd., Tokyo, Japan, pp. 764-765.
Cunningham, D. et al. (Jul. 22, 2004). "Cetuximab Monotherapy and Cetuximab Plus Irinotecan in Irinotecan-Refractory Metastatic Colorectal Cancer," *New England Journal of Medicine*, download from <http://www.nejm.org>, last visited on Sep. 30, 2010, 351(4):337-345.
Final Office Action mailed Apr. 30, 2010, for U.S. Appl. No. 11/415,612, filed May 1, 2006, 13 pages.
Final Office Action mailed Nov. 29, 2010, for U.S. Appl. No. 09/889,203, filed Mar. 13, 2002, 9 pages.
Hokputsa, S. et al. (2003). "Hydrodynamic Characterisation of Chemically Degraded Hyaluronic Acid," *Carbohydrate Polymers* 52:111-117.
Non-Final Office Action mailed Mar. 25, 2010, for U.S Appl. No. 09/889,203, filed Jan. 6, 2000, 11 pages.
Non-Final Office Action mailed Oct. 8, 2010, for U.S. Appl. No. 12/065,945, filed Sep. 29, 2008, 14 pages.
Non-Final Office Action mailed, Nov. 15, 2010, for U.S. Appl. No. 11/191,407, filed Jul. 27, 2005, 12 pages.
Stern, R. et al. (2006). "Hyaluronan Fragments: An Information-Rich System," *European Journal of Cell Biology* 85:699-715.
Wikipedia. (download on Sep. 13, 2010). "Intrinsic Viscosity," located at <http://en.wikipedia.org/wiki/Intrinsic_viscosity>, 3 pages.
Wikipedia. (download on Sep. 13, 2010). "Mark-Houwink Equation," located at <http://en.wikipedia.org/wiki/Mark%E2%80%93Houwink_equation>, 2 pages.
Wikipedia. (downloaded on Sep. 13, 2010). "Viscosity," located at <http://en.wikipedia.org/wiki/Viscosity>, 18 pages.
Zhen, Y. et al. (eds). (Nov. 2002). *Modern Biotechnological Pharmaceutics Series*, Antibody Engineering Pharmaceutics, Chemical Industry Press et al., Beijing, China, pp. 303-302, with Certified English Translation, for a total of 10 pages.
Gustafson, S. et al. (1995). "Studies on Receptors for Hyaluronan and the Turnover of Radioactively-Labelled Hyaluronan in Mice and Rats," *Second International Workshop on Hyaluronan in Drug Delivery, Round Table Services*, Willoughby, D.A. ed., Ontario, Canada, 36:5-7.
Brownlee, G.R. et al. (Apr. 2006). "Novel Formulations of Therapeutic Antibodies with Hyaluronic Acid (HA) in the Treatment of Colorectal Cancer: A Pre-clinical Evaluation," *Proceedings of the American Association for Cancer Research*, 97th *Annual Meeting*, Washington, DC, Apr. 1-5, 2006, 47:162, Abstract No. 682.

Declaration of Samuel Simon Asculai Under § 1.132 (1996) filed on Sep. 19, 1996 for U.S. Patent No. 6,069,135 (Issued on May 30, 2000), which Matured Out of U.S. Appl. No. 07/675,908, 239 Total Pages.
Declaration of Ian Constable Under § 1.132 (1996) filed on Sep. 20, 1996 for U.S. Patent No. 6,069,135 (Issued on May 30, 2000), which Matured Out of U.S. Appl. No. 07/675,908, 45 Total Pages.
Declaration of George A. Deveber Under § 1.132 (1996) filed on Mar. 4, 1997 for U.S. Patent No. 6,069,135 (Issued on May 30, 2000), which Matured Out of U.S. Appl. No. 07/675,908, 16 Total Pages.
Declaration of Joseph Robert Emmott Fraser Under § 1.132 (1996) filed on Mar. 4, 1997 for U.S. Patent No. 6,069,135 (Issued on May 30, 2000), which Matured Out of U.S. Appl. No. 07/675,908, 62 Total Pages.
Declaration of Joseph Robert Emmott Fraser Under § 1.132 (1997) filed on Aug. 7, 1997 for U.S. Patent No. 6,069,135 (Issued on May 30, 2000), which Matured Out of U.S. Appl. No. 07/675,908, 71 Total Pages.
Declaration of Joseph Robert Emmott Fraser Under § 1.132 (1997) for U.S. Patent No. 5,985,850 (Issued on Nov. 16, 1999), which Matured Out of U.S. Appl. No. 08/462,154, 67 Total Pages.
Declaration of Stefan Gustafson Under § 1.132 (1996) filed on Mar. 4, 1997 for U.S. Patent No. 6,069,135 (Issued on May 30, 2000), which Matured Out of U.S. Appl. No. 07/675,908, 126 Total Pages.
Declaration of Torvard C. Laurent Under § 1.132 (1996) filed on Dec. 18, 1996 for U.S. Patent No. 6,069,135 (Issued on May 30, 2000), which Matured Out of U.S. Appl. No. 07/675,908, 46 Total Pages.
Declaration of Dr. Adrian Richard Moore Under § 1.132 (1996) filed on Mar. 4, 1997 for U.S. Patent No. 6,069,135 (Issued on May 30, 2000), which Matured Out of U.S. Appl. No. 07/675,908, 27 Total Pages.
Declaration of Sanford H. Roth Under § 1.132 (1996) filed on Mar. 4, 1997 for U.S. Patent No. 6,069,135 (Issued on May 30, 2000), which Matured Out of U.S. Appl. No. 07/675,908, 53 Total Pages.
Declaration of Eva Turley Under § 1.132 (1996) filed on Mar. 4, 1997 for U.S. Patent No. 6,069,135 (Issued on May 30, 2000), which Matured Out of U.S. Appl. No. 07/675,908, 30 Total Pages.
Declaration of Eva Turley Under § 1.132 (1997) filed on Aug. 7, 1997 for U.S. Patent No. 6,069,135 (Issued on May 30, 2000), which Matured Out of U.S. Appl. No. 07/675,908, 60 Total Pages.
Declaration of Eva Turley Under § 1.132 (1997) filed on Apr. 14, 1999 for U.S. Patent No. 5,985,850 (Issued on Nov. 16, 1999), which Matured Out of U.S. Appl. No. 08/462,154, 68 Total Pages.
Final Office Action mailed May 10, 2011, for U.S. Appl. No. 12/065,945, filed Sep. 29, 2008, 10 pages.
Final Office Action mailed on Dec. 13, 2011, for U.S. Appl. No. 11/996,733, filed Jun. 19, 2008, 34 pages.
Non-Final Office Action mailed on Jun. 30, 2011, for U.S. Appl. No. 12/482,870, filed Jun. 11, 2009, 11 pages.
Non-Final Office Action mailed, Jul. 6, 1994 for U.S. Patent No. 6,069,135 (Issued on May 30, 2000), which Matured Out of U.S. Appl. No. 07/675,908, 9 pages.
Non-Final Office Action mailed, Jun. 25, 1996 for U.S. Patent No. 5,985,850 (Issued on Nov. 16, 1999), which Matured Out of U.S. Appl. No. 08/462,154, 6 pages.
Non-Final Office Action mailed, Aug. 8, 2008, for U.S. Appl. No. 11/191,407, filed Jul. 27, 2005, 11 pages.
Non-Final Office Action mailed, Dec. 7, 2007, for U.S. Appl. No. 11/191,407, filed Jul. 27, 2005, 7 pages.
Non-Final Office Action mailed on Aug. 30, 2013, for U.S. Appl. No. 13/325,842, filed Dec. 14, 2011, 10 pages.
Pályi-Krekk, Z. et al. (Nov. 1, 2007). "Hyaluronan-Induced Masking of ErbB2 and CD44-Enhanced Trastuzumab Internalisation in Trastuzumab Resistant Breast Cancer," *European Journal of Cancer* 43(16):2423-2433.
Response to Non-Final Office Action submitted to the USPTO Dec. 19, 1996 for U.S. Patent No. 5,985,850 (Issued on Nov. 16, 1999), which Matured Out of U.S. Appl. No. 08/462,154, 30 pages.

(56) References Cited

OTHER PUBLICATIONS

Response to Non-Final Office Action submitted to the USPTO Dec. 22, 1997 for U.S. Patent No. 5,985,850 (Issued on Nov. 16, 1999), which Matured Out of U.S. Appl. No. 08/462,154, 32 pages.
Response to Non-Final Office Action submitted to the USPTO Jan. 9, 1995 for U.S. Patent No. 6,069,135 (Issued on May 30, 2000), which Matured Out of U.S. Appl. No. 07/675,908, 52 pages.
Rugo, H. (2004). "Bevacizumab in the Treatment of Breast Cancer: Rationale and Current Data," *The Oncologist* 9, suppl. 1, pp. 43-49.
Stedman (2005). *Stedman's Medical Dictionary for the Health Professions and Nursing*, Fifth Edition, Lippincott Williams & Wilkins: Baltimore, MD, pp. 766-767.
Váradi, T. et al. (Aug. 2012; e-pub. May 4, 2012). "Binding of Trastuzumab to ErbB2 is Inhibited by a High Pericellular density of Hyaluronan," *J. Histochem. Cytochem.* 60(8):567-575.
Wikipedia (Feb. 25, 2014). "Dispersity (redirected from Polydispersity Index)," located at <http://en.wikipedia.org/wiki/Polydispersity_index>, last visited on Feb. 25, 2014, three pages.
U.S. Appl. No. 14/097,029, filed Dec. 4, 2013, by Brown et al., 95 Total Pages.
Declaration of Ian Constable Under § 1.132 (1997) filed on Mar. 4, 1997 for U.S. Patent No. 6,069,135 (Issued on May 30, 2000), which Matured Out of U.S. Appl. No. 07/675,908, 37 Total Pages.

* cited by examiner

All figures represent Mean ± SD, n=4

$IC_{50}$ no HA 3 day drug exposure: 16nM
$IC_{50}$ 100nM HA for 30min, Drug 1h: 4.8nM
$IC_{50}$ 100nM HA for 30 min, drug 3 days: 13nM IC$_{50}$ Drug exposed 3 days:58nM
IC$_{50}$ HA/drug exposed 3 days: 15nM
IC$_{50}$ drug 1h, drug-free 3 days:>100nM
IC$_{50}$ HA/Drug 1h, drug-free 3 days:>100nM Figure represent Mean ± SD, n=4

All figures represent Mean ± SD, n=4

$IC_{50}$ exposed drug 3 days: 46nM
$IC_{50}$ 30min HA, drug 3 days: 15nM
$IC_{50}$ 30min HA, Drug 1h: 30nM where each data point is mean ± SEM FIGURE 16A  Equivalent to 30mg/m² DOX clinical dose
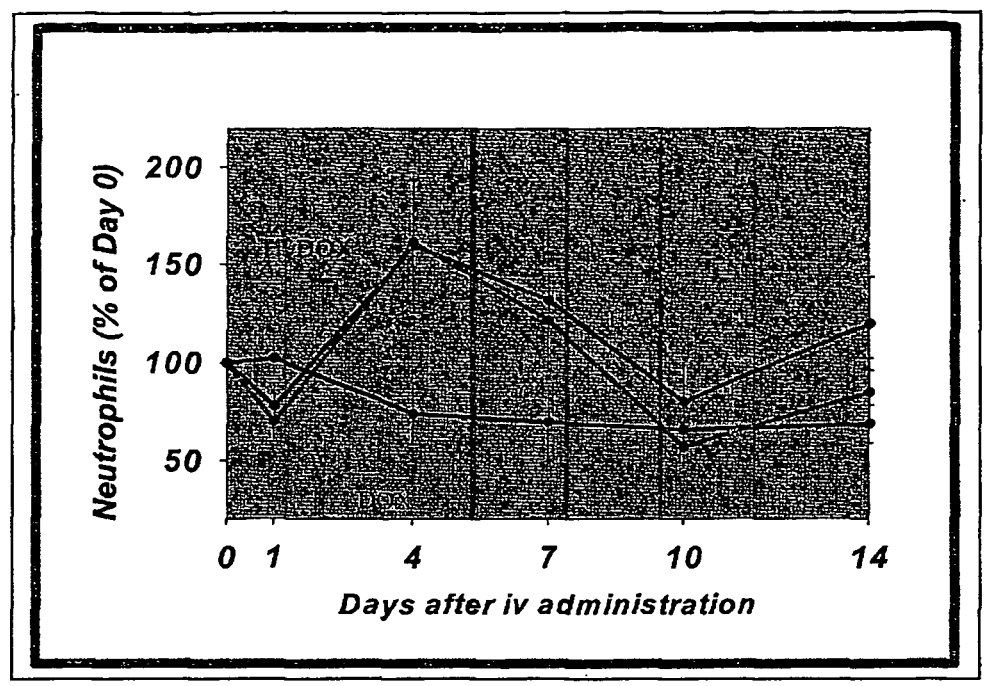
FIGURE 16B  Equivalent to 45mg/m² DOX clinical dose
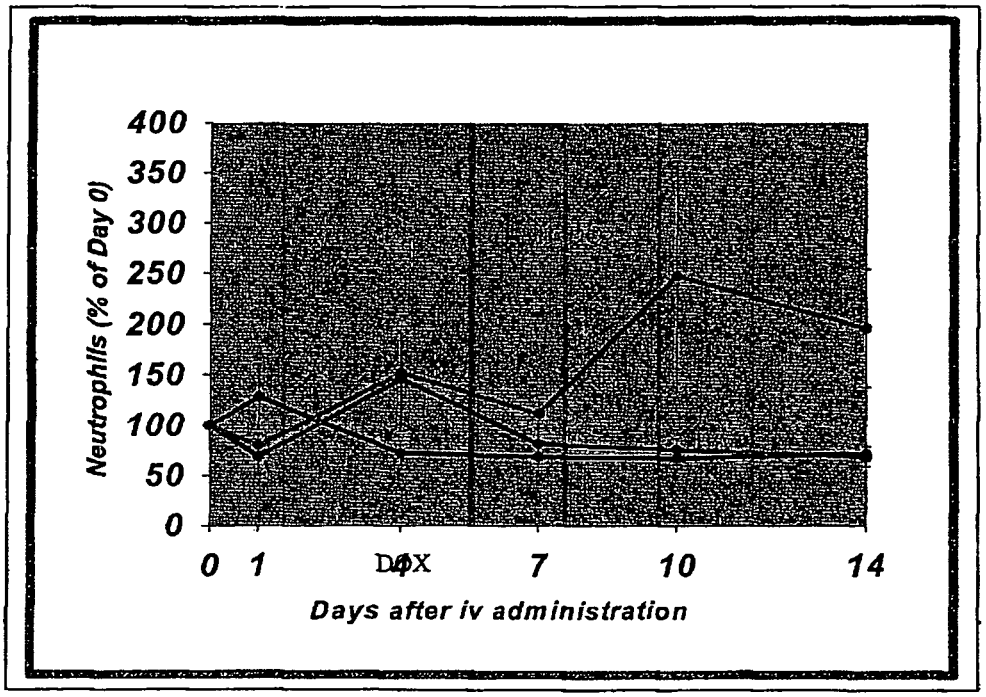

HYALURONAN AS A CHEMO-SENSITIZER IN THE TREATMENT OF CANCER

CROSS-REFERENCE TO RELATED APPLICATIONS

This application is a continuation-in-part of U.S. patent application Ser. No. 10/088,774 (now abandoned), filed on Mar. 13, 2003 Jul. 13, 2001 (Int'l), which is a National Phase application under 35 U.S.C. §371 of International Application No.: PCT/AU01/00849 filed on Jul. 13, 2001 and claims the priority benefit of Australian Application No.: PQ 8795 filed on Jul. 14, 2000, the entire contents of which are incorporated herein by reference.

FIELD OF THE INVENTION

The present invention relates to the enhancement of bioavailability of chemotherapeutic agents for the treatment of disease. In particular, the present invention relates to the use of hyaluronan either alone or in combination with a chemotherapeutic agent, e.g., irinotecan or derivatives thereof, to enhance the bioavailability of the chemotherapeutic agent for treatment of disease. The present invention also relates to the treatment of a drug resistant disease whereby the drug resistance is overcome or alleviated with the use of hyaluronan either alone or in combination with a chemotherapeutic agent, or derivatives thereof.

BACKGROUND TO THE INVENTION

Many diseases that afflict animals, including humans, are treated with chemotherapeutic agents. For example, chemotherapeutic agents have proven valuable in the treatment of neoplastic disorders including connective or autoimmune diseases, metabolic disorders, and dermatological diseases, and many of these agents are highly effective and do not suffer from any bioavailability problems.

Proper use of chemotherapeutic agents requires a thorough familiarity with the natural history and pathophysiology of the disease before selecting the chemotherapeutic agent, determining a dose, and undertaking therapy. Each subject must be carefully evaluated, with attention directed toward factors which may potentiate toxicity, such as overt or occult infections, bleeding dyscrasias, poor nutritional status, and severe metabolic disturbances. In addition, the functional condition of certain major organs, such as liver, kidneys, and bone marrow, is extremely important. Therefore, the selection of the appropriate chemotherapeutic agent and devising an effective therapeutic regimen is influenced by the presentation of the subject. Such considerations affect the dosage and type of drug administered.

Unfortunately, not all chemotherapeutics are readily useable. For example, some chemotherapeutic agents are inherently refractory in that animal cells do not readily respond to these agents, while other chemotherapeutics suffer from acquired resistance. For instance, it is well recognized that some subjects on prolonged chemotherapy are forced to change chemotherapeutics as these become less efficacious with time. Moreover, some chemotherapeutics, while not affected by inherent or acquired resistance per se, are not effective in the treatment of certain diseases as they have innate problems with bioavailability. One disease that is frequently affected by both cellular resistance and bioavailability problems is cancer.

Cancer is responsible for one in four deaths in Western society. While the rates of new cases of cancer and deaths with cancer decreased in the United States and Canada between 1990-1994, the data show that 2,604,650 people in the United States died from cancer between 1990-1994, with more men (53%) than women (47%) affected. The most common cancer deaths were due to cancer of the lung (728,641), colon and rectum (285,724), breast (218,786), and prostate (169,943).

Among women, the most common cancers are breast (31%), lung (12%), colon and rectum (12%), uterus {6%), and ovary (4%), with breast and ovarian cancer representing approximately 35% of all cancers found in women. The majority of women diagnosed with these forms of cancer receive a combination of surgical, radiation therapy or chemotherapy.

Chemotherapeutic agents used to treat cancer can be subdivided into several broad categories, including, (1) alkylating agents, such as mechlorethamine, cyclophosphamide, melphalan, uracil mustard, chlorambucil, busulfan, carmustine, lomustine, semustine, streptozoticin, and decrabazine; (2) antimetabolites, such as methotrexate, fluorouracil, fluorodeoxyuridine, cytarabine, azarabine, idoxuridine, mercaptopurine, azathioprine, thioguanine, and adenine arabinoside; (3) natural product derivatives, such as irinotecan hydrochloride, vinblastine, vincristine, dactinomycin, daunorubicin, doxorubicin, mithramycin, taxanes (e.g., paclitaxel) bleomycin, etoposide, teniposide, and mitomycin C; and (4) miscellaneous agents, such as hydroxyurea, procarbezine, mititane, and cisplatinum.

Particular chemotherapeutic compounds used in the methods and compositions of the invention include topoisomerase I inhibitors such as irinotecan hydrochloride (CAMPTOSAR®, also known as or referred to as CPT 11) (Slichenmyer et al. (1993) *J. Natl. Cancer Inst.* 85:271-291) and derivatives thereof. Exemplary derivatives of irinotecan include, but are not limited to those described in U.S. Pat. No. 6,403,563; U.S. Patent Application No.: 2001/0056082; U.S. Patent Application No.: 2002/00032331; U.S. Pat. No. 6,376, 617; U.S. Patent Application No.: 2004/0048832; U.S. Pat. No. 6,121,451 U.S. Pat. No. 6,235,907; U.S. Pat. No. 6,444, 820, U.S. Pat. No. 6,486,320; U.S. Patent Application No.: 2002/0045756; U.S. Pat. No. 6,500,953; EP Patent No. 0 781 781; EP Patent Application No. 0 757 049; PCT publication WO 03/074527; and PCT publication No. WO 01/30351. The contents of each of the aforementioned patents and patent applications is hereby expressly incorporated herein by reference.

Important cancer chemotherapeutic agents (with the usual effective dosage) to which clinical multidrugresistance has been observed include vinblastine (0.1 mg per kilogram per week), vincristine (0.01 mg per kilogram per week), etoposide (35 to 50 mg per square meter per day), dactinomycin (0.15 mg per kilogram per day), doxorubicin (500 to 600 mg per square meter per week), daunorubicin (65 to 75 mg per square meter per week), and mithramycin (0.025 mg per kilogram per day).

HA, also known as hyaluronic acid, is a naturally occurring polysaccharide comprising linear chain polymers, which is found ubiquitously throughout the animal kingdom. HA is highly water soluble, making it an ideal drug delivery vehicle for biologics.

It was found that HA could exert a cytotoxic effect on human breast cancer cells, as well as pre-sensitizing cells so that they became more susceptible to chemotherapeutic agents. The present invention therefore provides methods whereby cells that were, or had become resistant to chemotherapeutic agents could be effectively treated. More importantly, by using the disclosed methods it is possible to decrease the dosages of chemotherapeutic agents without decreasing the efficacy to the subject. The methods of the invention include administering hyaluronan either alone in conjunction with a chemotherapeutic agent.

The present invention is based upon the discovery that hyaluronan, derivatives, analogues, and salts thereof, not only inhibit cells per se, but also allows the safe administration of selected chemotherapeutic agents at standard or lower doses thought to be less effective, to treat subjects including human subjects. In addition, hyaluronan can reduce side effects associated with chemotherapeutic agents thereby allowing the chemotherapeutic agent to be administered at a dose greater than the standard with equal or less toxicity or at a standard dose but with less toxicity. In vivo administration of hyaluronan in combination with chemotherapeutic agents also enhances the therapeutic effect of these agents against cells that are refractory, thus preventing the subsequent emergence of multidrug resistance.

Diseased cells such as cancer cells often have more permeable membranes due to an alteration in the membrane potential, or increased receptor status which can alter the regulation of their intracellular molecule transport which can result in cell swelling (Lang et al, 1993). While the applicant does not wish to be bound by any theory they postulate that there are several mechanisms that could explain the cellular effect that HA is exerting both as a sole agent, and as a pre-treatment for therapeutic agents:

1). When HA is bound to CD44, RHAMM and the scavenger receptor bound, the net negative charge of HA alters the membrane potential of the cell resulting in an increase in cell permeability consequently enabling a greater flux of drug into the diseases cell.

2). When HA is bound to diseased cells such as tumour cells and internalised there could be a hyperosmotic effect resulting in cell lysis.

3). HA could exert oxidative membrane damage resulting in apoptosis.

4). HA internalisation could elevate the mitochondrial membrane potential which could result in cell death or increased drug retention.

Since HA is administered at satuarable levels, there would be a constant internalisation of the glycosaminoglycan which means that any therapeutic agent which is in an equilibrium within the volumetric domain of the HA is co-internalised resulting in a concentrated intracellular release of the drug

SUMMARY OF INVENTION

In one aspect, the invention provides a method of treating a subject in need thereof comprising the step of administering to said subject a therapeutically effective amount of hyaluronan, or a derivative thereof, in conjunction with a chemotherapeutic agent such that said chemotherapeutic agent is more effective and/or has one or more reduced side effect as compared to the chemotherapeutic agent administered in the absence of hyaluronan. In one embodiment, the hyaluronan reduces one or more side effect associated with the chemotherapeutic agent and the chemotherapeutic agent to be administered at a dose greater than a reference dose for the chemotherapeutic agent administered in the absence of hyaluronan and/or the chemotherapeutic can be administered for one or more cycle more than when the chemotherapeutic is administered in the absence of hyaluronan.

In a preferred embodiment, hyaluronan and irinotecan are administered to the subject. The hyaluronan and irinotecan can be administered intravenously over a period of time, e.g., 10 to 240 minutes, preferably 30 to 180 minutes, more preferably 60 to 120 minutes, e.g., about 90 minutes. The dose can be administered repeatedly, e.g., two, three four, five, six, seven, eight, nine, ten times. The interim period between repeated doses can be 5 to 30 days, preferably 5 to 21 days, e.g., about once a week. One preferred administration is between 200 and 500 mg/m2, e.g., about 300 to 350 mg/m2, of irinotecan, administered at intervals of 15 to 45 days, e.g., 15 to 30 days, e.g., about 21 days, e.g., for up to 5, 6 or 7 cycles. Another preferred administration is between 50 and 300 mg/m2, e.g., about 100 to 200 mg/m2, more preferably 100 to 150 mg/m2, e.g., about 125 mg/m2, of irinotecan, administered at intervals of 5 to 10, preferably 7 days, e.g., for up to 2, 3 or 4 cycles. This can be followed by a period of 5 to 10, preferably 7 days without hyaluronan or irinotecan administered, followed by one or more cycles as described above.

In one embodiment, the hyaluronan, or derivative thereof, has an average molecular weight range of about 775 to 900 kDa, preferably about 800 to 875 kDa, e.g., 825 to 850 kDa. The dose of hyaluronan is preferably about 250 to 5000 mg/m2, more preferably 500 to 2000 mg/m2, more preferably 750 to 1500 mg/m2, more preferably about 900 to 1100 mg/m2, e.g., about 1000 mg/m2.

The present invention also provides a method of enhancing the bioavailability of a chemotherapeutic agent comprising the step of administering to a subject in need thereof a therapeutically effective amount of hyaluronan, or a derivative thereof, e.g., a hyaluronan, or derivative thereof described herein. In one embodiment, the hyaluronic acid, or derivative thereof, has an average molecular weight range of about 775 to 900 kDa, preferably about 800 to 875 kDa, e.g., 825 to 850 kDa.

The chemotherapeutic agent used in any of the methods, compositions or kits described herein can be an alkylating agent, an antimetabolite, a platinum derivative, a topoisomerase inhibitor, an antimicrotubule agent, and a mitotic inhibitor. Examples of chemotherapeutic agents include, but are not limited to, mechlorethamine, cyclophosphamide, melphalan, uracil mustard, chlorambucil, busulfan, carmustine, lomustine, semustine, streptozoticin, decrabazine, methotrexate, fluorouracil, fluorodeoxyuridine, cytarabine, azarabine, idoxuridine, mercaptopurine, azathioprine, thioguanine, adenine arabinoside, irinotecan (CPT 11), vinblastine, vincristine, dactinomycin, daunorubicin, doxorubicin, mithramycin, taxanes (e. g., paclitaxel) bleomycin, etoposide, teniposide, mitomycin C, hydroxyurea, procarbezine, mititane, oxaliplatinum, topotecan, and cisplatinum. In one embodiment, the chemotherapeutic agent is selected from the group consisting of carmustine (BCNU), chlorambucil (Leukeran), cisplatin (Platinol), Cytarabine, doxorubicin (Adriamycin), fluorouracil (5-FU), methoxetrate (Mexate), CPT 11 (irinotecan, Camptosar), etoposide, plicamycin (Mithracin) and taxanes such as, for example, paclitaxel, and derivatives thereof.

In yet another embodiment, the invention provides a method of treating or preventing multidrug resistance or drug-resistant cells comprising the step of administering a therapeutically effective amount of hyaluronan, e.g. hyaluronan or a derivative thereof as described herein, prior to, together with, or subsequent to the administration of a chemotherapeutic agent. In one embodiment, the hyaluronic acid, or derivative thereof, has an average molecular weight range of about 775 to 900 kDa, preferably about 800 to 875 kDa, e.g., 825 to 850 kDa.

As described more fully below, administration of hyaluronan and a chemotherapeutic agent can result in the suppression of tumor growth by at least 40%, 50%; preferably 60%; more preferably, greater than 70%, and even more preferably greater than 80%, 90% or 95%. Accordingly, the elimination of tumor growth and proliferation eliminates the production of multidrug resistant cells thereby reducing the recurrence of cancer and increasing the efficacy of chemotherapeutic treatments. In some embodiments, the administration of hyaluronan reduces or eliminates one or more side effect associated with the chemotherapeutic agent. For example, in one embodiment, the chemotherapeutic agent is irinotecan, or a derivative thereof, and one or more side effect associated with irinotecan, or a derivative thereof, (e.g., diarrhea) is reduced or eliminated.

The present invention further provides a pharmaceutical composition for increasing the sensitivity of cells to chemotherapeutic agents comprising hyaluronan. The hyaluronan and/or chemotherapeutic agent may also be administered together with a further pharmaceutical carrier.

In another aspect, the invention features a preparation of hyaluronan. The preparation can be, e.g., dry (e.g., granulated or lyophilized) or in a solution. In preferred embodiments, the hyaluronan is 700 to 1000 kDa, preferably 800 to 950 kDa, more preferably 800 to 900 kDa, more preferably 800 to 850 kDa, e.g., 825 to 850 kDa, e.g., 825 or 850 kDa. When in a solution, the diluent can be water for injection (WFI), saline or a pharmaceutically suitable equivalent. In a preferred embodiment, the percentage by weight/weight, volume/volume or weight/volume of hyaluronan in the preparation is 0.5 to 5%, more preferably 0.5 to 3%, 0.5 to 1.5% or about 1%. A preferred formulation includes one or more excipient such as sorbitol, lactic acid, and dextrose or their salts or equivalents. The preparation can be provided in a water or gas tight container having 1 to 1000 ml of a solution of hyaluronan or 1 to 1000 mg of a dry formulation of hyaluronan. In a preferred embodiment, it can also include a chemotherapeutic agent, e.g., irinotecan. In a preferred embodiment, the preparation is made by a method which includes comparing a property of the preparation to a reference value for that property. Preferably, the reference value is provided in an FDA approved protocol for the production or use of hyaluronan, e.g., for intravenous injection. Preferably, the protocol is in an approved New Drug Application (NDA), Biologics License Application (BLA), Abbreviated New Drug Application (ANDA) or other post-IND or post-clinical trial approval. In a preferred embodiment, the method of making the preparation includes filing an IND, NDA, BLA, ANDA with the FDA for approval to use the hyaluronan in intravenous injection.

Also included in the invention are methods of making any of the compositions disclosed herein, e.g., a method of making an hyaluronan preparation which method includes determining if the preparation complies with a requirement set out in an FDA approved protocol for production or use of hyaluronan. Preferably, the protocol is in an approved New Drug Application (NDA), Biologics License Application (BLA), Abbreviated New Drug Application (ANDA) or other post-IND or post-clinical trial approval. In a preferred embodiment, the method of making the preparation includes filing an IND, NDA, BLA, ANDA with the FDA for approval to use the hyaluronan in intravenous injection.

The invention also features a kit that includes a container comprising a dry or liquid preparation of hyaluronan, e.g., as described herein. The kit can further include a chemotherapeutic agent, e.g., irinotecan. The chemotherapeutic agent can be included in the same container as the hyaluronan or can be in a separate container. If more than one component is present in the kit, each of the components can be disposed in a chamber of a multiple chambered device, e.g., a dual chambered device. For example, the kit can include a multiple chambered device comprising a dry product, e.g., dry hyaluronan or dry hyaluronan and irinotecan, in one chamber and a liquid component, e.g., a diluent, in a second chamber. In one embodiment, hyaluronan, e.g., liquid hyaluronan, is provided in one chamber and a chemotherapeutic agent, e.g., a liquid chemotherapeutic agent, e.g., irinotecan, is provided in a second chamber. A multiple chamber device can be configured such that an end user can rupture material which separates two or more of the chambers, thereby mixing the contents of at least two of the chambers. Examples of such devices include multiple chambered syringes and multiple chambered bags, e.g., infusion bags.

The present invention also provides a method of treating cancer cells comprising the step of administering to a patient in need thereof a therapeutically effective amount of hyaluronan, e.g., a hyaluronan, or derivative thereof, described herein. The administration can be, e.g., by a method and/or dose described herein.

Typically said cancer cells are resistant to chemotherapeutic drugs.

In a further aspect of the present invention there is provided a method of overcoming cellular resistance, comprising the step of administering a therapeutically effective amount of HA, e.g., a hyaluronan or derivative thereof described herein.

In another embodiment, the invention provides compositions comprising hyaluronic acid and a therapeutically effective amount of a chemotherapeutic, e.g., irinotecan or a derivative thereof. In one embodiment, the hyaluronan is 700 to 1000 kDa, preferably 800 to 950 kDa, more preferably 800 to 900 kDa, more preferably 800 to 850 kDa, e.g., 825 to 850 kDa, e.g., 825 or 850 kDa. In one embodiment, the anticancer agent is irinotecan and the therapeutically effective amount of the irinotecan is, e.g., an amount described herein. In another embodiment, the hyaluronan is present in an amount described herein.

In another embodiment, the invention provides the for the use of a composition comprising a therapeutically effective amount of an anticancer agent and hyaluronic acid, or a derivative thereof for the treatment of cancer. In a related embodiment, the composition comprises hyaluronic acid, or a derivative thereof and irinotecan, or a derivative thereof. In another related embodiment, the composition comprises hyaluronic acid with a modal molecular weight of hyaluronic acid is about 700 to 1000 kDa, preferably 800 to 950 kDa, more preferably 800 to 900 kDa, more preferably 800 to 850 kDa, e.g., 825 to 850 kDa, e.g., 825 or 850 kDa. In specific embodiments, the use of the composition results in partial tumor regression, e.g., the tumor volume is reduced by at least 60%, 70%, 80%, 90% or 95%. In another specific embodiment, the use of the composition results in total tumor regression.

In another embodiment, the invention provides a method of treating a subject having cancer comprising administering to said subject a composition comprising hyaluronic acid and an effective amount of irinotecan, thereby treating the subject. The dose and/or administration can be, e.g., as described herein. In a related embodiment, the composition comprises hyaluronic acid, or a derivative thereof and irinotecan, or a derivative thereof. In another related embodiment, the composition comprises hyaluronic acid with a modal molecular weight of hyaluronic acid is 700 to 1000 kDa, preferably 800 to 950 kDa, more preferably 800 to 900 kDa, more preferably 800 to 850 kDa, e.g., 825 to 850 kDa, e.g., 825 or 850 kDa. In specific embodiments, the hyaluronic acid is administered at a concentration of about 10 mg/kg to about 150 mg/kg, 25 mg/kg to about 100 mg/kg, or at 50 mg/kg.

Throughout the description and claims of this specification, the word "comprise" and variations of the word, such as "comprising" and "comprises", means "including but not limited to" and is not intended to exclude other additives, components, integers or steps.

BRIEF DESCRIPTION OF THE FIGURES

FIG. 8A depicts the effect of increasing concentrations of hyaluronan on MDA-MB-435. FIG. 8B depicts the effect of increasing concentrations of hyaluronan on MDA-MB-468.

FIG. 9A depicts the mean tumor volume as a function of time after administration for saline (open circles), hyaluronan administered days 1 and 2 of 6×q7 D (open triangles), and hyaluronan administered days 1 and 3 of 6×q7 (closed triangles).

FIG. 11A depicts a graph demonstrating the effects of DOX and HyDOX™ on tumor volume as a function of the number of cycles of treatment. FIG. 11B depicts a bar graph showing the tumor viability in animals treated with DOX or HyDOX™.

FIGS. 16A-B are graphs demonstrating the toxicity of hyaluronan, DOX and HyDOX™. FIG. 16A depicts the results of the administration of the equivalent of 30 mg/m$^2$ DOX clinical dose. The percentage of neutrophils at Day 0 is plotted against the number of days after administration of the indicated compounds. FIG. 16B depicts the results of the administration of the equivalent of 45 mg/m$^2$ DOX clinical dose. The percentage of neutrophils at Day 0 is plotted against the number of days after administration of the indicated compounds.

DETAILED DESCRIPTION OF THE INVENTION

Figure 1:
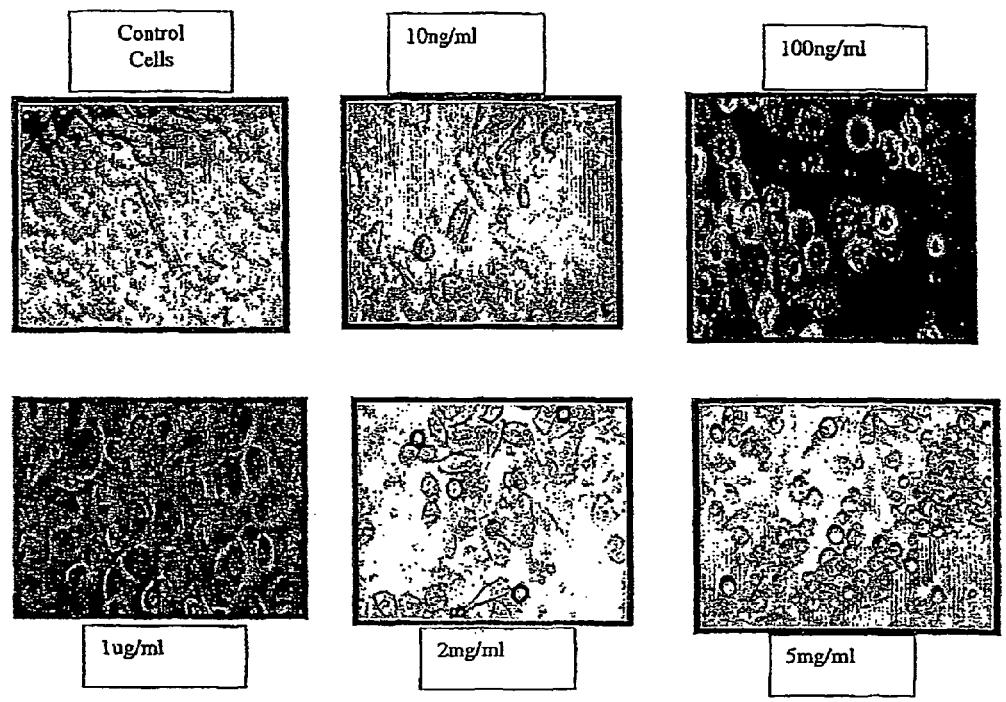
FIG. 1 shows exponentially growing breast cancer cells exposed to 750,000 dalton HA for 24 h at which stage the cells were photographed. At 10 ng/ml there was a reduction in cell number, but no difference in morphology was noted. At 100 ng/ml and 1 μg/ml the cells appeared top be undergoing a osmotic response where the cells appeared to swell. At 2 mg/ml and 5 mg/ml the cells became granular and the plasma membrane was "pitted" possibly indicating an osmotic response and/or the commencement of cell death.
Figure 2A:
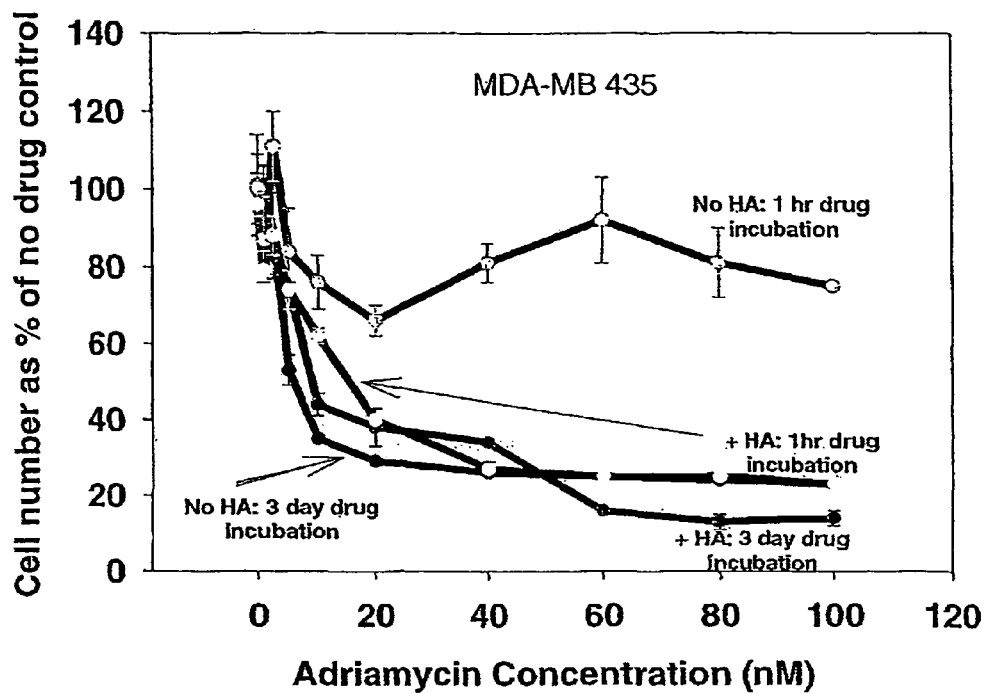
FIG. 2a-2f shows exponentially growing breast cancer cells that were exposed to 750,000 dalton HA for 30 min, 1 h, or 24 h at which stage the cells were varying concentrations of adriamycin. These figures also illustrate the effect of HA/drug co-incubation for the period of 1 or 3 days. These diagrams illustrate that HA can "pre-sensitise" and/or chemosensitise cells to therapeutic drugs.
Figure 2B:
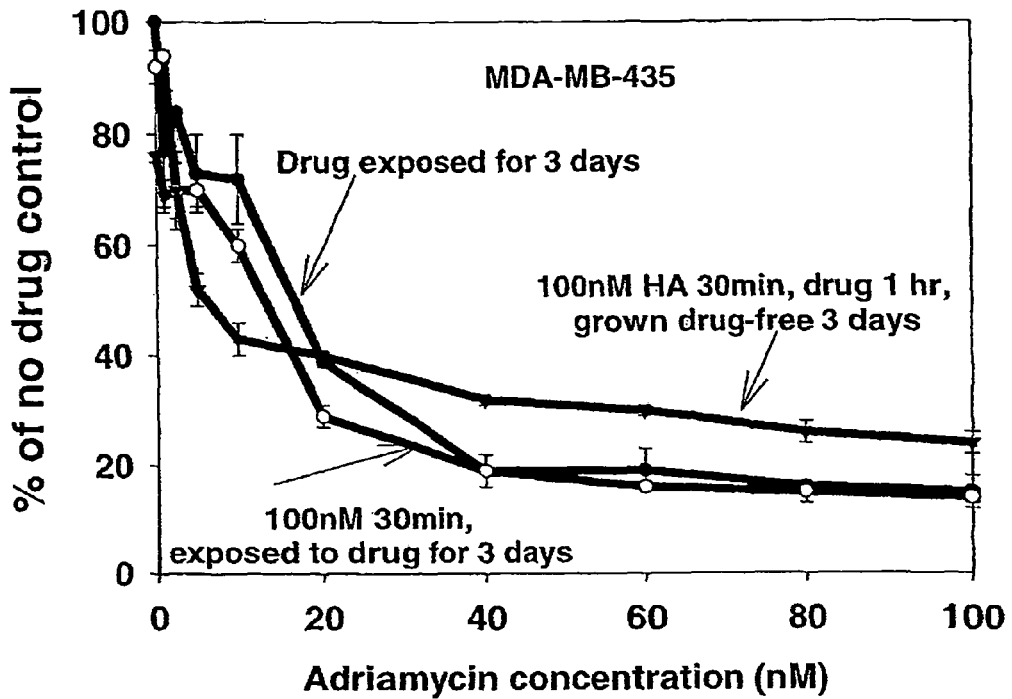
Figure 2C:
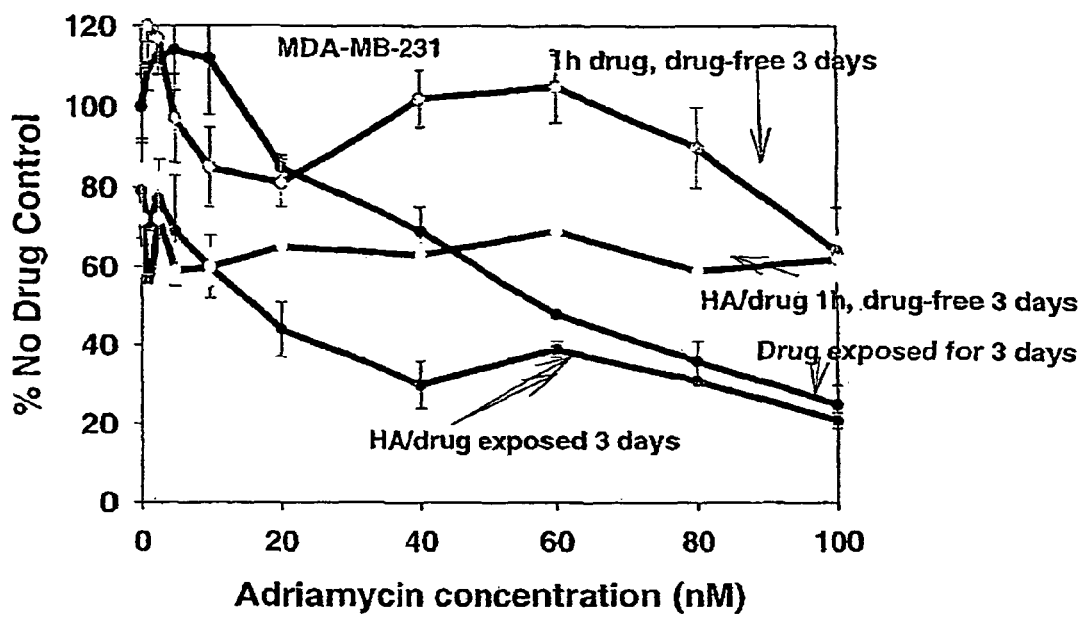
Figure 2D:
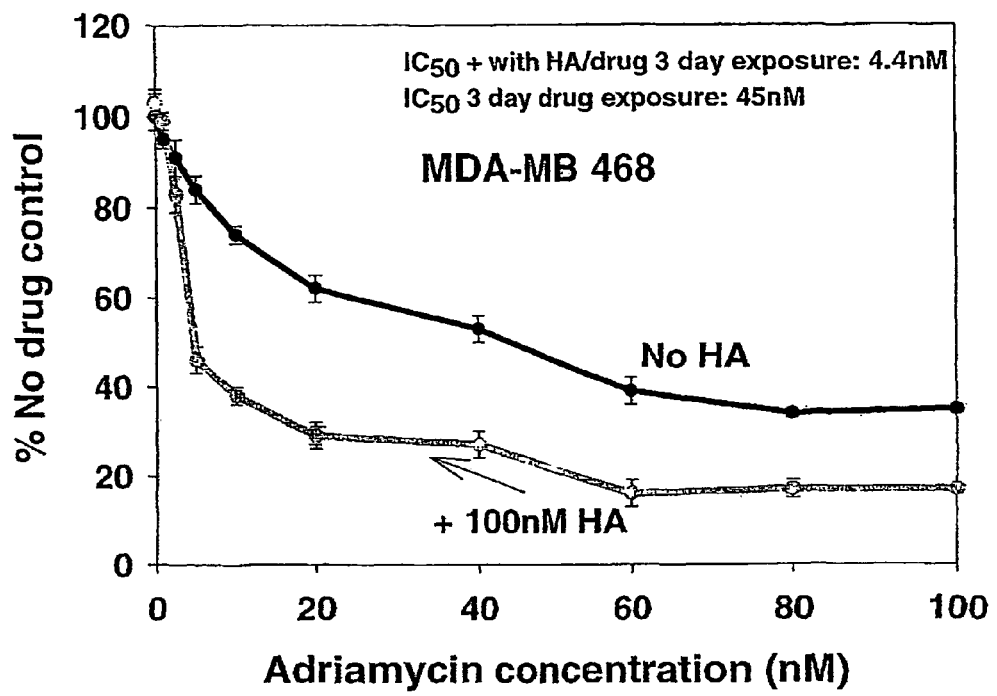
Figure 2E:
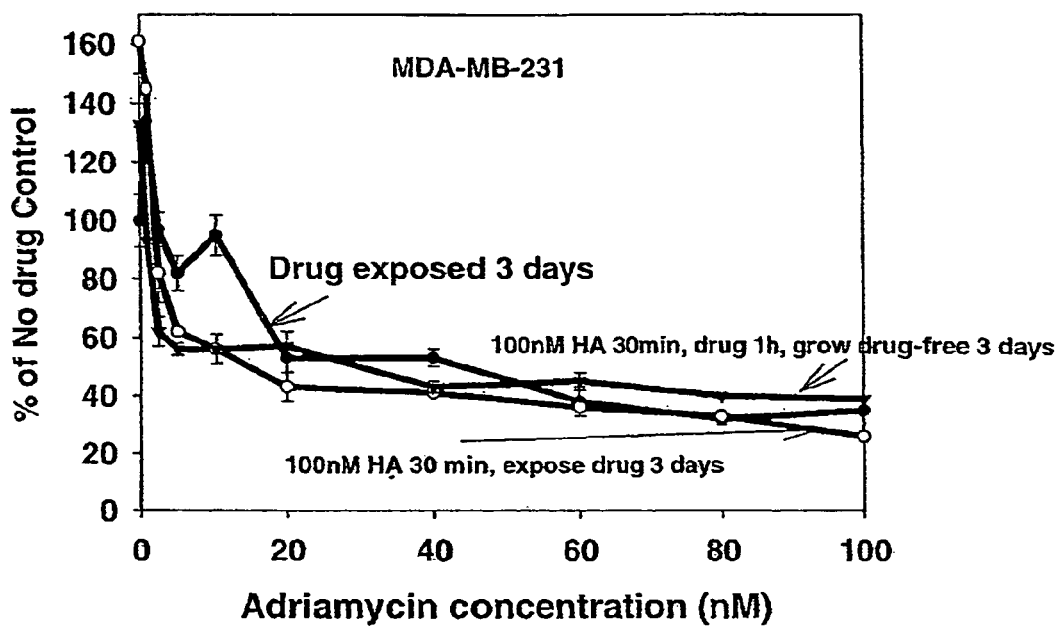
Figure 2F:
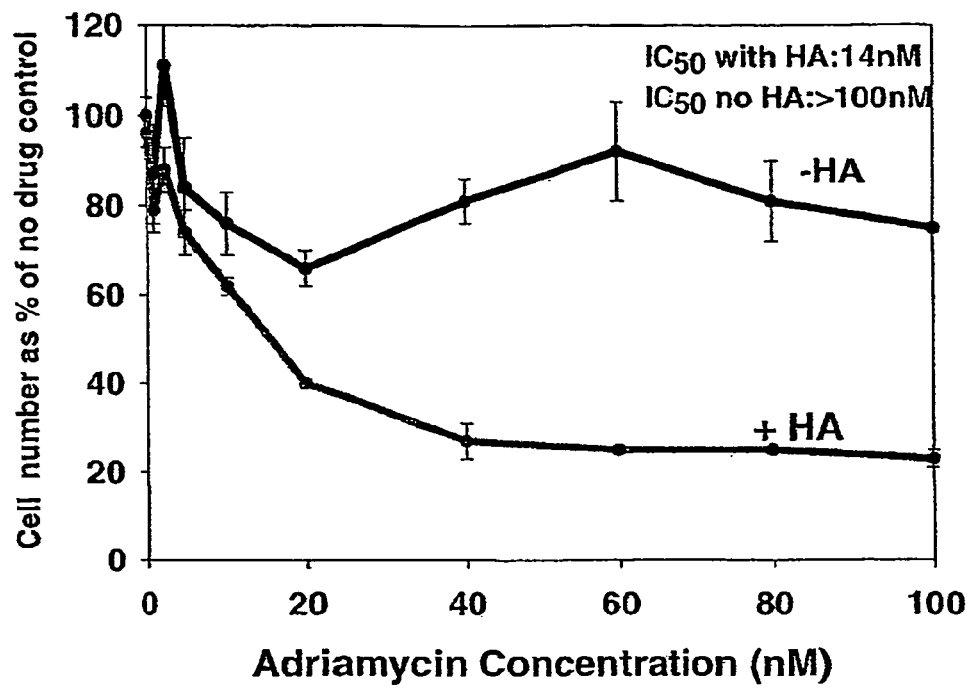
Figure 3A:
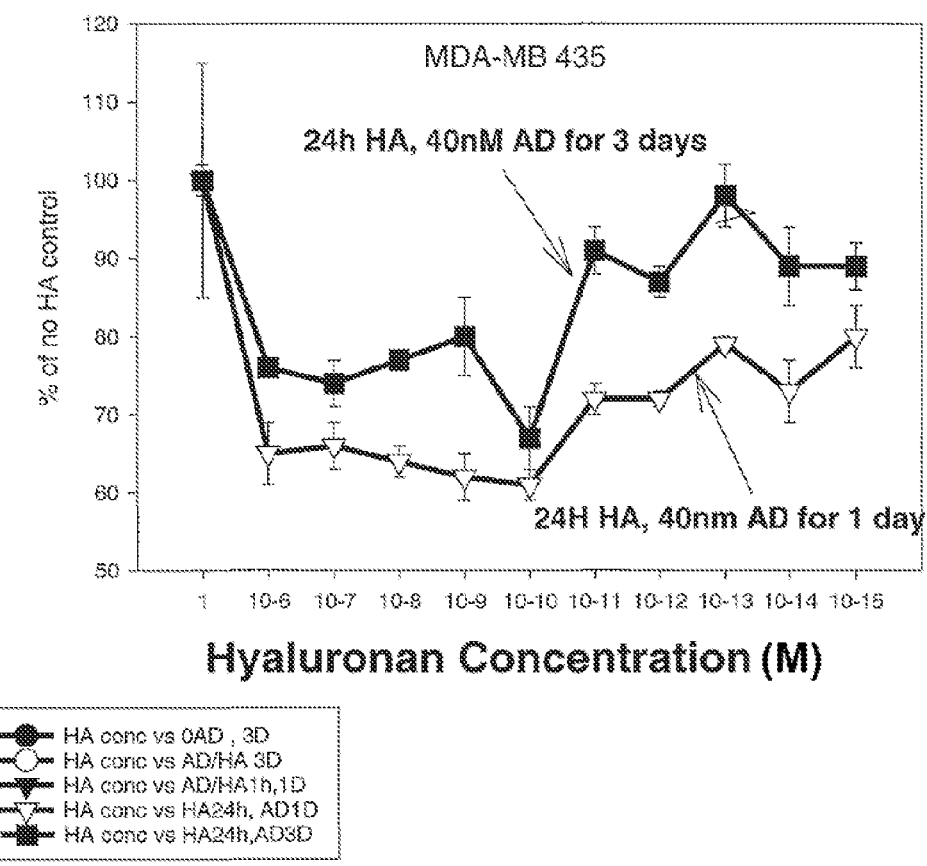
FIGS. 3a-3d shows exponentially growing breast cancer cells exposed to varying concentrations of 750,000 dalton hyaluronan for 1 h, 24 h or 3 days followed by treatment with 40 nM Adriamycin for varying time periods of 1 h, 24 h or 3 days. These figures show that a wide concentration range of hyaluronan can act as a chemosenitiser or exert a cytotoxic effect.
Figure 3B:
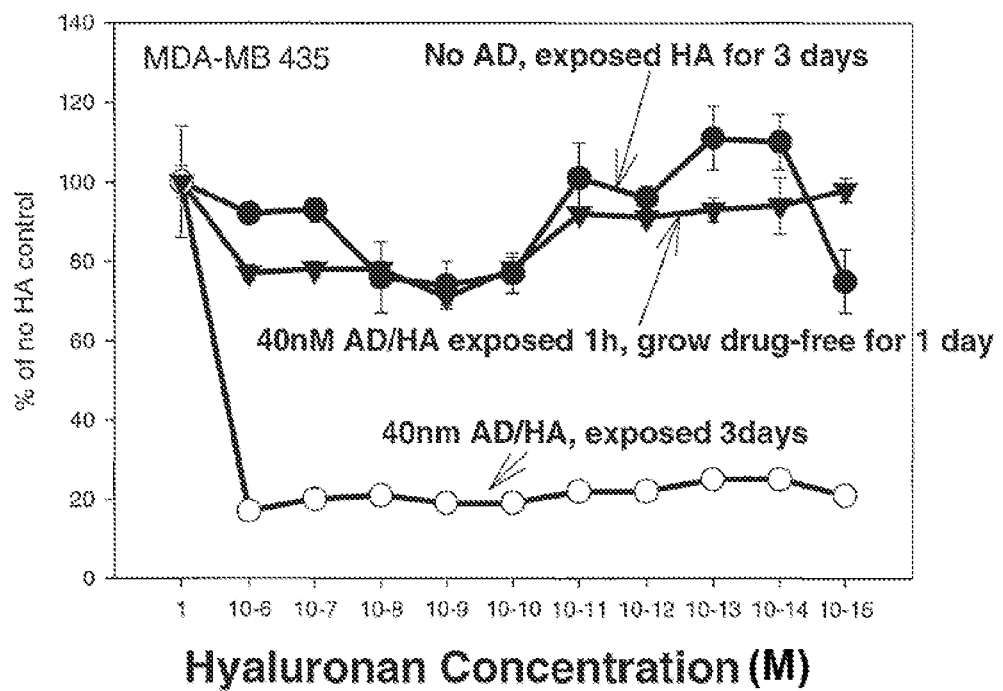
Figure 3C:
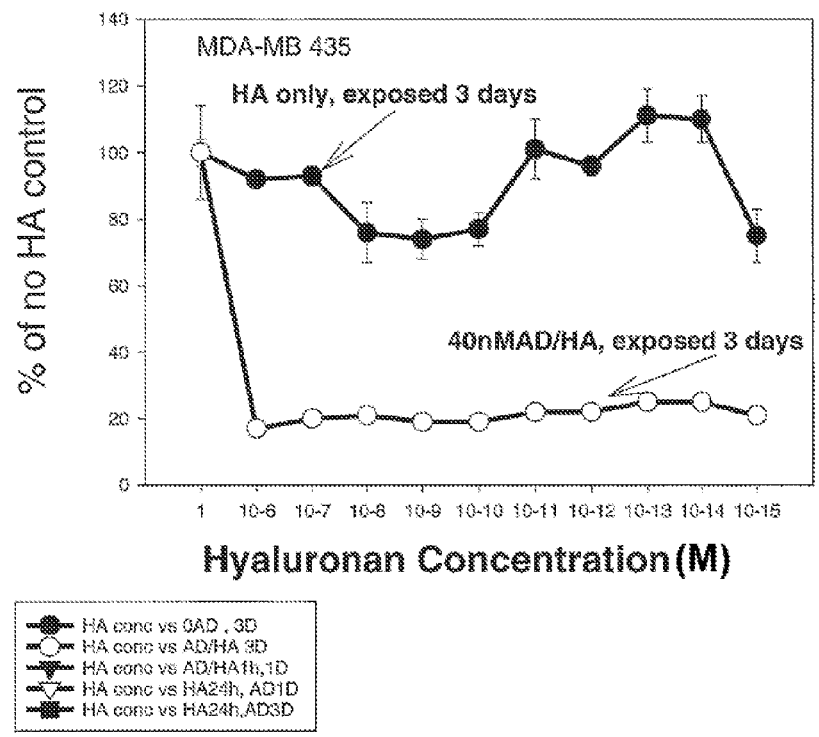
Figure 3D:
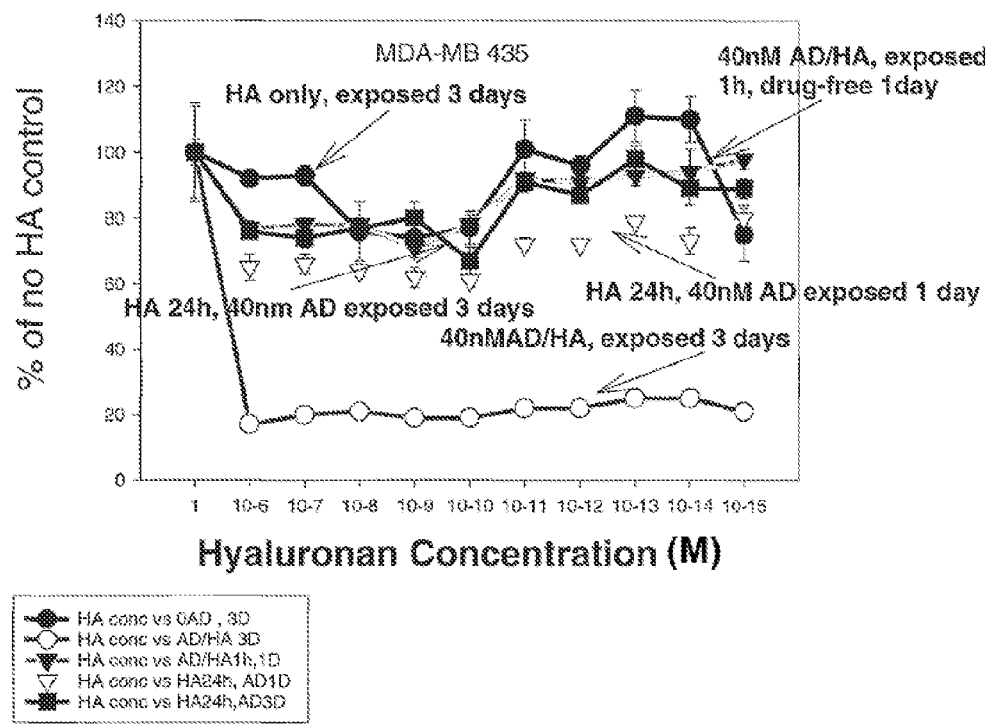

The methods and compositions of the invention are useful for increasing the sensitivity of cells to chemotherapeutic agents such as, for example, anti-cancer agents like paclitaxel or irinotecan, analgesics, opiates, hormones or antibiotics and the like. In particular the methods and compositions of the invention are useful for increasing the sensitivity of cells associated with cellular proliferative disorders (eg., a neoplasm). By increasing the efficacy without concomitant toxicity to non-cancer cells, the invention provides methods and compositions useful for treating tumors and preventing or reducing the chances of relapse and death as a result of cytotoxicity. In addition, the invention eliminates or reduces the number of multidrug resistant cells by eliminating cancer cells prior to any mutation inducing a multidrug resistant phenotype. Accordingly, by reducing multi-drug resistant tumor cells from arising, the invention satisfies the shortcomings of current therapeutic modalities.

The term "subject" as used herein refers to any animal having a disease or condition which requires treatment with a chemotherapeutic agent wherein the chemotherapeutic agent has reduced efficacy relative to that desired. Preferably the subject is suffering from a cellular proliferative disorder (eg., a neoplastic disorder). Subjects for the purposes of the invention include, but are not limited to, mammals (eg., bovine, canine, equine, feline, porcine) and preferably humans.

By "cell proliferative disorder" is meant that a cell or cells demonstrate abnormal growth, typically aberrant growth, leading to a neoplasm, tumor or a cancer.

Cell proliferative disorders include, for example, cancers of the breast, lung (e.g., small cell lung cancer or non-small cell lung cancer), prostate, kidney, skin, neural, ovary, uterus, liver, pancreas, epithelial, gastric, intestinal, colorectal, exocrine, endocrine, lymphatic, haematopoietic system or head and neck tissue. In some embodiments, the cancer is a solid tumor, e.g., renal, urothelial (e.g., bladder), testicular, colon, rectal, lung (e.g., small cell lung carcinoma), breast, liver, kidney, skin, neural (e.g., neuroendocrine), uteral, pancreatic (e.g., pancreatic duct), or gastric cancer.

Generally, neoplastic diseases are conditions in which abnormal proliferation of cells results in a mass of tissue called a neoplasm or tumor. Neoplasms have varying degrees of abnormalities in structure and behaviour. Some neoplasms are benign while others are malignant or cancerous. An effective treatment of neoplastic disease would be considered a valuable contribution to the search for cancer preventive or curative procedures.

The methods of this invention involve in one embodiment, (1) the administration of hyaluronan, prior to, together with, or subsequent to the administration of a chemotherapeutic agent; or (2) the administration of a combination of hyaluronan and a chemotherapeutic agent.

As used herein, the term "therapeutically effective amount" is meant an amount of a compound of the present invention effective to yield a desired therapeutic response. For example to prevent cancer or treat one or more symptom of cancer in a host or an amount effective to treat cancer.

The specific "therapeutically effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical carrier" is a pharmaceutically acceptable solvent, suspending agent or vehicle for delivering the hyaluronan and/or chemotherapeutic agent to the animal or human. The carrier may be liquid or solid and is selected with the planned manner of administration in mind.

As used herein, "cancer" refers to all types of cancers or neoplasm or malignant tumours found in mammals. Cancer includes sarcomas, lymphomas and other cancers. The following types are examples, but are, but is not intended to be limited to these particular types of cancers: prostate, colon (colorectal), breast, both the MX-1 and the MCF lines, pancreatic, neuroblastoma, rhabdomysarcoma, home, lung (small cell lung cancer and non small cell lung cancer), murine, melanoma, leukemia, pancreatic, melanoma, ovarian, brain, head & neck, kidney, mesothelioma, sarcoma, Kaposi's, sarcoma, stomach, and uterine. In some embodiments, the cancer is a solid tumor, e.g., renal, urothelial (e.g., bladder), testicular, colon, rectal, lung (e.g., small cell lung carcinoma), breast, liver, kidney, skin, neural (e.g., neuroendocrine), uteral, pancreatic (e.g., pancreatic duct), or gastric cancer.

As used herein, the term "cell" include but is not limited to mammalian cells (e.g., mouse cells, rat cells or human cells).

The instant invention also provides compositions including one or more chemotherapeutic agents and derivatives, fragments and/or salts of hyaluronan (hyaluronic acid). A number of derivatives and fragments of hyaluronan have been described in the literature and are intended to be included in the methods and formulations of the instant invention.

A preferred formulation comprises irinotecan as the active ingredient and excipients sorbitol, lactic acid, hyaluronic acid and dextrose or their salts or equivalents. Particular examples of formulations provide, after administration final concentrations of 0.35-1.4 mg/ml irinotecan, 0.79-7.2 mg/ml sorbitol, 0.01-0.06 mg/ml lactic acid, 2.8-4.0 mg/ml hyaluronic acid and 17.6-33.55 mg/ml dextrose. A most preferred formulation is referred to as "HyCAMP" having in the formulation 20 mg/ml irinotecan, 45 mg/ml sorbitol, 0.9 mg/ml lactic acid, 10 mg/ml hyaluronic acid and 50 mg/ml dextrose. The concentration of ingredients in the formulation does depend upon patient surface area, where the surface is assumed to be from about 1.4 to about 2 mg/m$^2$ at a dosage range of from about 125 mg/m$^2$ to about 350 mg/m$^2$, inclusive.

HA is generally selected with a molecular weight range of from about 800 kDa to about 950 kDa such as 800, 810, 820, 830, 840, 850, 860, 870, 880, 890, 900, 910, 920, 930, 940 or 950 kDa. However, HA outside this range is also contemplated by the present invention such as from 1 kDa to 800 kDa or from 950 kDa to about 2 million kDa.

Exemplary hyaluronic acid derivatives are those described in U.S. Pat. No. 6,620,927 (thiol-modified hyaluronic acid derivatives); U.S. Pat. No. 6,552,184 (crosslinked compounds of hyaluronic acid and the derivatives thereof); U.S. Pat. No. 6,579,978 (sulphated compounds of hyaluronic acid and derivatives thereof); U.S. Pat. No. 6,831,172 (crosslinked hyaluronic acids and hemisuccinylated derivates thereof); U.S. Pat. No. 6,027,741 (sulfated hyaluronic acid and esters thereof); European Patent No. 0 138 572 (Hyaluronic acid fragments HYALECTIN and HYALASTINE); U.S. Pat. No. 4,851,521 (hyaluronic acid esters with different aromatic aliphatic and/or araliphatic alcohols); U.S. Pat. No. 5,202,431 (partial esters of hyaluronic acid); U.S. Pat. No. 5,676,964 (crosslinked hyaluronic acid polymers) and EP 0 265 116 (crosslinked esters of hyaluronic acid).

In addition to fragments and derivatives of hyaluronic acid, synthetic derivatives, i.e., semisynthetic derivatives may be used in the methods and compositions of the invention. Exemplary semisynthetic derivatives of hyaluronic acid are esters of hyaluronic acid with alcohols of the aliphatic, araliphatic, heterocyclic and cycloaliphatic series, designated "HYAFF," that are described in U.S. Pat. Nos. 4,851,521, 4,965,353, and 5,202,431, EP 0 341 745 and EP 0 216 453. The contents of each of the above-identified patents are expressly incorporated herein by reference.

The hyaluronan and/or chemotherapeutic agents may be administered orally, topically, or parenterally in dosage unit formulations containing conventional non-toxic pharmaceutically acceptable carriers, adjuvants, and vehicles. The term parenteral as used herein includes subcutaneous injections, aerosol, intravenous, intramuscular, intrathecal, intracranial, intrasternal injection or infusion techniques.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the active ingredient in admixture with non-toxic pharmaceutically acceptable excipients which are suitable for the manufacture of tablets. The pharmaceutical formulation can be administered intratumorally.

These excipients may be, for example, (1) inert diluents, such as calcium carbonate, lactose, calcium phosphate or sodium phosphate; (2) granulating and disintegrating agents, such as corn starch or alginic acid; binding agents, such as starch, gelatin or acacia; and lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The hyaluronan as well as the chemotherapeutic agents useful in the method of the invention can be administered, for in vivo application, parenterally by injection or by gradual perfusion over time independently or together. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

It is envisioned that the invention can be used to treat pathologies associated cell proliferative disorders, including, for example, neoplasms, cancers (eg., cancers of the breast, lung (e.g., small cell lung cancer and non small cell lung cancer), prostate, kidney, skin, neural, ovary, uterus, liver, pancreas, epithelial, gastric, colorectal, intestinal, excorine, endocrine, lymphatic, haematopoietic system or head and neck tissue), fibrotic disorders and the like. In some embodiments, the cancer is a solid tumor, e.g., renal, urothelial (e.g., bladder), testicular, colon, rectal, lung (e.g., small cell lung carcinoma), breast, liver, kidney, skin, neural (e.g., neuroendocrine), uteral, pancreatic (e.g., pancreatic duct), or gastric cancer.

The methods and compounds of the invention may also be used to treat other diseases associated with chemotherapeutic treatment such as neurodegenerative disorders, hormonal imbalance and the like. Therefore, the present invention encompasses methods for ameliorating a disorder associated with cell proliferation, neoplasms, cancers and the like, including treating a subject having the disorder, at the site of the disorder, with hyaluronan and a chemotherapeutic agent in an amount sufficient to inhibit or ameliorate the cell's proliferation or the disorder. Generally, the terms "treating", "treatment" and the like are used herein to mean affecting a subject, tissue or cell to obtain a desired pharmacologic and/or physiologic effect. The effect may be prophylactic in terms of completely or partially preventing a cell proliferative disorder or sign or symptom thereof, and/or may be therapeutic in terms of a partial or complete cure for a disorder and/or adverse effect attributable to, for example, aberrant cell proliferation. "Treating" as used herein covers any treatment of, or prevention of a cell proliferative disorder in a vertebrate, a mammal, particularly a human, and includes: (a) preventing the disorder from occurring in a subject that may be predisposed to the disorder, but has not yet been diagnosed as having it; (b) inhibiting the disorder, i. e., arresting its development; or (c) relieving or ameliorating the disorder, i.e., cause regression of the disorder.

The invention includes various pharmaceutical compositions useful for ameliorating cell proliferative disorder, including neoplasms, cancers and the like. The pharmaceutical compositions according to one embodiment of the invention are prepared by bringing hyaluronan, analogue, derivatives or salts thereof and one or more chemotherapeutic agents or combinations of hyaluronan and one or more chemotherapeutic agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, eg., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Hyaluronan together with a chemotherapeutic agent of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the hyaluronan compounds of the present invention are of the order of about 0.3 grams to about 5 grams per patient per day, more preferably about 1 to 3 grams per patient per day, e.g., 1.5 to 2 grams perpatient per day. The amount of hylauronan and/or chemotherapeutic agent that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the instant invention may form solvates with water or common organic solvents. Such solvates are encompassed within the scope of the invention.

The compounds of the present invention may additionally be combined with other compounds to provide an operative combination. It is intended to include any chemically compatible combination of chemotherapeutic agents, as long as the combination does not eliminate the activity of the hyaluronan of this invention.

The invention will now be further described by way of reference only to the following non-limiting examples. It should be understood, however, that the examples following are illustrative only, and should not be taken in any way as a restriction on the generality of the invention described above. In particular, while the invention is described in detail in relation to cancer, it will be clearly understood that the findings herein are not limited to treatment of cancer. For example, HA may be used for treatment of other conditions.

EXAMPLES

Example 1

Preparation of Hyaluronan and 5-Fluorouracil Solutions

HA used in all of the in vitro and in vivo studies were obtained from Kyowa Hakko Kogyo (Yamaguchi, Japan). 5-FU was obtained from Sigma, St. Louis, USA. And Adraimycin from cytomix, Northcote, Melbourne, Australia. A standard profile of the HA used is shown in Table 1.

TABLE 1

Specification Sheet For Hyaluronan Bulk Dried Powder

| TEST | SPECIFICATION |
|---|---|
| 1. Description | White or cream coloured powder or granules, odorless |
| 2. Identification (IR Spectrum) | Conforms to Reference Standard |
| 3. pH (1% solution) | 5.0 to 7.0 |
| 4. Loss on Drying | NMT 10.0% |
| 5. Residue on Ignition | 15.0 to 19.0% |
| 6. Protein Content | NMT 0.1% |
| 7. Heavy Metals | NMT 20 ppm |
| 8. Arsenic | NMT 2 ppm |
| 9. Sodium Hyaluronate Assay | 97.0-102.0% (dried basis) |
| 10. Intrinsic Viscosity | 10.0-14.5 dL/g |
| 11. Total Aerobic Microbial Count (USP 23) | NMT 50 CFU/gram |
| 12. *Staphylococcus aureus* (USE) 23) | Absent |
| 13. *Pseudomonas aeruginosa* (USP 23) | Absent |
| 14. Yeasts and Moulds (USP 23) | NMT 50 CFU/gram |
| 15. Bacterial Endotoxin (LAL)(USP23) | NMT 0.07 EU/mg |

A 10 mg/ml stock of HA solution was prepared by dissolving desiccated HA (modal $M_r$ 7.5×10$^5$ Da,) in pyrogen-free injection grade water. To ensure a homogenous solution the HA was dissolved overnight at 4° C. followed by thorough vortexing. To ensure that the HA had maintained its molecular weight during the preparation of the stock solution, the solution was analyzed on a Sephacryl S-1000 size exclusion gel with column specifications of 1.6 cm×70 cm, sample size 2 ml, flow rate 18 ml/h and 2 ml fraction size. Hyaluronan was detected in column fractions by the uronic acid assay.

The uronic acid assay was used to detect the presence of hyaluronan qualitatively from the fractions collected from the gel filtration chromatography procedure. A 25 µl aliquot of each fraction was then transferred into a 96 well plate. 250 µl of a carbazole reagent (3M carbazole/0.025M borate in $H_2SO_4$) was then added to these fractions. The 96 well plate was incubated for 45-60 min at 80° C. A Dynatech MR7000 plate reader with a 550 nm filter was used to read the 96 well plate. The absorbance was considered to be significant when it was >3 standard deviations above the background absorbance. The background was calculated by taking an equal number of sample points before and after $V_o$ and $V_t$ where the average number taken was 16 (Fraser et al. 1998).

A stock solution of 5-FU was prepared by dissolving powdered 5-FU in 0.1M NaOH (pH 8.9) and brought to a concentration of 1 mg/ml with pyrogen-free injection grade 0.9% w/v NaCl. The stock solution was filtered through a 0.22 µm filter to ensure sterility. The 5-FU was diluted by adding the required volume of stock solution to the cell-line specific growth medium as specified above.

A 10 mg/ml solution of adriamycin in 0.9% NaCl was obtained from Cytomix.

Example 2

Testing the Effect of Hyaluronan on Cancer Cell Morphology

Human breast adenocarcinoma cell lines MDA-MB-468, MDA-MB-435 and MDA-MB-231 were selected based on HA binding affinity (Culty et al, 1994), and the expression of the HA receptors of CD44 and RHAMM (Wang et al, 1996). The characteristics of these cell lines are shown in Table 2.

TABLE 2

Hyaluronan Binding And Receptor Expression Of Human Mammary Carcinoma Cell Lines

| Cell Line | Type of breast cancer | Degree of HA Binding[a] | HA Receptor Expression[b] | |
|---|---|---|---|---|
| | | | CD44 | RHAMM |
| MDA-MB-231 | adenocarcinoma | ++ | +++ | +++ |
| MDA-MB-468 | adenocarcinoma | ++++ | ++++ | ++ |
| MDA-MB-435 | ductal carcinoma | + | +++ | ND |

[a]Culty et al, 1994
[b]Wang et al, 1996

Cell lines MDA-MB-468, MDA-MB-435 and MDA-MB-231 were routinely grown and subcultured as a monolayer in 175 cm$^2$ culture flasks in Leibovitz L-15 Medium supplemented with 10% Foetal calf serum (FCS) and antibiotic/antimycotic reagents at 37° C. in humidity controlled incubator with 100% (v/v) air.

Leibovitz-L-15 with glutamine (10× concentrate), RPMI (10× concentrate), Eagles basal medium (EBM, 10× concentrate), 20 mM HEPES, 0.09% w/v bicarbonate, Hanks' Balanced Salt Solution (HESS, 10× concentrate) and Dulbecco's Phosphate Buffered Saline without calcium and magnesium (PBS, 10× concentrate) were purchased from Sigma (St Louis, Mo., USA). Powder concentrates were dissolved in the required volume of reverse osmosis deionised pyrogen-free distilled water to make a single strength solution, sterilized by 0.22 µm high pressure filtration (Millipore Corporation, MA. U.S.A.), and stored at 4° C. FCS) were purchased from the CSL Ltd., Australia. FCS was stored at −20° C. Antibiotic/antimycotic solution (100×concentrate) containing 10,000 units penicillin, 10 mg streptomycin and 25 µg amphotericin U/ml was obtained from, Sigma (St Louis, USA). Trypsin/EDTA solution (10× concentrate) containing 5 g porcine trypsin and 2 g EDTA/L in 0.9% w/v sodium chloride was obtained from Sigma (St Louis, Mo., USA). All breast cancer cell lines were purchased from American tissue culture collection (Rockville, USA). All plastic disposable culture vessels were purchased from Greiner (Austria). Eight-welled, tissue culture microscope slides were obtained from Linbro (Flow Laboratories, VA, USA).

For the tests, MDA MB-468, MDA MB-231 and MDA MB-435 cell line were grown in 90% Leibovitz L-15 medium supplemented with 10% FCS. When confluent the cultures were washed 1× in HBSS and trypsinised in 0.25% trypsin/0.05% EDTA. The cell suspensions were counted with an automated cell counter (ZM-2 Coulter Counter) by adding 15 mL saline+0.2 ml of cell suspension.

Cells were resuspended to a number of:
MDA MB-468: 25,000 cell/ml of media
MDA MB-231: 12,000 cell/ml of media
MDA MB-435: 12,000 cell/ml of media The cells were plated into 48-well plates (1 cm$^2$ surface area) by adding 1 ml of cell suspension per well.

Cells were allowed to attach for 24 h, before the media was removed, monolayers washed. The test media was; growth media containing 0-1 µM adriamycin or 5-fluorouracil with or without the addition of 0-1 µM of HA (modal Mw 750,000).

The cells were exposed to the several combinations of HA and drugs for different times and at different concentrations (Table 3).

TABLE 3

Incubation Conditions for Hyaluronan and Drugs with Human Breast Cancer Cells

| Sequence of HA/Drug Addition | HA Incubation | Drug Incubation | Growth Time |
|---|---|---|---|
| 0-1 µM HA, media wash, 0-1 µM drug, media wash, grow drug-free | 30 min | 1 h | 1 day |
| 0-1 µM HA, media wash, 0-1 µM drug, media wash, grow drug-free | 1 h | 1 h | 1 day |
| 0-1 µM HA, media wash, 0-1 µM drug, media wash, grow drug-free | 24 h | 1 h | 1 day |
| 0-1 µM HA, media wash, 0-1 µM drug, media wash, grow drug-free | 24 h | 24 | 1 day |
| 0-1 µM HA, media wash, 0-1 µM drug,. media wash, grow drug-free | 30 min | 1 h | 3 day |
| 0-1RM HA, media wash, 0-1 µM drug, media wash, grow drug-free | 1 h | 1 h | 3 day |
| 0-1 µM HA, media wash, 0-1 µM drug, media wash, grow drug-free | 24 h | 1 h | 3 day |
| 0-1 µM HA, media wash, 0-1 µM drug, media wash, grow drug-free | 24 h | 24 | 3 day |
| 0-1 µM drug/100 nM HA | | 30 min | 1 day |
| 0-1 µM drug/100 nM HA | | 1 h | 1 day |
| 0-1 µM drug/100 nM HA | | 24 | 1 day |
| 0-1 µM drug/100 nM HA | | 30 min | 3 days |
| 0-1 µM drug/100 nM HA | | 1 h | 3 days |
| 0-1 µM drug/100 nM HA | | 24 | 3 days |
| 0-1 µM HA | 30 min | | 1 day |
| 0-1 µM HA | 1 h | | 1 day |
| 0-1 µM HA | 24 | | 1 day |
| 0-1 µM HA | 30 min | | 3 days |
| 0-1 µM HA | 1 h | | 3 days |
| 0-1 µM HA | 24 | | 3 days |
| 0-1 µM HA | 3 days | | 3 days |

After the incubation and growth periods the cell monolayers were washed with HBSS and trypsinised in 0.25% trypsin/0.05% EDTA. The cell suspensions were counted with an automated cell counter (ZM-2 Coulter Counter) by adding 15 mL saline+0.2 ml of cell suspension. Results were expressed as % of no drug control which was calculated as:

$$\frac{\text{Cell Count} \times 100}{\text{Cells in No Drug Control}}$$

Or depending on the experiment as % of drug control, calculated as:

$$\frac{\text{Cell Count} \times 100}{\text{Controls in Drug Control}}$$

Exponentially growing human breast cancer cells MDA MB 231 as described in example 2 were incubated with 0-5 mg/ml HA (modal Mr 750,000 D) for 24 h. At 24 h the cells were counted and photographed with CPR, 1600 film rolls from Eastman Kodak Company, Rochester, USA.

When HA was incubated with breast cancer cells for 30 min, 1 h, 24 h or 3 days a varied response was observed, where the reduction in breast cancer cell number ranged from 0-29% (See Table 4).

TABLE 4

Cytotoxic Effect of HA on Human Breast Cancer Cell Lines

| Exposure Time | Cell Line MDA-MB | Cell Line MDA-MB 231 | Cell Line MDA-MB 435 |
|---|---|---|---|
| 3 days 100 nM | −29% | −23% | −22% |
| 1 h 100 nM | +3% | −21% | −4% |
| 30 min 100 nM | −5% | −27% | −12% |
| 30 min 500 nM | −22% |  | 0 |
| 30 min 1000 nM | +2% | −26% | ND |
| 24 h 100 nM | −5% | −8% | −12% |

*Figures are the mean of 2–3 separate determinations

When human breast cancer cells were incubated with HA specific morphological changes (See FIG. 1) were also observed such as swelling of the plasma membrane, greater granularity of cytosolic components.

When human breast cancer cells were exposed to HA for 30 min, 1 h, 24 h or 3 days followed by exposure toadriamycin, it became evident that HA enhanced the cytotoxicity of the drug (FIG. 3 & Table 5).

TABLE 5

Effect of HA on Adriamycin Cytotoxicity in Breast Cancer Cell Lines

| Treatment | $IC_{50}$ MDA-MB 468 | $IC_{50}$ MDA-MB 231 | $IC_{50}$ MDA-MB 435 |
|---|---|---|---|
| 3 day drug exposure | 3 to 12 | 4 to 5 | 10 |
| 1 h drug/HA, 3 days drug-free | 40 | 2 to 8 | 0 |
| 1 h drug, 3 days drug-free | 20 to 40 | 3 to 9 | 6 to 10 |
| 30 min 100 nm HA, 1 hr drug, 3 days drug-free | 2 to 20 | 2 to 6 | 4 to 40 |
| 30 min 100 nM HA, 3 day drug exposure | 3 to 18 | 2 to 4 | 2 to 8 |
| 30 min 500 nM HA, 3 day drug exposure | 3 to 9 | 2 to 8 | 2 to 4 |
| 30 min 1000 nM HA, 3 day drug exposure | 1 to 10 | 2 to 8 | 1 to 5 |
| 24 h 100 nM HA, 3 day drug exposure | 8 to 12 | 13 | 24 |
| 24 h 100 nM HA, 1 h drug exposure, drug-free 3 days | 50 to 60 | 9 | 21 |

All figures represent the range of 2-3 separate experiments, where the numerical values are the multiplication factor decrease in $IC_{50}$ which is exerted by the addition of HA to drug or pre-sensitization of cancer cells with HA before the addition of drug.

Example 3

Efficacy of Hyaluronan In Vivo

Based on the results from the in vitro drug sensitivity experiments in Example 2, evaluation of the treatment efficacy of hyaluronan as a sole agent, and as a chemosensitizer in the treatment human breast carcinomas in vivo was undertaken.

From the results in Example 2 the carcinoma cell line MDA-MB-468 was selected as the cancer cell inoculant for the generation of any nude mouse human tumour xenografts. Cells were routinely grown and subcultured as a previously described in Example 2. For injection into mice, cells were grown to 100% confluency, trypsinised in 0.025% trypsin/0.01% EDTA solution, washed twice by centrifugation in a Beckman TJ-6 bench centrifuge at 400 $g_{av}$ for 10 min, counted using a Model-ZM Coulter counter and resuspended in serum-free Leibovitz L-15 medium at $1 \times 10^8$ cells/ml.

Six to eight weeks old athymic CBA/WEHI nude female mice, purchased from the Walter and Eliza Hall Research Institute, Melbourne Australia, were maintained under specific pathogen-free conditions, with sterilized food and water available ad libitum. Each mouse received one injection containing $5 \times 10^6$ cells in 50 μl. The cells were injected with a 26 gauge needle into the mammary fat pad directly under the first nipple (Lamszus et al, 1997). Tumour measurements were made weekly by measuring three perpendicular diameters $(d_1 d_2 d_3)$. Tumour volume was estimated using the formula:

$$(1/6)\pi(d_1 d_2 d_3)$$

Treatment with 5-FU±HA was commenced approximately 4-8 weeks after the cancer cell inoculation. The mean tumour size for mice used in each study is summarized in Table 6.

TABLE 6

Summary of Human Breast Cancer Tumours at Commencement of Each Study

| Study | Tumor volume (mean ± SEM) | Tumour as % of net body mass (mean ± SEM) |
|---|---|---|
| Efficacy: 6-week | 0.37 ± 0.20 mm³ | 0.19 ± 0.10 mm³ |

Approximately 8 weeks after tumour induction two tumour-bearing mice were given a lethal dose of Nembutal.

Within 3 min of killing the mice, tumours were surgically removed and immediately fixed in 10% buffered formalin for 12 h. The fixed tumour was dehydrated overnight in a series of 70-100% ethanol, followed by paraffin embedding from which 2-4 μm sections were cut. The sections were placed on slides, de-waxed, and brought to water. Slides were washed 3×5 min in PBS. Heterophile proteins were blocked by incubation with 10% foetal calf serum for 10 min, followed by a PBS rinse.

Secondary antibodies used in the visualization of HA and HA synthase antibodies were purchased from Dako (California, U.S.A.). 3,3'-Diaminobenzidine (Sigma Fast DAB) tablets were obtained from Sigma, St. Louis, USA.

The detection antibodies were applied for 60 min at RT. The detection antisera or antibodies were against RHAMM, CD44H and CAE. The slides were washed 3×5 min in PBS and endogenous peroxidase activity blocked by immersion in 0.3% $H_2O_2$ in methanol for 20 min. Following a further PBS wash, the peroxidase-conjugated swine anti-rabbit secondary antiserum was applied for 60 min at RT, followed by 3×5 min washes in PBS. Sigma Fast 3,3'-Diaminobenzidine tablets (DAB) were prepared according to the manufacturer's instructions and the DAB solution was applied for 5-10 min at RT. The slides were washed in tap water for 10 min, counterstained with haematoxylin, dehydrated and mounted.

Individual injections of 5-FU were prepared according to individual mouse masses, with the aim of delivering 30 mg/kg 5-FU in 50 μl (equivalent to human therapeutic dose of 10.5 mg/kg for a mean body weight of 60 kg; Inaba et al, 1988). HA injection comprising a final HA concentration equivalent to 12.5 mg/kg of mouse mass were prepared so that deliver of 12.5 mg/kg HA in 50 μl could be effected. With this quantity of HA injected into the body, saturation kinetics would be observed for the period of the experimentation (Fraser et al, 1983).

One of the most commonly used treatment regimens for human breast cancer is cyclophosphamide, methotrexate and 5-fluorouacil, which is administered on day 1 and 8 of a 28 day cycle. In human breast cancer the initial treatment regimen is for 6 cycles at which time the patient condition is re-assessed, therefore we tried to simulate the human treatment regimen as closely as possible by exposing the mice to 6 cycles (6 months) of treatment in a long term efficacy study and a 6 cycles (6 week) short term efficacy study. Considering the life cycle of a mouse is approximately 2 years we commenced both short-term and long-term treatment protocols (see Table 7).

TABLE 7

Treatment Administration Protocols.

| Treatment Group | Dosage | 6-Week Study Treatment Regimen Bolus injection on Days |
|---|---|---|
| 1. Saline | 0.1 ml of 0.9% saline (injection grade) | 1 & 2 of 7 day cycle |
| 2. HA | 0.1 ml containing: 12.5 mg/kg HA | 1 & 2 of 7 day cycle |
| 3. 5-FU | 0.1 ml containing: 30 mg/kg 5-FU | 1 & 2 of 7 day cycle |
| 4. HA followed by 5-FU | 0.1 ml containing: 12.5 mg/kg HA or 30 mg/kg 5-FU | 1: HA<br>2: 5-FU<br>3: HA<br>4: 5-FU<br>of 7 day cycle |
| 5. HA | 0.1 ml containing: 12.5 mg/kg HA | 1: HA<br>3: HA<br>of 7 day cycle |
| 6. 5-FU | 0.1 ml containing: 30 mg/kg 5-FU | 2: HA<br>4: HA<br>of 7 day cycle |

Mice were randomly divided into 7 groups of 8 animals per group for the short term study and 5 groups of 8 animals for the long term study (refer to Table 7 for dosage and treatment administration schedule).

The treatment was not extended over the 6 month regimen since it has been demonstrated that chemotherapy lasting more than six months has not generally been associated with greater benefit (Harris et al, 1992).

Animals were weighed and tumour volumes measured on the day of treatment application for long term study. In the 6-week study animals were weighed and tumour volumes measured on a daily basis. Animals were individually placed in an injection box, and the injections were administered via the tail vein. It has been experimentally proven that stress can be a major factor in a patients response to chemotherapy (Shackney et al, 1978), therefore we ensured that equal numbers of mice were allocated to each cage, the animal number per cage varied from 5-8 depending on the stage of experimentation.

The experimental end-point occurred when the animal had to be euthanised due to degree of disease progression or when the 6 month (long term) or 6 week (short term) treatment regimen was completed. Due to the animal ethics guidelines the animals were monitored fortnightly by an independent animal ethics officer who assessed the degree of disease progression. The following criteria were used to determine if an animal had reached the stage of experimental end-point of necessary death:

1). Tumour mass was so large the animal was immobilized;
2). Animal was not eating or drinking and had experienced dramatic weight loss; or
3). Tumour size was greater than 10% of body mass.

At the experimental end-point the animals were anaesthetized by a 0.1 ml intraperitoneal injection of Nembutal (60 mg/ml), blood was collected followed by killing of the animals using cervical dislocation.

Immediately after killing the mouse the tumour, liver, heart, spleen, bladder, left and right kidneys, uterus, lungs, stomach, intestines, brain and lymph nodes were excised and placed in 4% formalin buffered with 0.06M phosphate pH 7.5, and cetylpyridinium chloride, 1.0% w/v. The tissue was fixed for 16-24 h before histological processing. Fixed tissue was dehydrated stepwise to 100% ethanol and embedded in paraffin blocks from which 2-4 μm sections were placed on glass microscope slides. Staining the tissue sections with a haematoxylin nuclear stain and eosin cytoplasmic stain highlighted any pathological features that could indicate treatment toxicity.

Nine to 11 lymph nodes were collected per animal, ensuring that all nodes which drained the tumour area were collected. There are currently two methods used for the detection of lymph node metastasis
i) routine haematoxylin and eosin staining of gross organ structure; and ii) immunohistochemistry using a cancer marker 20 such as carcinoembryonic antigen.

Both methods of metastasis detection were employed in this study. Not all commercially available CEA antibodies react with human breast cancer cells, so we tested the reactivity of 5 different antibodies (DAKO, Amersham and KPL).

The haematoxylin and eosin stained lymph nodes were examined by Dr P. Allen (certified pathologist) where each node was microscopically examined for the presence of tumour cells. The CEA immunostained lymph nodes were microscopically examined, where any positively stained nodes were counted and considered positive for lymph node metastasis.

Tumour volume was monitored on a daily or weekly basis by caliper measurements and tumour volume calculated as previously described. At the end of the 6 week study, tumour mass was determined where the HA chemosensitizing therapy had significantly smaller tumours than the saline group, HA and 5-FU groups (p=0.005) as see in FIG. 5. No significant differences in tumour response were noted in the initial 2 weeks of treatment, but thereafter the HA followed by 5-FU tumour growth was retarded in comparison to the other treatment groups. During the 6 weeks of treatment interesting differences were noted in the number of tumour doubling cycles. Mice receiving the saline treatment underwent an average of 4 tumour doublings, while the incorporation of HA into the treatment regimen significantly increased the tumour doubling time where HA/5-FU animals underwent an average of one tumour doubling cycle, once again highlighting the effect of HA on 5-FU cytotoxicity.

All animals displayed lymph node metastasis in lymph nodes that were adjacent to the primary tumour. The percentage of lymph node involvement (number of metastatic nodes per animal) was greatly reduced by the HA followed by 5-FU, 5-FU and HA treatment, where the saline group demonstrated a 6-fold increase in the amount of lymph node involvement. The other treatment groups demonstrated a significantly smaller percentage at 12.2-14.3% (Dunnett's Multiple Comparison Test, p=<0.001).

The co-administration of HA resulted in a significant reduction in non-lymphoid metastasis. With the exception of the mice receiving the HA therapy, new tumours were observed around the neck or underarm region of the area adjacent to the primary tumour.

Gastro-Intestinal Tract Toxicity:

One of the most common toxic effects of 5-FU is on the gastro-intestinal tract where haemorrhagic enteritis and intestinal perforation can occur (Martindale, 1993). Animals were monitored daily for GI tract upset such as diarrhea and weekly for more severe toxicity manifestations such as weight loss. Weight loss was monitored by calculating net body weight as estimated by subtracting tumour weight, which was calculated as 1 g×tumor volume (cm$^3$) as cited in Shibamoto et al, 1996. For demonstration of any weight changes the animal body weight was normalized to the body weight at the time of treatment commencement as Body Mass (Ex Tumour)—Body Mass at Commencement of Treatment (Ex Tumour)

Body Mass at Commencement of Treatment (Ex Tumour)× 100

Figure 4:
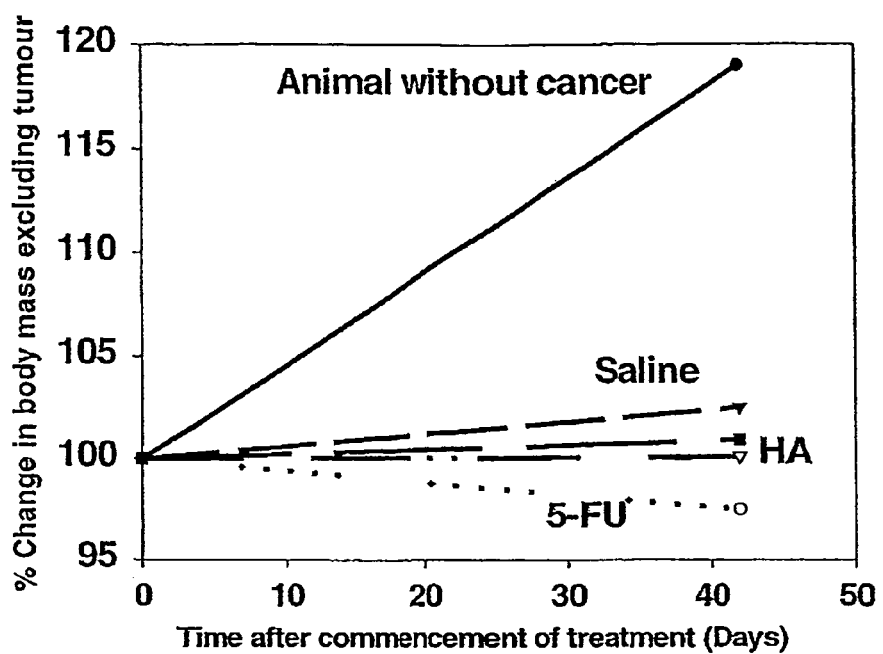
FIG. 4 shows that there was no treatment toxicity noted throughout the 6-week study. In comparison to the 5-FU treatment group the mice receiving HA therapy, that is as a sole agent or as a chemosensitizer, demonstrated enhanced well being where the animal did not loose weight, but maintained its body mass.

No treatment toxicity was noted throughout the 6-week study. In comparison to the 5-FU treatment group the mice receiving HA therapy, that is as a sole agent or as a chemosensitizer, demonstrated enhanced well being where the animal did not loose weight, but maintained its body mass (FIG. 4).

Blood Marrow Suppression

As one of the major toxicities associated with 5-FU treatment is depression of the bone marrow and subsequent drop in white blood cells it was necessary to assess any treatment associated blood toxicity. Upon anaesthetizing the animals, blood was collected from the heart or great vessels using a needle and syringe. Estimation of white blood cell number by making a 1/50 dilution of blood in mouse tenacity saline (M) and counting it on a haemocytometer. A differential blood count was performed by counting-neutrophils, lymphocytes, and erythrocytes. The total estimation of blood cell sub-populations was compared to published data for mouse blood.

The total white cell count and sub-population differential were not significantly different, regardless of the treatment.

Effect of Treatment on Organ Mass

To ensure that treatments did not induce organ atrophy or enlargement, the organs were removed and weighed during the post mortem. The mass of each organ was calculated as a % of the overall net body weight, and compared to the organ masses of the saline only group (Group 1).

The overall patient survival time was calculated as the time (days or weeks) that the animal lived after the commencement of treatment. All animals in each treatment group completed the 6-week treatment program.

In relation to organ mass, the HA therapy did not result in any dramatic toxicity. Mice receiving 5-FU exhibited an enlarged spleen (61% increase in mass), while the co-administration of HA and 5-FU significantly counteracted this enlargement by 31% (student t-test, p<0.001). The 5-FU therapy resulted in a shrinkage of the uterus (22%), once again the HA/5-FU therapy reduced this toxic effect by 10% (student t-test, p=0.04). It was also clearly defined that the addition of HA to the treatment regimen, when co-administered or administered the day before, significantly decreased the primary tumour mass in comparison to the saline treatment group (student t-test, p=0.006). No other differences in organ mass were noted between treatments.

Example 4

Effect of Hyaluronan Concentration on the In Vitro Efficacy of 5-FU

MDA-MB 468, MDA-MB 435 and MDA-MB 231 cells were cultured as described in Example 2. When the cultures had reached 70-80% confluency they were washed in 1×HBSS at 37° C. and trypsinised in 10 ml of 0.25% trypsin/0.05% EDTA until cells have fully detached. After add 1 ml of FCS to neutralize trypsin the cells were counted, centrifuged at 1,200 rpm for 5 min and resuspended as follows:
MDA-MB 231: 12,000 cells/ml of media;
MDA-MB 468: 25,000 cells/ml of media; and
MDA-MB 435: 12,000 cells/ml of media.

Cells were then plated into 48-well plates and incubated in accordance with suppliers' instructions. After 24 h media was removed and replaced with the following test media:
MDA-MB 468: 40 nM adriamycin;
MDA-MB 231: 50 nM adriamycin; and
MDA-MB 435: 10 nM adriamycin
40 nM Adriamycin media:450 ml (Stock adriamycin is 1.7 mM, therefore 1,700,000/40=42,500; 450,000/42500=10.6 ul of 1.7 mM Adriamycin+450 ml Media).
Stock HA was 700,000 daltons at 14.3 µM HA

CONCLUSIONS

Figure 5:
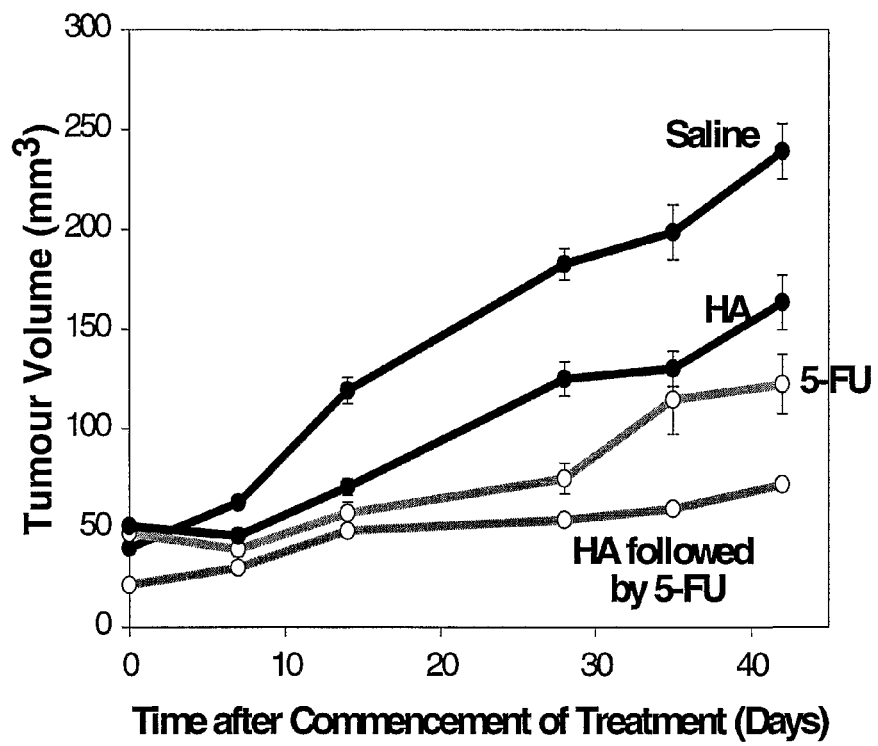
FIG. 5 shows that at the end of the 6 week study, tumour mass was determined where the HA chemosensitizing therapy had significantly smaller tumours than the saline group, HA and 5-FU groups (p=0.005). HA as a sole agent also demonstrated its effect by reducing the primary tumour mass in comparison to the saline control. No significant differences in tumour response were noted in the initial 2 weeks of treatment, but thereafter the HA followed by 5-FU tumour growth was retarded in comparison to the other treatment groups. During the 6 weeks of treatment interesting differences were noted in the number of tumour doubling cycles. Mice receiving the saline treatment underwent an average of 4 tumour doublings, while the incorporation of HA into the treatment regimen significantly increased the tumour doubling time where HA/5-FU animals underwent an average of one tumour doubling cycle, once again highlighting the effect of HA on 5-FU cytotoxicity.
Figure 6:
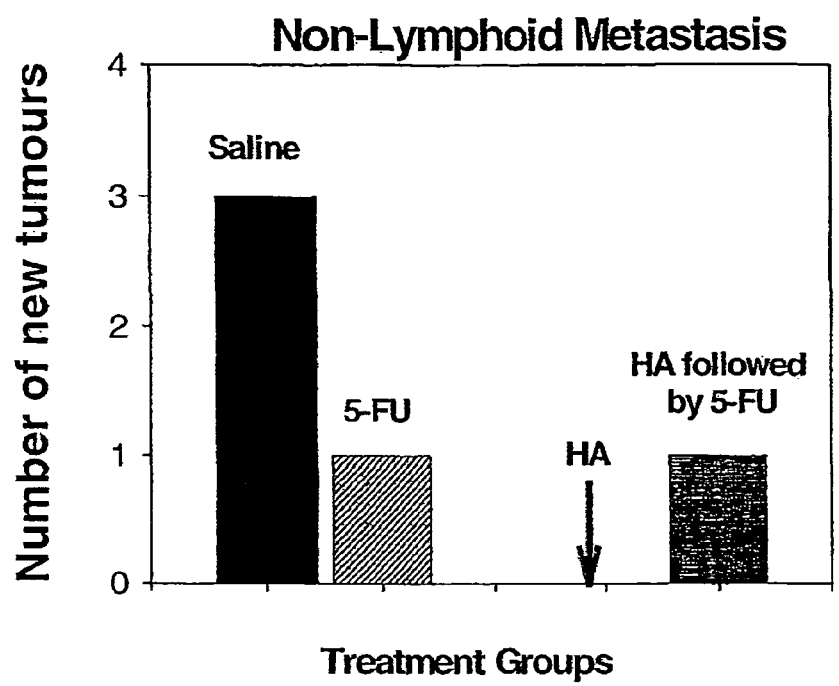
FIG. 6 shows that the co-administration of HA resulted in a significant reduction in non-lymphoid metastasis. With the exception of the mice receiving the HA therapy, new tumours were observed around the neck or underarm region of the area adjacent to the primary tumor.

This study has definitively proven that HA, can enhance the cytotoxicity of anti-cancer drugs, 5-FU and Adriamycin, both in vitro and in vivo. More specifically:

1). As a sole agent HA can exert a cytotoxic effect on cancer cells both in vitro and in vivo (FIG. 5);

2). Evaluation of the therapeutic efficacy of HA sole therapy or chemosensitizing therapy demonstrated that it was not toxic to normal tissue and it did not enhance the toxicity profile of the drug. In fact, mice receiving the therapy displayed a significant weight gain over the 6-week treatment period and a reduction in lymph node metastasis. The co-administration of HA and 5-FU had a dramatic effect on the reduction of the primary tumour volume; and 3). Mice who had HA incorporated into the treatment regimen did not display the formation of any secondary tumour (FIG. 6).

Future Studies

Experiments are presently being conducted on the use of HA for in vivo treatment of breast cancer. These experiments are focusing on the effect of HA concentration and molecular weight and on the cytotoxicity of adriamycin. It is the aim of these studies to also establishing drug and HA exposure time and regimens, as well as the mechanism of action of HA, i.e.: receptor mediated transport and/or effect on cell membrane. Further data on the role of HA in chemosensitizing drug-resistant cancer cells will also be collected.

Section 1:

All studies will be conducted on breast cancer cell lines that express differing levels of HA receptors, CD 44 and RHAMM. Cell lines to be tested, MDA-MB 435, MDA-MB 231, MDA-MB 468, ZRL-751 and several MDR-1 expressing breast cancer cell lines.

Investigation of the effect of HA/adriamycin exposure times and concentration on drug-resistant and drug-sensitive breast cancer cells. Four MDR-1 positive and 4 MDR-1 negative cell lines will be exposed to adriamycin at 1, 2.5, 5, 10, 20, 40, 60, 80 and 100 nM, the following variables will be tested:

1). 1 h drug±100 nM HA exposure followed by 3 days of drug-free growth;

2). Constant drug exposure±100 nM HA for 3 days 30 min 100 nM HA exposure, followed by drug for 1 h, cells grown drug-free for 3 days; and 3). 24 h 100 nM HA exposure, followed by drug for 1 h, cells grown drug-free for 3 days.

These experiments will establish; optimal HA exposure times and regimens, magnitude of increased adriamycin cytotoxicity when combined with HA and whether HA can overcome efflux pump resistance in breast cancer cells.

To date the $IC_{50}$ of adriamycin has been determined as 90 nM. Using 90 nM of adriamycin the HA (700 kD) concentration will be varied to 1, 3, 10, 30, 100, 300 nM, 1 µM, 3 µM, 10 µM, 30 µM and 100 µM. The incubation variables to be tested are:

1). 30 min HA exposure followed by 1 h drug exposure cells grown drug-free for 3 days;

2). 24 HA exposure followed by 1 h drug exposure cells grown drug-free for 3 days; and 3). HA±drug exposure for 1 hr, cells grown drug-free for 3 days.

Any detached cells will be tested for cell viability since it has been suggested that HA can play a pivotal role in cancer cell detachment and migration. If detached cells are viable the HA receptor status will be determined using FACS surface epitope identification. Similar experiments will be performed with short HA oligiosaccharides, ie: 4 sacc, 6 sacc, 12 sacc, 5600 Da, 50,000 Da, 100,000 Da, 250,000 Da.

These experiments will demonstrate the optimal HA:drug ratio in vitro, optimal HA exposure time and regimen, effect of HA molecular weight on adriamycin cytotoxicity.

After determining the optimal HA concentration, the $IC_{50}$ of adriamycin will be used in a series of time i course experiments to observe any effect of HA on adriamycin metabolism.

The [$^{14}$C] adriamycin will be exposed to the cells for 30 min, 1 h, 2 h, 4 h, 8 h, 16 h and 24 h. The experimental conditions will be:

1). Exposure of cells to HA for 30 min followed by drug; and

2). Exposure of cells to HA for 24 followed by drug Co-exposure of HA/adriamycin.

Cells will be removed, hypotonically lysed and centrifuged at 113,000 gav for 1 hr. The membrane pellet and supernatant will be counted and analyzed for metabolites using HPLC.

Cells will also be grown on coverslips, where they will be exposed to adriamycin±HA (exposures regimen as above) and a confocal photography time course will be used to track the cytosolic uptake and movement of the drug.

Identification of HA Receptors on MDR-1 positive and negative breast cancer cell lines, FACS quantitation of the CD44s, CD44v6, CD44v10 and RHAMM receptors will be conducted. Quantitation of the HA/receptor binding and saturation kinetics using FITC/HA and FACS analysis will also be done.

By exposing the cells to:

1). HA for 30 min followed by drug;

2). HA for 24 h followed by drug; and

3). HA/adriamycin

We will be able to determine any of these block CD44s and RHAMM receptors. The receptor status of any viable cells will be quantitated using surface epitope FACS analysis. If blocking of the HA receptors decreases the normally observed synergism between adriamycin and HA, the membrane bound and cytosolic adriamycin will be quantited t HA receptor blocking.

HA degradation by cell lines using [$^3$H]HA and gel filtration chromatography±receptor blocking will be studied.

HA of molecular weight, 4 sacc, 6 sacc, 12 sacc, 5600 Da, 50,000 Da, 100,000 Da, 250,000 Da, 750,000 Da and 1,500,000 Da will be incubated with breast cancer cell lines at pre-determined "observed-effect" concentrations and the following will be parameters investigated: Extracellular and intracellular calcium flux (cellular probe assays). Regulation of cytoskeletal components (micro-array of cytoskeletal genes), effect on volume of cells (Coulter size Analysis) and mobility of cancer cells (Boyden Chamber matrigel assays) will also be conducted.

The effect of HA on the cell cycle will be undertaken by incubating HA of molecular weight, 4 sacc, 6 sacc, 12 sacc, 5600 Da, 50,000 Da, 100,000 Da, 250,000 Da, 750,000 Da and 1,500,000 Da with breast cancer cell lines at pre-determined "observed-effect" concentrations. Cells will be labeled with potassium iodide and subjected to FACS analysis. The number of cells in each stage of the cell cycle will be determined.

Comparisons of the in vitro efficacy of the liposomal Doxorubicin and HA/Doxorubicin preparations will be conducted using the optimal HA/Doxorubicin preparation and the dosage range used by the Liposome Company in the pre-clinical testing of the liposomal doxorubicin.

Section 2:

Before progression of the HA/adriamycin anti-cancer therapy into Phase I human breast cancer trials it is necessary to conduct preliminary toxicity experiments.

The experiments will focus on:

1). Effect of hyaluronan on adriamycin uptake in mouse body organs and fluids;

2). Establish a preliminary dose range for adriamycin Determine if HA targets adriamycin to human breast tumour xenografts in nude mice;
3). Compare the commercial liposomal Doxorubicin to HA/doxorubicin uptake in mice; and
4). Comparison of short-term efficacy of liposomal doxorubicin and HA/doxorubicin.

From Inaba et al, (1988) the dose of adriamycin in nude mice was 4 mg/kg which is a human equivalent dose of 60 mg/m$^2$. Nude mice bearing human tumours will be injected with adraimycin±HA. Using adraimycin concentrations of 4 mg/kg±12.5 mg/kg HA. The experimental protocol will include the following treatment groups:
1). 4 mg/kg adriamycin;
2). 4 mg/kg adriamycin+12.5 mg/kg HA; and
3). 4 mg/kg liposomal doxorubicin.

Using adriamycin±HA will be quantitatively injected into the tail vein of the mouse.

At the time intervals of 2, 15, 30, 60 min and 1.5, 2, 4, 8, 24 and 48 h (4 animals/time point) the mice will be killed by a 0.1 ml IP injection of Nembutal. All body organs, skeletal muscle, lymph nodes, bone marrow, urine and blood will be removed and the adriamycin content determined using HPLC and fluorescence.

Human breast tumours will be generated in nude mice (WEHI CBA strain). The mice will be injected with:
1). Mouse LD$_{50}$ is 10 mg/kg;
2). 4 mg/kg adriamycin;
3). 4 mg/kg adriamycin+12.5 mg/kg HA;
3). 8 mg/kg adriamycin;
4). 8 mg/kg adriamycin+12.5 mg/kg HA;
5). 4 mg/kg liposomal doxorubicin;
6). Saline; and
7). 12.5 mg/kg HA.

The above mentioned will be quantitatively injected into the tail vein of the mouse (8 animals/group) on Days 2, 4, 6 of a weekly cycle.

Tumour volume, body mass, food intake and functionality of the mice will be monitored on a daily basis.

At the completion of the 8-week study the mice will be killed by a 0.1 ml IP injection of Nembutal. All body organs, tumour, skeletal muscle, lymph nodes, bone marrow, urine and blood will be removed processed for pathological assessment.

Section 3:

To answer some basic questions about the effect of HA anti-cancer therapy on colon cancer cells the following experiments should be conducted.

Investigation of the effect of HA/5-FU exposure times and concentration on drug-resistant and drug-sensitive colon cancer cells.

Three resistant and 3 sensitive cell lines will be exposed to 5-FU at 1, 2.5, 5, 10, 20, 40, 60, 80 and 100 nM, the following variables will be tested:
1). 1 h drug±100 nM HA exposure followed by 3 days of drug-free growth;
2). Constant drug exposure±100 nM HA for 3 days;
3). 30 min 100 nM HA exposure, followed by drug for 1 h, cells grown drug-free for 3 days; and
4). 24 h 100 nM HA exposure, followed by drug for 1 h, cells grown drug-free for 3 days.

Using the IC$_{50}$ of 5-FU as determined as above, HA (700 kD) concentration will be varied to 1, 3, 10, 30, 100, 300 nM, 1 μM, 3 μM, 10 μM, 30 μM and 100 μM. The incubation variables to be tested:
1). 30 min HA exposure followed by 1 h drug exposure cells grown drug-free for 3 days;
2). 24 HA exposure followed by 1 h drug exposure cells grown drug-free for 3 days; and
3). HA±drug exposure for 1 hr, cells grown drug-free for 3 days.

Any detached cells will be tested for cell viability since it has been suggested that HA can play a pivotal role in cancer cell detachment and migration. If detached cells are viable the HA receptor status will be determined using FACS surface epitope identification.

Similar experiments will be performed with short HA oligiosaccharides, ie: 4 sacc, 6 sacc, 12 sacc, 5600 Da, 50,000 Da, 100,000 Da, 250,000 Da.

After determining the optimal HA concentration, the IC$_{50}$ of 5-FU will be used in a series of time course experiments to observe any effect of HA on adriamycin metabolism.

The [$^3$H] 5-FU will be exposed to the cells for 30 min, 1 h, 2 h, 4 h, 8 h, 16 h and 24 h. The experimental conditions will be:
1). Exposure of cells to HA for 30 min followed by drug; and
20. Exposure of cells to HA for 24 followed by drug Co-exposure of HA/5-FU.

Cells will be removed, hypotonically lysed and centrifuged at 113,000 gav for 1 hr. The membrane pellet and supernatant will be counted and analyzed for metabolites using HPLC.

Cells will also be grown on coverslips, where they will be exposed to 5-FU±HA (exposures regimen as above) and a confocal photography time course will be used to track the cytosolic uptake and movement of the drug.

Identification of HA Receptors on resistant and sensitive colon cancer cell lines, FACS quantitation of the CD44s, CD44v6, CD44v10 and RHAMM receptors, Quantitation of HA/receptor binding and saturation kinetics using FITC/HA and FACS analysis will be done.

Blocking of CD44s and RHAMM receptors with inhibitory antibodies, apply 5-FU±HA following the protocols of:
1). Exposure of cells to HA for 30 min followed by drug; and
2). Exposure of cells to HA for 24 followed by drug co-exposure of HA/5-FU.

Cells will be counted. The receptor status of any viable cells will be quantitated using surface epitope FACS analysis.

If blocking of the HA receptors decreases the normally observed synergism between 5-FU and HA, the membrane bound and cytosolic 5-FU will be quantited±HA receptor blocking.

HA degradation by cell lines using [$^3$H]HA and gel filtration chromatography±receptor blocking will be studied.

Effect of HA on the Plasma Membrane

Hyaluronan of molecular weight, 4 sacc, 6 sacc, 12 sacc, 5600 Da, 50,000 Da, 100,000 Da, 250,000 Da, 750,000 Da and 1,500,000 Da will be incubated with breast cancer cell lines at pre-determined "observed-effect" concentrations and the following will be parameters investigated:
1). Extracellular and intracellular calcium flux (cellular probe assays);
2). Regulation of cytoskeletal components (micro-array of cytoskeletal genes);
3). Effect on volume of cells (Coulter size Analysis);
4). Mobility of cancer cells (Boyden Chamber matrigel assays);
5). Quantitation of HA receptors (FACS); and
6). Membrane potential (method to be determined). An investigation of the role of HA neo-adjuvant therapy on the inhibition of organ metastasis will be undertaken. In comparison to other treatment groups, mice receiving the HA therapy have demonstrated that:
1). Reduced lymph node metastasis as compared to other treatment groups;

2). Inhibition of new tumour formation;
3). Increased weight gain; and
4). Enhanced well-being.

These results highlight the possible role of HA anti-cancer therapy as an efficient means of reducing the spread of cancer. Through the obligatory choice of a pre-clinical model there is a restriction, whereby the spread of the secondary cancer normally occurs in the surrounding lymph nodes. It would be advantageous to use a model where we can examine the spread of the cancer to every organ and the bone. By using a model known as the BAG vector metastasis model we would be able to monitor the spread of cancer to every organ and the bone.

In brief, the BAG vector consists of a neomycin-resistant LacZ gene that can be stably transfected into human breast cancer cells. After intracardiac injections into the nude mice, followed by a 6-week treatment program it is. possible to PCR detect the LacZ gene in any metastasizing cells/organs. Faxitron scanning with detection of bone lesions would detect any bone metastasis.

The below treatments will be administered on Day 1, Day 2 of a weekly cycle, for 6 weeks. The treatment groups (5 animals per group) will consist of:
1. Saline
2. 30 mg/kg 5-FU Day 1, Day 2;
3. 12.5 mg/kg HA Day 1, Day 2;
4. 30 mg/kg 5-FU+12.5 mg/kg HA (co-administered on Day 1, Day 2);
5. 12.5 mg/kg HA on Day 1, 30 mg/kg 5-FU on Day 2, 12.5 mg/kg HA on Day 3, 30 mg/kg 5-FU on Day 4;
6. 12.5 mg/kg HA on Day 1, 3;
7. 30 mg/kg 5-FU on Day 2, 4;
8. 15 mg/kg MTX Day 1, Day 2;
9. 15 mg/kg MTX+12.5 mg/kg HA (co-administered on Day 1, Day 2);
10. 12.5 mg/kg HA on Day 1, 15 mg/kg MTX on Day 2, 12.5 mg/kg HA on Day 3, 15 mg/kg MTX on Day 4;
11. 15 mg/kg MTX on Day 2, Day 4;
12. 15 mg/kg MTX, 30 mg/kg 5-FU, 30 mg/kg cyclophosamide on Day 1, Day 2; and
13. 15 mg/kg MTX, 30 mg/kg 5-FU, 30 mg/kg cyclophosamide+12.5 mg/kg HA on Day 1, Day 2;
    12.5 mg/kg HA on Day 1, (15 mg/kg MTX, 30 mg/kg 5-FU, 30 mg/kg cyclophosamide) on Day 2, 12.5 mg/kg HA on Day 3, (15 mg/kg MTX, 30 mg/kg 5-FU, 30 mg/kg cyclophosamide) on Day 4.

Neo-Adjuvant Therapy:
Immediately before intracardiac injection administer the following:
1). 12.5 mg/kg HA;
2). 15 mg/kg MTX;
3). 15 mg/kg MTX, 12.5 mg/kg HA;
4). 30 mg/kg 5-FU;
5). 30 mg/kg 5-FU, 12.5 mg/kg HA;
6). 15 mg/kg MTX, 30 mg/kg 5-FU, 30 mg/kg cyclophosamide; and
7). 15 mg/kg MTX, 30 mg/kg 5-FU, 30 mg/kg cyclophosamide+12.5 mg/kg HA.

Mouse mass and well being will be monitored daily for 6 weeks. On completion of the treatment cycle, each mouse will be scanned for bone lesions. After scanning each organ and body fluid will be removed. A sufficient cross section of the organ will be kept for possible future pathological analysis, while the remaining tissue will be homogenized and subjected to competitive PCR for the detection of the LacZ gene. Any organs which exhibit metastasis will be histologically processed and the pattern of colonization of the cancer cells will be noted using galactosidase staining of the Lac Z gene.

Example 5

In vitro Comparison of Camptosar and Camptosar Combined with Hyaluronic Acid

Materials and Methods

Human Colon Carcinoma Cell Lines HT-29, HCT-116, SK-CO-1, SW620, SW1222 were obtained from the Peter MacCallum, Cancer Institute, Melbourne. Cells were routinely grown and subcultured as a monolayer in 75 cm$^2$ culture flasks in RPMI 1640 media containing 10% fetal calf serum and 10 µg/ml antibacterial/antimycotic stock in a humidified atmosphere of 5% $CO_2$.

Human colon carcinoma cell lines 1215 and LIM2099 were kindly donated by Dr R Whitehead, Ludwig Institute, Melbourne. Cells were routinely cultured as monolayer in 75 cm$^2$ culture flasks in RPMI1640 media supplemented with 5% fetal calf serum, 10 µg/ml bovine insulin, 1 mM hydrocortisone and antibacterial/antimycotic stock Preparation of Colon Cancer Growth Medium Containing 100 nM Hyaluronan (Modal MW 850,000 Da)

To prepare the 100 nM HA growth medium, a quantity of desiccated HA (MW 850 kD) was used to the above-mentioned growth medium. The HA was dissolved at 4° C. for a minimum of 8 h before sterilization by filtration through a 0.22 µm filter.

Preparation of Camptosar for Addition to Colon Cancer Growth Medium+100 nM Hyaluronan (Modal MW 850,000 Da)

A stock solution of 20 mg/ml of Camptosar was purchased from Pharmacia and Upjohn, and was brought to a working concentration of 2 mg/ml with growth media as specified above. The various concentrations of Camptosar were achieved by diluting in the appropriate amount of growth media.

Drug Cytotoxicity Assay

The HCT-116, HT-29, SK-CO-1, LIM1215, LIM2099, SW620 and SW1222 cell lines were routinely grown to 80% confluency. The cells were removed from the culture flask and counted using the haematocytometer. The cells HT-29, HCT-116, SK-CO-1, SW620 and SW1222 were resuspended to 15,000 cells/ml of cell-specific media. The LIM1215 and LIM2099 were resuspended to 30,000 cells/ml of cell-specific media. The cells were plated into 48 well culture plates (1 cm$^2$ surface area) by adding 1 ml of cell suspension per well. The cells were allowed to attach overnight prior to exposure to the test media. The cells were continuously exposed to the following concentrations of test media: 0 µg/ml, 0.25 µg/ml, 0.5 µg/ml, 1 µg/ml, 5 µg/ml, 25 µg/ml and 50 µg/ml Camptosar±100 nM hyaluronan (Modal Mw 850,000). The cells were continuously incubated with the test media for 48 hours. On the day of analysis, the cells were washed with Hanks Balanced Salt Solution. Subsequently, the cells were removed by trypsinization with 0.25% trypsin/

EDTA. An aliquot of the trypsinized cell suspension was counted by the Coulter Counter.

Method of Data Analysis

The raw duplicate or triplicate counts per well were obtained from the $Z_2$ coulter counter. The counts will be averaged and will be expressed as percentage of no drug control.

Mean cells/ml of each replica was calculated using the following formula: (A)

$$\frac{(\text{Raw counts cells/ml 1} + \text{raw counts cells/ml})}{2}$$

Mean cells/ml of 4 wells (B) per conditions was calculated using the following formula (A):

$$\frac{(A1, A2, A3, A4)}{\text{no of replicate}}$$

Let A1, A2, A3 and A4 represents mean cells/ml of each replica % of no drug control was calculated with the following formula:

$$\frac{(B)}{\text{Average of control well/plate}} \times 100$$

Coefficient of variance was calculated with the following formula:

$$\frac{\text{Standard deviation of mean of all four \% of no drug control}}{\text{mean of all four \% of no drug control}} \times 100$$

If the coefficient of variance was more than 15%, outliers were deleted from the set of data.

The percentage of no drug control from two or more sets of experiments on the same cell line was pooled to obtained the average, standard deviation and standard error of the mean. The graph was plotted as the values of the pooled percentage of no drug control with the corresponding concentrations of Camptosar with or without. HA±SEM.

Comparison of Camptosar treatment group with HA combined with Camptosar was achieved by statistical analysis using parametric t-test analysis. On failing of normal distribution, implementation of non-parametric analysis will be carried out using the Mann-Whitney Rank Sum test. The date is presented in Table 8.

TABLE 8

IN VITRO STUDIES

| Cell Line | Cancer Type | IC$_{50}$ of Camptosar ® (µM) | IC$_{50}$ of HyCAMP ™ (µM) |
|---|---|---|---|
| LIM 1215 | Colon | 16 | 1 |
| SW 620 | | 10 | 0.4 |
| LIM 2099 | | 31 | 31 |
| SK-CO-1 | | 5 | 5 |
| SW1222 | | 32 | 32 |
| HT-29 | | 16 | 12 |
| HCT-116 | | 1.5 | 1.5 |

Example 6

In Vivo Toxicology Data

Materials and Methods
Animal Model

Male Out-bred male F1 CBAXC57 mice were purchased from The Animal Central Services Division (Monash University, CLAYTON, Australia) and randomly divided into experimental groups (n=5/group). Treatment commenced when mice attained the desired starting weight of 27.1±2.1 g (1 SD). Any animals with a body weight outside these parameters were excluded from data analysis.

Preparation of Drugs and Control Vehicles for Intravenous Administration

The anti-cancer drug, Camptosar® (CPT-11) was kindly donated from Pharmacia Corporation R & D Global Distribution Center (Kalamazoo, Mich., USA). A 20 mg/mL stock of CPT-11 was prepared and stored at 4° C. until use (diluted to 10 mg/mL in 0.9% (w/v) pyrogen-free injection grade NaCl and used to prepare Camptosar® and HyCAMP™ injections. Desiccated hyaluronan (HA), was purchased from Pearce Pharmaceuticals (Victoria, Australia). A single batch of 10 mg/mL solution was prepared by Biological Therapies (Braeside, Victoria, Australia), packaged into single use 100 mL sterile glass vials and underwent standard chemical and microbiology testing.

Individual injections were prepared according to individual animal masses. The dosage of Camptosar® in both formulations was 25 mg/kg, 50 mg/kg, 100 mg/kg, 150 mg/kg and 200 mg/kg. HyCAMP™ (hyaluronan mixed with Camptosar®) was prepared immediately before injection by mixing calculated volumes of 10 mg/mL hyaluronan (Biological therapies Batch 10806) with a calculated volume of 20 mg/mL Camptosar® to achieve the desired Camptosar® and hyaluronan dosage.

Frequency of Drug and Control Vehicle Administration

Five treatment groups received daily injections until death of the following drug combinations and stated dosages.

Camptosar® only: 25 mg/kg, 50 mg/kg, 100 mg/kg, 150 mg/kg or 200 mg/kg or HyCAMP™: (Hyaluronan combined with Camptosar® to deliver an HA dose of 13.3 mg/kg and a Camptosar® dose of 25 mg/kg, 50 mg/kg, 100 mg/kg, 150 mg/kg or 200 mg/kg).

All injections were administered as a single bolus intravenous injection via the lateral tail vein.

The following data was recorded: Injection Mass; Food Intake; Animal Observations; Clinical Observations; and Animal Autopsy.

Definition of Experimental End Point

Unless otherwise stated in experimental notes the end point of this study was when: >10% loss of body mass within 24 hours; animal energy level <1+; or any animals found dead.

Processing of Tissues at Experimental Endpoint

At experimental endpoint mice were humanely killed by intraperitoneal injection of Nembutal (60 mg/mL). Immediately after death, all internal organs were subsequently removed, weighed and fixed in 10% formalin in phosphate buffered saline. After a period of 16-24 hours of fixation the gastrointestinal tract was sampled and processed for histological processing. In brief, fixed tissue was dehydrated stepwise to 100% ethanol prior to embedding in paraffin blocks from which 2-4 μm sections were cut onto glass microscope slides (Note: all histological processing was performed in The Department of Anatomy, Monash University in accordance with internal quality assurance programs). Mounted sections were then stained with haematoxylin nuclear stain and eosin cytoplasmic stain. Any remaining tissues were kept in the fixative in case they were required for further analysis.

Monitoring of Treatment Side-Effects

Gastro-intestinal tract toxicity, weight loss: One of the most common toxic effects of Camptosar® is on the gastrointestinal tract. Animals were monitored daily throughout the study for visual signs of GI-tract toxicity such as diarrhoea and more severe toxicity manifestations such as weight loss. For demonstration of any weight changes the animal body weight was normalised to the body weight at the time of treatment commencement and expressed as a percentage.

To monitor and score the severity of diarrhea each rat was individually assessed for acute onset diarrhea 30 minutes after the administration of Camptosar®/HyCAMP™ and control vehicles. The following coding system was used:
  0: Normal stool, or absent
  1: Slightly wet soft stool
  2: Moderate wet and unformed stool with moderate perianal staining
  3: Severe watery stool with severe perianal staining Clinical Observations: Autonomic, Behavioural and Neurological Profile Immediately after a single bolus administration of either Camptosar® or HyCAMP™ the acute clinical response to the injection was monitored and subsequently repeated at 30 minutes post injection. An Autonomic, Behavioural and Neurological profile was observed and scored daily, prior to, immediately after and 30 minutes after injection. Where clinical signs were scored on a scale of 0, 1, 2, & 3, prior to injection a baseline value of 0 was set. Immediately after given injection the acute response was observed (B-0') and thereafter at 30 minutes (B-30'). Where scoring was recorded as present or absent, absent was set 0 and present to 1. For statistical comparisons of recovery, the 0'-30' (the difference in observed side effects from the time immediately post injection to 30 minutes post injection) value was used, where a positive value indicated reaction worsening with time whereas a negative value indicated a better reaction to injection with time.

Analysis of Data

Comparison of treatment and control group data was achieved by statistical analysis using parametric t-test analysis. On failing of normal distribution, implementation of non-parametric analysis was carried out using:
  i) Mann-Whitney Rank Sum
  ii) One-way Anova Data was represented graphically by column, scatter and column mean plots. A line graph was used where data was represented as a function of time.

To investigate possible treatment induced organ atrophy or enlargement, the organs were removed and weighed during the post mortem.

The source data including the mouse and tumour masses were the masses recorded on the Animal Autopsy Sheet. Any animals found dead were not included in the data analysis.

The mass of each organ was calculated as a % of the net body weight at autopsy and compared to the organ masses of the saline only control group.

The source data was the measurements recorded on the Animal Observation Sheet. Any animals found dead were not included in the data analysis.

The source data was the measurements recorded on the Food Intake Sheet. Any animals found dead were not included in the data analysis.

The average amount of food consumed per day per mouse as a percentage of the mean net body mass was calculated using the following formula:

$$\frac{\text{(food eaten (g)/number of days)/}\frac{\text{number of rats in box}}{\text{net body mass}}}{} \times 100$$

Male F1 CBAXC57 mice were randomly distributed into five treatment groups (n=5). Treatment groups received either Camptosar® or HyCAMP™ at the following doses: 25 mg/kg Camptosar®±13.3 mg/kg hyaluronan; 50 mg/kg Camptosar®±13.3 mg/kg hyaluronan; 100 mg/kg Camptosar®±13.3 mg/kg hyaluronan; 150 mg/kg Camptosar®±13.3 mg/kg hyaluronan; or 200 mg/kg Camptosar®±13.3 mg/kg hyaluronan.

The treatment regime comprised of daily injections for 14 days or until animal morbidity. At the experimental end-point all organs were weighed and the GI-tract was processed for histopathological assessment of toxicity.

Results

This study demonstrated that animals receiving 25 mg/kg Camptosar® or HyCAMP™ survived for 14 days and were able to receive an accumulative dose of 350 mg/kg drug without experiencing severe adverse effects. Animals receiving 25 mg/kg Camptosar® lost 18% body ($p>0.001$) when compared to the HyCAMP™ treatment group which received an equivalent dose of irinotecan hydrochloride. Animals receiving this dosage of irinotecan hydrochloride did not exhibit any immediate neurological toxicity, early or late on-set diarrhea.

Further, animals receiving 50 mg/kg Camptosar® did not survive past 12 days where the $LD_{50}$ was 475 mg/kg over 9-10 days. At 14 days after commencement of treatment, 60% of animals receiving 50 mg/kg HyCAMP™ survived and the $LD_{50}$ was never reached. Animals receiving HyCAMP™ were able to receive an accumulative dose of 700 mg/kg drug without experiencing severe adverse effects. No significant difference in end-point weight loss was observed between the different treatment groups where weight loss was 15.2 to 20.7% of body weight. Animals receiving this dosage of irinotecan hydrochloride did not exhibit any immediate neurological toxicity, early or late on-set diarrhea.

Moreover, animals receiving 100 mg/kg Camptosar® did not survive past 7 days where the $LD_{50}$ was 550 mg/kg over 5-6 days. At 14 days after commencement of treatment, 12.5% of animals receiving 100 mg/kg HyCAMP™ survived and the $LD_{50}$ was 1150 mg/kg over 11-12 days. Animals receiving Camptosar® exhibited neurological effects 30 seconds after injection and it took 5 h to fully recuperate, while animals receiving HYCAMP™ also demonstrated neurological side-effects 30 seconds after injection but had fully recuperated 30 min after injection. No significant difference in end-point weight loss was observed between the different treatment groups where weight loss was 26.8 to 31.6% of body weight. Animals receiving Camptosar® experienced Grade 2-3 diarrhea while animals receiving HyCAMP™ experienced Grade 1-2 diarrhea.

Animals receiving 150 mg/kg Camptosar® and HyCAMP™ exhibited neurological effects 30 seconds after injection and the Camptosar® group did not recuperate. The HyCAMP™ treatment group recuperated within 90 minutes but after a single dose were found dead after 48 h. Animals receiving 200 mg/kg Camptosar® and HyCAMP™ exhibited neurological effects 30 seconds after injection where the Camptosar® group did not recuperate. Lastly, animals treated with 50-100 mg/kg of Camptosar® demonstrated a significant increase in the mass of the stomach, lungs, spleen and brain when compared to the HyCAMP™ treatment group Animals could receive bolus injections of 25-100 mg/kg Camptosar® where the $LD_{50}$ was demonstrated to be approximately 475 to 550 mg/kg. Animals could receive bolus injections of 25-100 mg/kg HyCAMP™ where the $LD_{50}$ was demonstrated to be approximately 1100-1200 mg/kg. The lethal dose of Camptosar® was found to be >100 mg/kg, whereas the lethal dose of HyCAMP™ was found to be ≥200 mg/kg.

The grade of diarrhea and weight loss was reduced in animals receiving HyCAMP™ versus animals receiving Camptosar®, suggesting that the co-administration of hyaluronan alters the gastrointestinal toxicity often associated with irinotecan hydrochloride.

Through the reduction in weight loss and diarrhea, animals receiving HyCAMP™ demonstrated increased survival over the Camptosar® treatment groups.

This study has clearly demonstrated that the co-administration of hyaluronan with irinotecan hydrochloride attenuates the toxicity of irinotecan hydrochloride so enabling the administration of higher doses.

Example 7

In Vivo Efficacy Data

The following experiment was performed to determine whether the co-administration of hyaluronan with irinotecan hydrochloride (HyCAMP™) increases the efficacy of irinotecan hydrochloride in the treatment of colon cancer, and/or reduce treatment toxicity.

Material and Methods

Human LIM1215 colon cancer xenografts were inoculated into the mammary fat pad of athymic Balb/c/WEHI nude mice. Mice were randomly distributed into eight treatment groups (8 mice per group).

Treatment groups received 50 mg/kg irinotecan±13.3 mg/kg HA; 50 mg/kg irinotecan±26.6 mg/kg HA; or 50 mg/kg irinotecan±150 mg/kg HA.

Control groups received either saline or 13.3, 26.6 or 150 mg/kg HA. The treatment regime comprised of injections on Day 1 of a 7-day cycle for duration of fourteen weeks. Primary tumor volume, animal body mass, energy levels and food consumption were monitored three times weekly.

Colon Carcinoma Cell Line

The human colon carcinoma cell line LIM1215 colon carcinoma cell line was kindly donated by Dr R Whitehead, Ludwig Institute, Melbourne. The cell line was routinely cultured as monolayer in 75 cm² culture flasks in RPMI1640 media supplemented with 5% fetal calf serum, 10 µg/ml bovine insulin, 1 mM hydrocortisone and antibacterial/antimycotic stock. For generation of the primary tumor and injection into mice, cells were grown to 80% confluency, trypsinised in 0.05% trypsin/0.01% EDTA solution, washed twice by centrifugation in a Beckman TJ-6 bench centrifuge (Beckman, Melbourne, Australia) at 400 gav for 10 min, counted using a Model-ZM Coulter counter (Coulter Electronics, England) and resuspended in RPMI1640 media at 2×108 cell/ml.

Mouse Tumor Model

Athymic CBA/WEHI nude female mice (Walter and Eliza Hall Research Institute, Melbourne, Australia), 6 to 8 weeks old, were maintained under specific pathogen-free conditions, with sterilized food and water available ad libitum. Each mouse received one injection containing 1×107 cells in 50-100 µl. The cells were injected with a 26-gauge needle into the mammary fat pad directly under the first nipple. Tumor measurements were made weekly by measuring three perpendicular diameters ($d_1 d_2 d_3$) using digital calipers. Tumor volume was estimated using the formula:

$$(\tfrac{1}{6})\pi(d_1 d_2 d_3)$$

Treatment with irinotecan±HA was commenced after approximately 4-8 weeks of tumor growth when the mean tumor volume measured <100 mm³ (SEM, 10 mm³) and the tumor volume expressed as a percentage of body weight was <0.5%. Any animals with a tumor volume expressed as a percentage of body weight outside 0.25±0.10 (mean±1 SD) were excluded from data analysis.

Tumor Volume

The source data was the measurements recorded on the Animal Observation Sheet. The tumour mass data required for the Hydration Value was sourced from the Animal Autopsy Sheet. The following analysis was performed on the raw data:

The starting tumour volume was defined as the tumour volume (mm³) on the day treatment commenced (i.e., Day 1).

The starting tumour volume as a percentage of net body weight was calculated using the following formula:

$$\frac{\text{starting tumour volume (cm}^3) \times 100}{\text{net body weight (g) on Day 1}}$$

where net body weight was estimated by subtracting a calculated tumour weight (1 g×tumour volume (cm³)) from total mouse body weight.

Tumour volume at experimental end-point was defined as the tumour volume (mm³) on the day of death. For animals which were found dead the tumour volume measured at the last observation was used.

Percentage change in tumour volume at experimental end-point was calculated using the following formula:

$$\frac{\text{end-point tumour volume (mm}^3) - \text{starting tumour volume (mm}^3) \times 100}{\text{starting tumour volume (mm}^3)}$$

The therapeutic effectiveness of anti-cancer treatments are often compared to untreated tumours (saline control group). This was calculated using the following formula:

$$\frac{\%\text{ change in tumour volume at experimental}}{\%\text{ change in tumour volume at experimental}} \times 100$$
$$\text{end-point of the Control group}$$

The mean tumour volume was calculated for each week of the treatment period and plotted±SEM as a function of time using the following formula:

$$\frac{\text{sum of the tumour volumes (mm}^3\text{) of each mouse}}{\text{number of mice}}$$

A well vascularized, viable tumour contains more mass and has a lower water content than a necrotic, poorly vascularized tumour. This relationship was examined by calculating the Hydration Value which indicates the mass (mg) of each $mm^3$ of tumour using the following formula:

$$\frac{\text{end-point tumour volume (mm}^3\text{)}}{\text{autopsy tumour mass (mg)}}$$

Following the completion of the 14-week study, mice from each treatment group were classified into one of four categories based on the extent of their tumour progression. The categories and criteria for each were as follows (Maucher & von Angerer, 1994):

i) Complete remission: Tumour not palpable ii) Partial remission: Tumour volume<50% of initial (equates to values<−50% change in tumour volume at experimental end-point)

iii) Static Tumours: Tumour volume 50-150% of initial (equates to values between −50 and 150% change in tumour volume at experimental end-point)

iv) Progressing Tumours: Tumour volume>150% of initial (equates to values>150% change in tumour volume at experimental end-point)

Preparation of Irinotecan and Hyaluronan Drug Combinations

Desiccated hyaluronan Modal $M_r$ 800 kD-850 kD was dissolved in sterile water to a final concentration of 10 mg/mL, filter sterilized through a 0.22 µm filter, and stored at 4° C. until used. A stock solution of 20 mg/ml of Irinotecan was purchased from Pharmacia and Upjohn and was diluted to 4 mg/mL in intravenous grade sodium chloride then used to prepare irinotecan and HyCAMP injections. The dosage of HA administered remained at 13.3 mg/kg throughout the study. The dosages of irinotecan/HyCAMP administered were 50 mg/kg.

Mice were randomly distributed into each of eight treatment groups (8 mice per group). Individual mice were placed in an injection box, and treatment administration was via the tail vein using a 26-gauge needle. To ensure the accuracy of each administered dosage, syringes were weighed before and after injection using an analytical balance.

TABLE 9

Treatment Administration Protocol for 14-week Study

| Treatment Group | Animal Dosage | Injection Day |
|---|---|---|
| Saline | 0.9% Injection Grade | Day 1 of 7 Day Cycle* |
| HA | 13.3 mg/kg HA | Day 1 of 7 Day Cycle* |
| HA | 26.6 mg/kg HA | Day 1 of 7 Day Cycle* |
| HA | 150 mg/kg HA | Day 1 of 7 Day Cycle* |
| Irinotecan | 50 mg/kg irinotecan | Day 1 of 7 Day Cycle* |
| HyCAMP | 50 mg/kg irinotecan + 13.3 mg/kg HA | Day 1 of 7 Day Cycle* *: for fourteen weeks |
| HyCAMP | 50 mg/kg irinotecan + 13.3 mg/kg HA | Day 1 of 7 Day Cycle* *: for fourteen weeks |
| HyCAMP | 50 mg/kg irinotecan + 26.6 mg/kg HA | Day 1 of 7 Day Cycle* *: for fourteen weeks |
| HyCAMP | 50 mg/kg irinotecan + 13.3 mg/kg HA | Day 1 of 7 Day Cycle* *: for fourteen weeks |

The experimental end-point for each animal occurred either when the animal had to be euthanized due to a high degree of disease progression or when the 14-week study had been completed. The animals were monitored three times weekly and the following criteria were established to determine whether an animal had reached the experimental end point: tumour mass is greater than 10% of the animals total body mass; the animal is metabolically stressed (i.e. losing weight); or the animal is immobilized.

Following the experimental end-point being reached, each animal was killed by receiving a lethal dose of 100 µl Nembutal (60 mg/ml) by intraperitoneal injection and cervical dislocation. Animals were weighed and tumor volumes measured.

Immediately after killing the mouse the tumor, liver, heart, spleen, bladder, left and right kidneys, uterus, lungs, stomach, intestines, brain and lymph nodes were excised and weighed and placed in 10% formalin buffered solution. The tissue was fixed for 16-24 h before histological processing. Fixed tissue was dehydrated stepwise to 100% ethanol and embedded in paraffin blocks from which 2-4 µm sections were placed on glass microscope slides. Staining the tissue sections with a haematoxylin nuclear stain and eosin cytoplasmic stain highlighted any pathological features that could indicate treatment toxicity.

One of the most common toxic effects of irinotecan is on the gastrointestinal tract (MIMS, 2000). Animals were monitored three times weekly for GI tract upset such as diarrhoea and more severe toxicity manifestations such as weight loss. Weight loss was monitored by calculating net body weight as estimated by subtracting tumour mass, which was calculated as 1 g×tumour volume ($cm^3$) as cited in Shibamoto et al, 1996. For demonstration of any weight changes the animal body weight was normalized to the body weight at the time of treatment commencement as $$\frac{\text{Body mass (ex tumour)} - \text{body mass}}{\text{at commencement of treatment (ex tumour)}} \times 100$$
$$\text{Body mass at commencement of treatment (ex tumour)}$$

Due to the severe side effects associated with irinotecan administration, animal energy levels were monitored three times weekly to give an indirect assessment of animal health. Each animal was scored on an arbitrary four-point scale, ranging from 0 (minimally energetic) to 4+ (maximally energetic). In judging energy levels, such factors as mobility, interest in surroundings, response to stimuli and general activity were considered. In plotting energy level data, animals that had reached the experimental end-point were scored as zero to minimise biased data representation due to decreased animal survival.

Immediately after a single bolus administration of either irinotecan or HyCAMP the acute clinical response to the injection was monitored and subsequently repeated at 30 minutes post injection. A full autonomic profile of each mouse will be recorded. Where clinical signs were scored on a scale of 0, 1, 2, & 3, prior to injection a baseline value of 0 was set. Immediately after given injection the acute response was observed (B-0') and thereafter at 30 minutes (B-30'). Where scoring was recorded as present or absent, absent was set 0 and present to 1. For statistical comparisons of recovery, the 0'-30' (the difference in observed side effects from the time immediately post injection to 30 minutes post injection) value was used, where a positive value indicated reaction worsening with time whereas a negative value indicated a better reaction to injection with time.

To ensure that treatments did not induce organ atrophy or enlargement, the organs were removed and weighed during the post mortem blood. The mass of each organ was calculated as a % of the overall net body weight, and compared to the organ masses of the saline only group.

The overall patient survival time was calculated as the time (days or weeks) that the animal lived after the commencement of treatment which was designated day 1.

Results

The efficacy of irinotecan as an anti-neoplastic agent was increased when co-administered with HA. More specifically, mice receiving 50 mg/kg HyCAMP™ demonstrated significantly greater tumor regression than mice receiving the equivalent irinotecan dosage, including complete tumor regression in 17% of mice. No significant differences in tumor response were noted in HyCAMP™ formulations containing 13.3, 26.6 or 150 mg/kg HA.

Throughout the study in the mice receiving irinotecan alone, tumor volume regressed to a maximum of 50% of starting volume. This was observed by weeks 6-8 and thereafter became non-responsive to further cycles of irinotecan chemotherapy. In contrast, HyCAMP™ therapy continued to regress tumor volume to approximately 90% of original starting volume.

As evidenced by the hydration value of a tumor, HyCAMP™ therapy tumors conttumors statistically significant higher mass of necrotic tissue when compared with mice receiving irinotecan treatment.

Weight gain in treatment groups was retarded when compared with control groups. The difference in the degree of observed weight loss in the irinotecan and HyCAMP™ treatment groups was comparable.

Mice receiving HyCAMP™ therapy resulted in 100% population survival whereas treatment with irinotecan resulted in approximately 57% of the treatment group surviving to the end of the 14-week study.

Lastly, the increase in targeting of irinotecan to the pathological site, when combined with hyaluronan, was correlated to the confirmed presence of high levels of C44 expression on the cell surface of LIM1215 by FACS analysis.

The results of this study are presented in Table 10. These findings demonstrate the potential of HA in the targeting and delivery of irinotecan to colon cancer tumors, thereby increasing therapeutic efficacy and increasing population survival.

TABLE 10

| | | | | | |
|---|---|---|---|---|---|
| | | | | HyCAMP ™ | |
| Species/Strain | No./ Sex | Route of Admin. | Dose (mg/kg) | Administration schedule | Results/Observations |
| Mouse CBA nude | 8F 8F 8F 8F 8F 8F | IV bolus | 13.3 HA 26.6 HA 150 HA 50 Camptosar ® ± 13.3 HA 50 Camptosar ® ± 26.6 HA 50 Camptosar ® ± 150 HA | Day 1 of 14 × q7 D | All animals treated with HA had progressive disease and no treatment toxicity was observed. The efficacy of Camptosar ® was increased when co-administered with HA. More specifically, mice receiving 50 mg/kg HyCAMP ™ demonstrated significantly greater tumor regression than mice receiving the equivalent Camptosar ® dosage; 100% of HyCAMP ™ animals had a complete remission or partial response versus a 28% of the animals treated with Camptosar ®. At experimental end-point population survival in HyCAMP treated mice was 100% whereas mice receiving Camptosar ® therapy was only 57%. |

Example 8

Effect of Hyaluronan as a Cytotoxic Compound for the Inhibition of Cancer

Effect of HA on Cell Proliferation

To determine if hyaluronan could act as an anti-proliferative or even cytotoxic compound in vitro the following experiments were performed.

Figure 7:
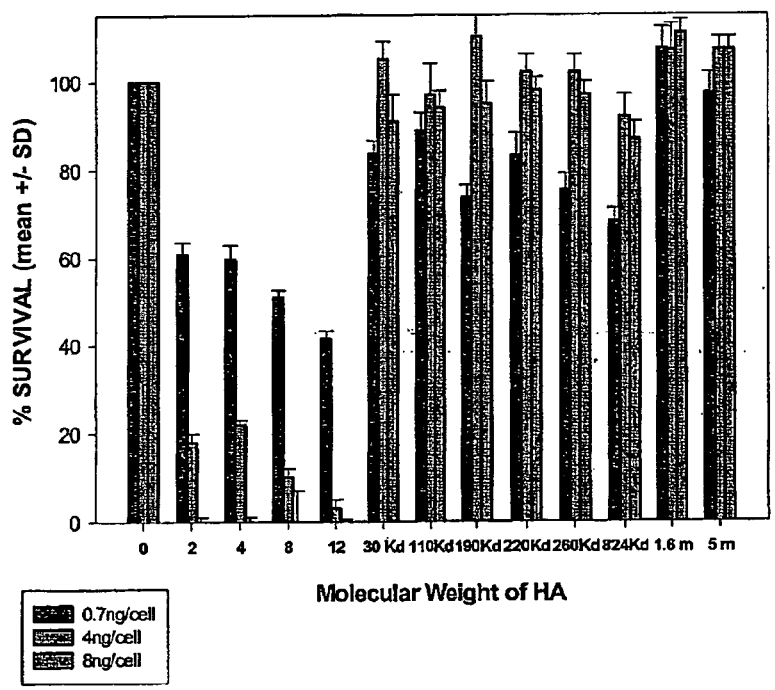
FIG. 7 is a graph showing the comparison of the effect of different molecular weights of hyaluronic acid on cell survival of MDA-MB-468.

CD44-positive and CD44-negative breast cancer cells were incubated with 0.7 to 8 ng/cell of HA having the following molecular weight: 396, 792, 1584, 2376, 30 kDa, 110 kDa, 190 kDa, 220 kDa, 260 kDa, 824 kDa, 1600 kDa and 5000 kDa for 48 h. This experiment demonstrated that at a MW less than 30 kDa, the HA was able to exert a cytotoxic effect at all tested concentrations (see FIG. 7).

Limits of HA in Breast Cancer Cell Lines

Figure 8A:
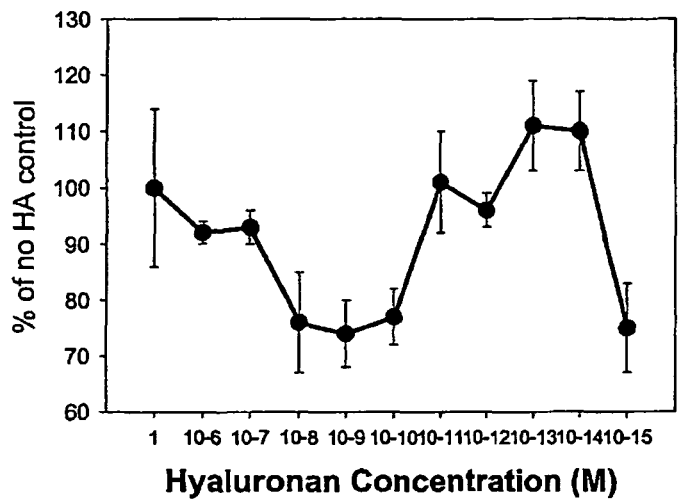
FIGS. 8A-B are graphs demonstrating the effects of titration of hyaluronan on breast cancer cell lines.
Figure 8B:
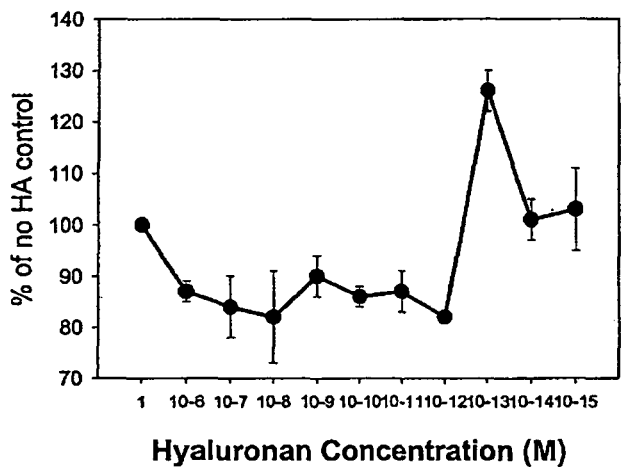

To determine the upper and lower concentration threshold of 750 kD HA three breast cancer cell lines were incubated with $10^{-15}$M to $10^{-6}$M HA. Cells were grown in the presence of the HA for three days, then cells were subjected to the cell adhesion assay procedure. HA exhibited a slight anti-proliferative effect on both the CD-44 positive MDA-MB 468 and MDA-MB 435 breast cancer cell lines (see FIGS. 8A-B). At 1 pM to 1 µM HA reduced proliferation up to 20% in the MDA-MB 468 cell line and up to 25% in the MDA-MB 435. Since HA production is an integral component of mitosis the presence of large amounts of exogenous HA may result in a negative feedback which signals the cancer cells into senescence and therefore would inhibit them from metastasizing to other organs.

Effect of HA on Breast Cancer Cell Morphology

To investigate if HA altered the morphology of human breast cancer cells, human breast cancer cell line MDA-MB 468 was exposed to 750 kD HA for 24 h and then photographed. At 10 ng/ml there was a reduction in cell number, but no difference in morphology. At 100 ng/ml and 1 mg/ml the cells appeared to be undergoing an osmotic response where the cells appeared to "swell". At 2 mg/ml and 5 mg/ml the cells became granular and appeared to be undergoing apoptosis once again ensuring that the cells would not metastasize to secondary organs.

Tumor Volume In Vivo

Figure 9A:
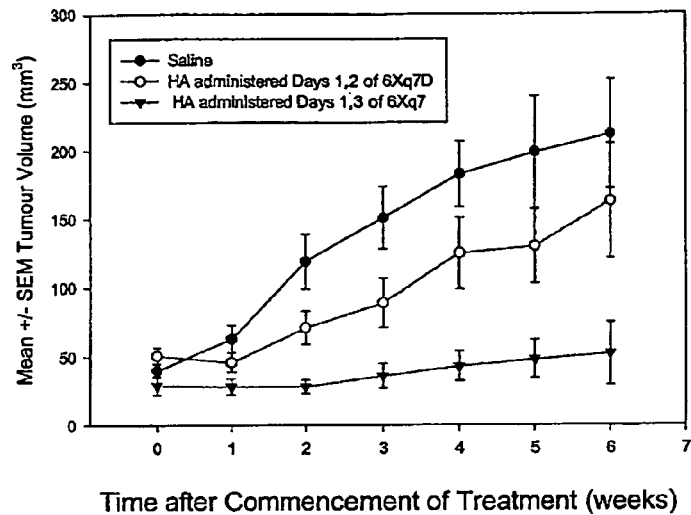
FIGS. 9A-B are graphs demonstrating the effects of titration of hyaluronan effects of hyaluronan in vivo.
Figure 9B:
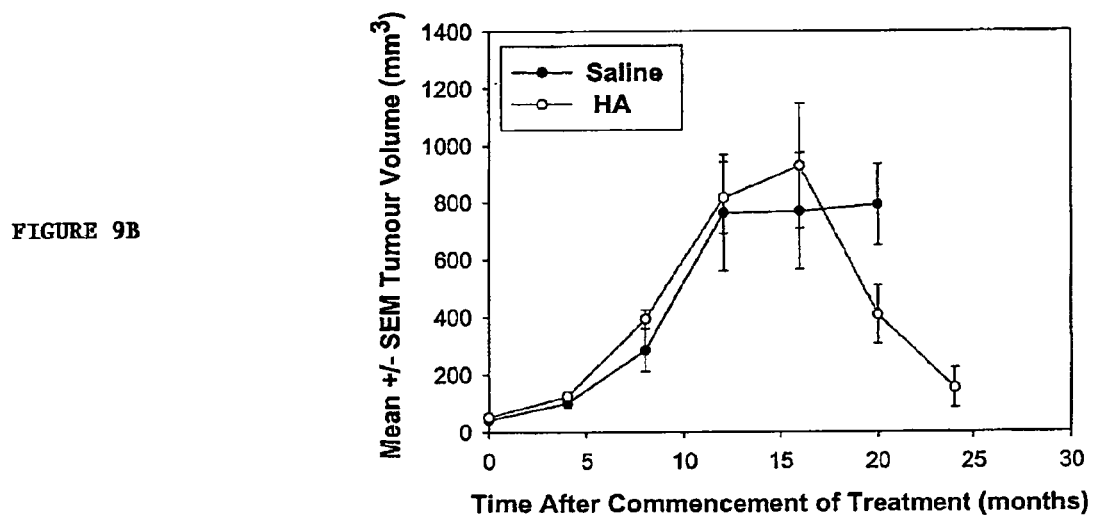

To determine the effect of HA on tumor volume in vivo, 12.5 mg/kg of HA was administered on day 1 and 2 of a 7 day cycle for 6 cycles and 12.5 mg/kg on day 1 and 3 of 7 day cycle for 6 cycles (FIG. 9A) or 12.5 mg/kg on day 1 and 8 of 28 day cycle for 6 cycles (FIG. 9B). HA routinely resulted in a lower % T/C, where in 3/3 experiments the difference reached significance ($p<0.001$, Student t-test). This anti-proliferative effect could be due to the degradation of the HA into apoptotic-inducing fragments and/or the microembolisation effect, which could result in tissue hypoxia and subsequent cell death.

HA Accumulation in Tumors

Figure 10:
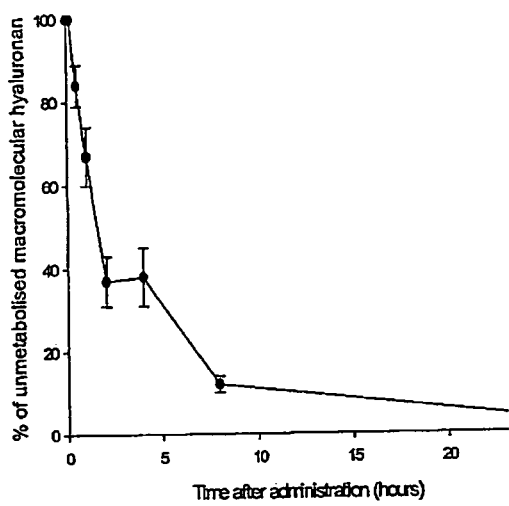
FIG. 10 is a graph indicating that intravenous hyaluronan forms a micro-embolic drug depot in the vasculature of human breast cancer xenografts. After the intravenous administration of 15 mg/kg of 825 kDa [$^3$H] HA the tumors were homogenized and the cell/tissue extracts analyzed using size exclusion chromatography. The percentage of macromolecular weight HA was calculated as material eluting in the void volume of a Superose 12 gel.

It has been well established that high molecular weight hyaluronan inhibits cell migration (see, for example, Dube et al., Andreutti et al., Ferns et al., and Tamoto et al.), therefore the accumulation of high molecular weight HA within a tumor could inhibit tumor cell migration to secondary organs, hence preventing metastasis. To demonstrate that after a single bolus dose of intravenous HA there was a prolonged accumulation of high molecular weight, 15.9 mg/kg of [$^3$H] HA (MW of 825 kD) was intravenously injected into female nude mice bearing MDA-MB 468 human breast cancer xenografts. Mice (n=5/time point) were killed at 15 min, 30 min, 60 min, 2 h, 4 h, 8 h, 24 h, 48 h and 72 h after intravenous administration. Chromatographical analysis of the tumor homogenate demonstrated that after one bolus injection of 825 kDa [$^3$H]HA the high molecular weight rapidly aggregated within the micro-vasculature of the tumor resulting in a microembolic effect which was observed for up to 8 h. The microembolization of the HA did not prevent the internalization of the HA into the tumor cells as demonstrated by the identification of cellular metabolic end-products of $^3$H-acetate and water in the tumor homogenates. Macromolecular HA (Modal $M_r$ ~825 kDa) was present for up to 24 h after intravenous administration suggesting a slow rate of turnover (FIG. 10). It is important to consider that these data were obtained after a single bolus injection. When applied to the clinical situation where anti-cancer drugs are often administered over an extended infusion period it is likely that the HA microembolism would continue to form and maintain its intra-tumoral presence for longer thereby potentially increasing the HA retention and concentration within the tumor. Therefore based on these data it is possible that in the clinical situation the intra-tumoural concentration of HA may be high enough to result in an inhibition of tumor cell metastasis.

Example 9

Effect of Hyaluronan on the Proliferation of Human Breast and Colon Cancer Cell Lines The effect of HA on the proliferation of human breast and colon cancer cell lines was determined according to the methods set forth in the Table 11.

TABLE 11

| Incubation Conditions | Cancer Cell Lines | HA Receptor status (%) | | | Effect of HA on cell proliferation* (mean ± standard deviation) | | |
|---|---|---|---|---|---|---|---|
| | | CD44s[a] | CD44v6[b] | RHAMM[b] | 100 nM | 500 nM | 10 μM |
| | BREAST CANCER | | | | | | |
| 3 days constant exposure | MDA MB 468 | 80 | 0 | 50 | 99 ± 6 (n = 20) | 95 ± 3 (n = 8) | 99 ± 6 (n = 20) |
| | MDA MB 435 | 50 | 50 | 75 | 85 ± 17 (n = 16) | 55 ± 6 (n = 8) | 101 ± 1 (n = 8) |
| | MDA MB 231 | 50 | 80 | 75 | 106 ± 11 (n = 20) | 100 ± 1 (n = 8) | 101 ± 5 (n = 8) |
| | ZR-75-1 | 0 | 0 | 38 | 103 ± 4 (n = 20) | 102 ± 1 (n = 8) | 100 ± 3 (n = 8) |
| 30 min HA followed by growth for 3 days | MDA MB 468 | 80 | 0 | 50 | 97 ± 15 (n = 12) | NOT DETERMINED | |
| | MDA MB 435 | 50 | 50 | 75 | 86 ± 6 (n = 12) | | |
| | MDA MB 231 | 50 | 80 | 100 | 86 ± 3 (n = 8) | | |
| 24 H HA followed by growth for 3 days | MDA MB 468 | 80 | 0 | 50 | 84 ± 1 (n = 4) | NOT DETERMINED | |
| | MDA MB 435 | 50 | 50 | 75 | 111 ± 6 (n = 8) | | |
| | COLON CANCER | | | | | | |
| 3 days constant exposure | LIM 1215 | 100 | ND | ND | 89 ± 5 (n = 8) | NOT DETERMINED | |
| | SW620 | 4 | ND | ND | 97 ± 1 (n = 8) | | |
| | LIM 2099 | ND | ND | ND | 105 ± 2 (n = 16) | | |
| | SK-CO-1 | ND | ND | ND | 95 ± 3 (n = 8) | | |
| | SW1222 | 13 | ND | ND | 99 ± 1 (n = 8) | | |
| | HT-29 | 46 | ND | ND | 82 ± 14 (n = 8) | | |
| | HCT-116 | 74 | ND | ND | 92 ± 0 (n = 8) | | |

[a]As compared to normal epithelial cells using dot blot analysis[66]
[b]As determined by immunohistochemistry or FACS in the Hyaluronan Laboratory
*Number expressed as % of untreated control

Example 10

Summary of the Effect of 750 KD or 825 KD HA on Breast and Colon Cancer Xenografts, Metastasis, Body Mass and Survival In Vivo The following table sets forth the results of the administration of HA on breast and colon cancer xenographs, metastasis, body mass and survival in vivo.

CD44-Negative Breast Cancer Xenografts

Figure 12:
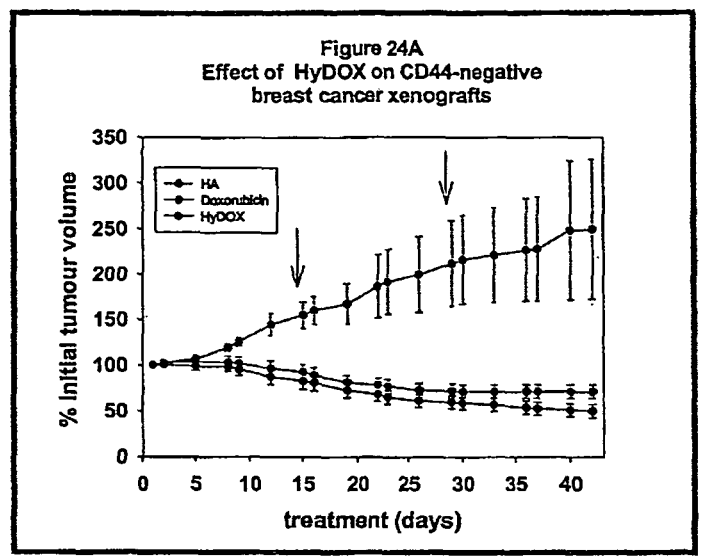
FIG. 12 is a graph demonstrating the effect of DOX and HyDOX™ on CD44-negative breast cancer xenographs.

Treatment groups successfully completed 5 weekly cycles over the duration of the 42-day study. Measurements of the % change in tumour volume over the treatment period are shown in FIG. 12. Unlike previous studies in CD44-positive tumours, HyDOX™ did not significantly increase the therapeutic efficacy when compared to the DOX group.

TABLE 11

| Test Compound | Administration Regimen | TV (Mean ± SEM) Day 0 | TV (Mean ± SEM) Endpoint | % T/C | % change in TV during treatment (Mean ± SEM) | % animals with LN mets# N = 6–8 | % change in NBM during treatment (Mean ± SEM) | Survival (Mean + SEM) (days) |
|---|---|---|---|---|---|---|---|---|
| MDA-MB 468 Breast cancer xenografts in nude mice | | | | | | | | |
| Saline | Day 1 & 2 of 6 × q7 D | 40 ± 5 | 241 ± 40 | 100 | 504 ± 96 | 87.5 | 0.09 ± 1.87 | 42 ± 0 |
| 12.5 mg/kg of 750 kD HA | Day 1 & 2 of 6 × q7 D | 51 ± 6 | 163 ± 41 | 47 | 239 ± 78 | 0 | 2.59 ± 1.00 | 42 ± 0 |
| 12.5 mg/kg of 750 kD HA | Day 1 & 3 of 6 × q7 D | 29 ± 7 | 52 ± 23 | 13 | 66 ± 30* | 0 | 0.91 ± 1.59 | 42 ± 0 |
| Saline | Day 1 of 6 × q7 D | 32 ± 11 | 395 ± 60 | 100 | 1305 ± 258 | 12.5 | 19.3 ± 2.0 | 43 ± 0 |
| 13.3 mg/kg of 825 kd HA | Day 1 of 6 × q7 D | 53 ± 8 | 384 ± 85 | 45 | 588 ± 61* | 12.5 | 18.0 ± 2.0 | 43 ± 0 |
| Saline | Day 1 & 8 of 6 × q28 D | 43 ± 6 | 1114 ± 198 | 100 | 2777 ± 618 | 50 | −3.02 ± 3.05 | 118 ± 8 |
| 12.5/kg of 750 kD HA | Day 1 & 8 of 6 × q28 D | 53 ± 7 | 795 ± 211 | 68 | 1875 ± 682 | 28.5 | −6.26 ± 6.64 | 121 ± 10 |
| ☐Saline | Day 1 & 8 of 6 × q28 D | 210 ± 18 | 1656 ± 292 | 100 | 547 ± 125 | 100 | 4.39 ± 3.93 | 130 ± 14 |
| 12.5/kg of 750 kD HA | Day 1 & 8 of 6 × q28 D | 175 ± 24 | 1424 ± 329 | 143 | 780 ± 241 | 25 | 6.10 ± 3.29 | 150 ± 11 |
| LIM 1215 Colon cancer xenografts in nude mice | | | | | | | | |
| Saline | Day 1 of 7 × q13 D | 30 ± 2 | 1702 ± 151 | 100 | 5812 ± 725 | | 13.3 ± 4 | 92 ± 4 |
| 13.3 mg/kg of 825 kD HA | Day 1 of 7 × q13 D | 36 ± 3 | 1635 ± 129 | 81 | 4706 ± 501 | | 11.3 ± 3 | 93 ± 4 |
| Saline | Day 1 of 7 × q7 D | 30 ± 2 | 357 ± 61 | 100 | 1114 ± 206 | | 7.2 ± 3 | 50 ± 0 |
| 13.3 mg/kg of 825 kD HA | Day 1 of 7 × q7 D | 36 ± 3 | 401 ± 42 | 97 | 11077 ± 133 | | 5.2 ± 2 | 50 ± 0 |
| 26.6 mg/kg of 825 kD HA | Day 1 of 7 × q7 D | 36 ± 3 | 260 ± 39 | 60 | 671 ± 132 | | −0.5 ± 2 | 50 ± 0 |

Abbreviations used in table:
D = Days;
q7 D = 7 day cycle; q28 D = 28 day cycle;
Lymph node metastasis as determined by CEA immunohistochemistry of paraffin sections
Statistical significance using Student t-test (p = 0.001)
% T/C calculated as % change in tumor volume over treatment period of treatment group as % of tumor volume over treatment period of saline group

Example 11

Evaluation of HyDOX™ in the Treatment of Breast Cancer in Breast Cancer Xenographs

CD44-Positive Breast Cancer Xenografts

Figure 11A:
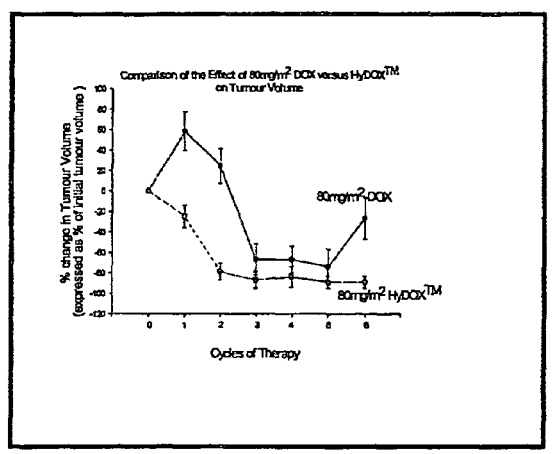
FIG. 11A-B are graphs demonstrating the effects of DOX vs. HyDOX™.

In comparison to DOX (doxorubicin) treatment groups, HyDOX™ (a formulation comprising HA and DOX) significantly reduced the tumour volume of breast cancer when it was administered for 6 cycles consisting of Days 1 of a 7-day cycle at a dosage of 80 mg/m² (FIG. 11A).

Figure 11B:
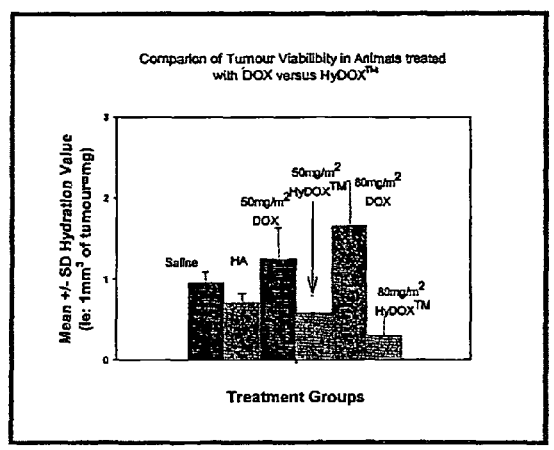

To gauge the therapeutic effectiveness of DOX versus HyDOX™ tumor viability in animals treated with HyDOX was compared to animals treated with DOX (FIG. 11B).

Figure 13:
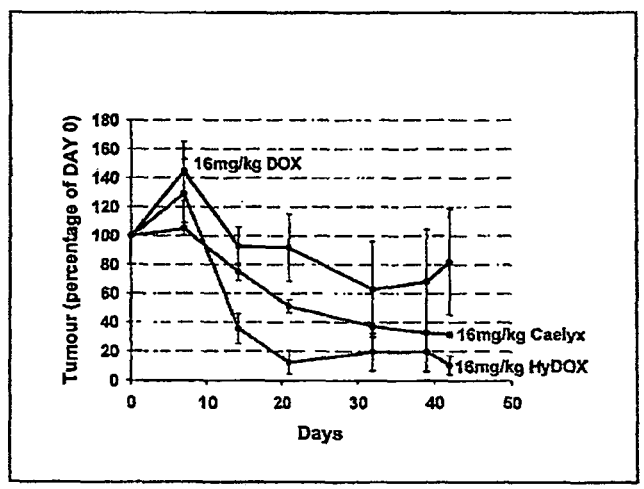
FIG. 13 is a graph demonstrating the effect of DOX, HyDOX™, and Caelyx on CD44-positive breast cancer xenographs.

Comparison of Doxorubicin, HyDOX™ and Caelyx in CD44-Positive Breast Cancer Xenografts As the most commonly used form of doxorubicin is in a pegylated liposomal preparation known as Caelyx, it was necessary to compare the efficacy of HyDOX™ versus the industry-preferred product. As seen in FIG. 13, HyDOX™ demonstrated a greater tumour response than the liposomal preparation.

Cardiotoxicity

In the HyDOX™ efficacy study there were indications of reduced cardiac damage and due to the well-established fact that DOX causes chronic cardiac damage thereby restricting its clinical usefulness. A study was specifically designed to address the potential protective role of HyDOX™ against cardiac damage.

Figure 14:
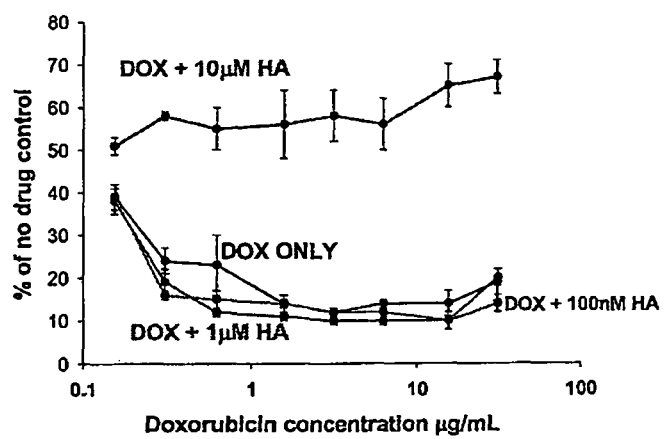
FIG. 14 is a graph showing the effects of different concentrations of hyaluronan on the cytotoxicity of doxorubicin. Rat myocardiocytes were exposed to DOX+10 μM HA, DOX only, DOX+1 μM HA, or DOX+100 nM HA and their survival was plotted as a percentage of the control containing no drug.

Differentiated rat myocardiocytes were exposed to varying concentrations (ranging from highest therapeutic exposure of 1 μM to the average circulating dose of 270 nM, when assuming a 80 mg/m² injection). Cells were subjected to the previously described cell adhesion cytotoxicity assay. HyDOX™ with a HA component of 10 μM or 11 μg/ml which is lower than the circulating levels of HA which follows an injection of 60 mg/m² of HyDOX™ protected the cardiomyocytes from the cytotoxicity of DOX (FIG. 14).

Example 12

Comparison of Doxorubicin, HyDOX™ In Vivo

In order to compare the effect of doxorubicin and HyDOX™ in vivo, six treatment groups each consisting of 8 hypertensive rats were administered the following treatment: 1) no treatment, 2) Hyaluronan (13.3 mg/kg, IV injection), 3) saline, 4) doxorubicin (1.5 mg/kg, IV injection), or HyDOX (1.5 mg/kg doxorubicin; 13.3 mg/kg HA).

Figure 15:
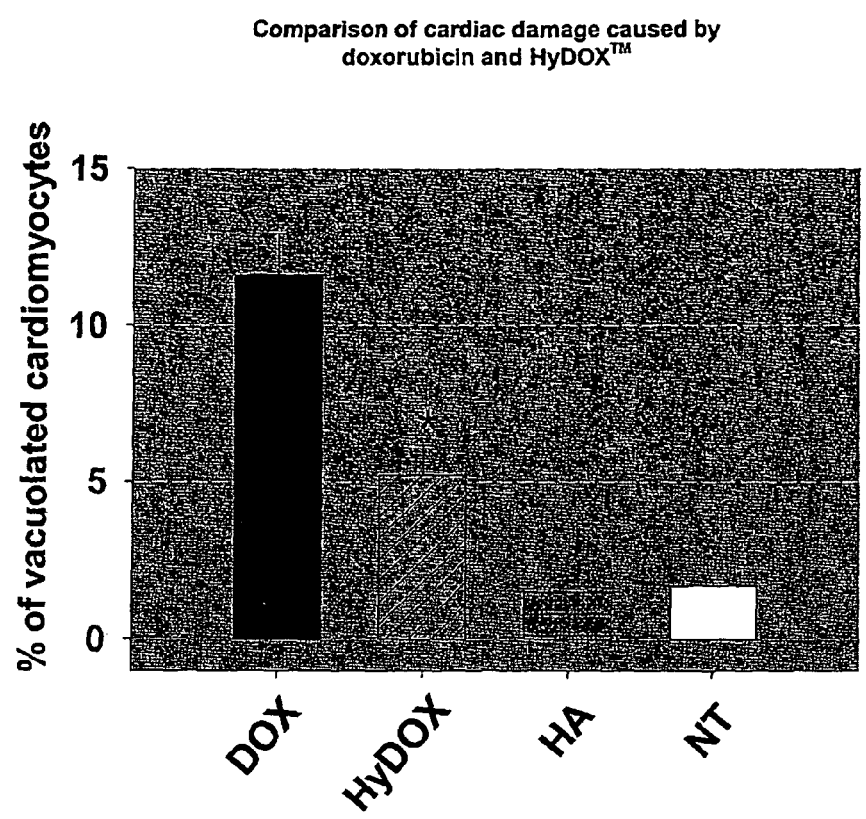
FIG. 15 is bar graph demonstrating a comparison of cardiac damage caused by DOX and HyDOX™.

Animals were injected on a weekly basis for 12 weeks. One week after final treatment the rats were humanely killed and the heart removed for assessment of cardiac damage. Assessment of cardiac damage was performed by to directly assess the degree of doxorubicin-generated vacuolation of the cardiac myocytes using electron microscopy. Sections of the intraventricular septum from rat hearts were processed for EM analysis. The degree of cardiomyopathy was scored by an adaptation of the Billingham method. Cumulative amount of doxorubicin and HyDOX™ over the 12 week period=19.5 mg/kg. The results of this experiment indicate that it is possible to administer 2-3 times the dose of HyDOX™ before obtaining the same degree of cardiomyocyte vacoulation (FIG. 15).

Example 13

Bone Marrow Toxicity

In order to determine if HyDOX™ was toxic to bone marrow, circulating erythrocytes, platelets and white cell subpopulations were quantified. The results indicate that lower doses of HyDOX™ (FIGS. 16A and B) significantly increased the number of circulating polymorphic white cells.

Example 14

HA and Irinotecan Treatment of Patients with Colorectal Cancer

Patient Selection

All patients entered into this study had advanced or metastatic CRC with present or past histological documentation of colorectal adenocarcinoma (CRC). Patients were required to have metastatic disease that was either refractory to or had progressed within 6 months of first line 5-FU treatment. Previous oxaliplatin was permitted but at the time of initiation of treatment with HA and irinotecan, oxaliplatin-based therapy was not readily available as a first line treatment regimen for the management of metastatic CRC. Other eligibility criteria were age 18-75, ≥1 measurable lesion (≥1 cm on spiral CT or MRI), ECOG performance status (PS) of 0 or 1, estimated survival of ≥12 weeks, adequate bone marrow function (neutrophil count≥$1.5 \times 10^9$/L, platelets≥$100 \times 10^9$/L), adequate liver function (bilirubin≤1.25×upper limit of normal, ALT≤5×upper limit of normal) and adequate renal function (creatinine of ≤0.2 mmol/L). Major exclusion criteria were active inflammatory bowel disease, ≥grade 2 chronic diarrhea, bulky disease (>50% hepatic involvement, >25% lung involvement, or abdominal mass≥10 cm), cerebral metastases, Gilbert's syndrome, previous exposure to irinotecan, any prior radiotherapy to the pelvis or to >30% of bone marrow, currently active second malignancy or other serious co-morbid disease. All patients provided written informed consent prior to enrolment and the study was approved by the ethics committee of the participating institution.

Study Design

A HA and irinotecan composition was administered intravenously over 90 minutes every 3 weeks to a maximum of 6 cycles. The dose of HA was fixed at 1000 mg/m² and the initial dose of irinotecan was 300 mg/m². All patients received a premedication of a 5-HT3 inhibitor and dexamethasone. If no significant treatment related toxicity was seen at this initial dose then the dose of irinotecan was to be escalated to 350 mg/m² for subsequent cycles. No dose modification of HA was planned.

Toxicities were graded according to the National Cancer Institute Common Toxicity Criteria (NCICTC), version 1. Patients who experienced any grade III or IV toxicities (other than alopecia and thrombo-embolic events) received a 25% dose reduction of their subsequent cycles of irinotecan (but not HA). A dose delay of up to 21 days till resolution of the toxicities to grade I or less was permitted. Patients who developed grade III or IV thrombo-embolic events were taken off study. All patients received education regarding the potential for treatment related diarrhea and the appropriate use of loperamide, which was routinely dispensed at the time of the first cycle of HyCAMP™. Prophylactic use of granulocyte-colony stimulating factors or erythropoietin was not permitted.

Formulation of the Therapeutic Composition

The therapeutic composition was presented in a pre-assembled kit form comprising one 100 ml vial of 1% hyaluronan in water for injection that fulfilled the specifications as shown in Table 12:

TABLE 12

1% W/V HA IN INJECTION GRADE WATER

| Tests | Specification |
|---|---|
| Container Description | A 100 ml Flint Glass Vial with a 20 mm Rubber Stopper and 20 mm Aluminum Seal. |
| Product Description | A clear, colorless, odorless, slightly viscous liquid. |
| Closure Integrity | Vials are adequately sealed. |
| Fill Volume | 100-105 ml |
| pH (1% solution at 25° C.) | 6.0 to 8.5 |
| Identification (IR Spectrum) | Conforms to Reference Standard as outlined in BP 2003 monograph |
| Density | 0.990 to 1.010 |
| Molecular Weight by Intrinsic Viscosity | 800 kDa-950 kDa |
| Particulate Matter (USP 26) | No visible particles No detectable particles |
| Sterility (EP) | Passes Test |
| Bacterial Endotoxins (LAL) (EP) | NMT 0.07 EU/mg |
| HA Quantization Assay | 9-11 mg/ml |

The 1% w/v hyaluronan was formulated with a finished product form of a irinotecan formulation as shown in Table 13:

TABLE 13

| Ingredient | Specification | Purpose | Conc. |
|---|---|---|---|
| Irinotecan | Pfizer in-house specifications | Active | 20 mg/ml |
| Sorbitol | USP-NF | Excipient | 45 mg/ml |
| Lactic acid | USP-NF | Excipient | 0.9 mg/ml |
| Water for Injection (WFI) | USP-NF | Diluent | q.s |

The components of the final formulation (e.g. HYCAMP) depended upon the patient surface area, where the surface area was assumed to be 1.4 to 2 mg/m² at a dosage range of 125 mg/m² to 350 mg/m². The formulation of which is disclosed in Table 14:

TABLE 14

| Ingredient | Purpose | Conc | Final Conc |
|---|---|---|---|
| Irinotecan | Active | 20 mg/ml | 0.35-1.4 mg/ml |
| Sorbitol | Excipient | 45 mg/ml | 0.79-3.2 mg/ml |
| Lactic acid | Excipient | 0.9 mg/ml | 0.01-0.06 mg/ml |
| Hyaluronic acid | Excipient | 10 mg/ml | 2.8-4.0 mg/ml |
| Dextrose | Excipient | 50 mg/ml | 17.6-33.55 mg/ml |

Baseline Efficacy and Safety Evaluation

Before treatment, the clinical status of each patient was assessed by medical history, physical examination, complete blood count, serum CEA and chemistry panel. A baseline CT scan of chest, abdomen and pelvis was performed within 4 weeks prior to the first cycle of treatment. During treatment, patients were assessed with a physical examination, complete blood count, blood chemistry and toxicity grading on day 1 of every cycle. Following every 2 cycles, radiological imaging was repeated to determine disease status. RECIST criteria were used for assessment of response using previously published definitions of complete response (CR), partial response (PR), stable disease (SD) and progressive disease (PD) (Therasse et al. *J Natl Cancer Inst* 92:205-216., 2000)

Patient Characteristics

Twelve patients were enrolled into the study between July 2003 and September 2004. All patients were evaluated for response and toxicity. Nine males and 3 females were enrolled with a median age of 63 years (range 39 to 73). All patients had received prior 5-FU chemotherapy and 2 had also received oxaliplatin. Patient characteristics at study entry are shown in Table 15. The median number of cycles received was 5 (range 1-6).

TABLE 15

| Patient characteristics | |
|---|---|
| Patients | 12 |
| Median age (Range) | 63 (39-73) |
| Male/Female | 9/3 |
| ECOG | |
| 0 | 9 |
| 1 | 3 |
| Previous chemotherapy | |
| 5-FU | 9 |
| 5FU and oxaliplatin | 3 |
| Sites of disease (%) | |
| Liver | 9 (75) |
| Lymph nodes | 5 (42) |
| Lung | 2 (17) |
| Peritoneum | 1 (9) |

Toxicity

Grade III liver dysfunction, considered to be due to progressive disease, was observed in the first patient enrolled for administration of HYCAMP having a hyaluronic acid dose of 1000 mg/m² and an irinotecan dose of 300 mg/m² after the first cycle of treatment. A further 4 patients were treated at this level with no dose limiting toxicity, and they received HYCAMP having hyaluronic acid at 1000 mg/m² and irinotecan at 350 mg/m² for the second and subsequent cycles. Seven patients commenced treatment with the irinotecan dose of HyCAMP at 350 mg/m². Dose reduction was required in 2 of these 7 patients, due to grade III diarrhea and grade IV neutropenia and grade III lethargy (the last two events were in the same patient).

Treatment related grade III and IV toxicity is summarized in Table 16. The single episode of grade III diarrhea occurred during cycle 5 in a patient who had not had significant diarrhea prior to this. Other grade III/grade IV toxicity that is not included in the table was liver dysfunction considered related to progressive disease and hyperglycemia considered related to steroid premedication. There were a total of 8 episodes of NCICTC grade III/IV toxicities. Of these, 3 were felt to be study drug related. They were 1 grade III diarrhea, 1 grade IV neutropenia and 1 grade III neutropenia. There were no toxic deaths associated with treatment.

TABLE 16

| Grade III and IV toxicity Summary | |
|---|---|
| Toxicity | Number of patients (%) |
| Neutropenia | 2 (17) |
| Diarrhea | 1 (9) |
| Anemia | 0 |
| Thrombocytopenia | 0 |
| Nausea/vomiting | 0 |
| Hepatic | 1 (9) |
| Hyperglycemia | 1 (9) |
| Lethargy | 1 (9) |

Tumor Response

All 12 patients were evaluated for their response to the therapeutic composition. Response data are summarized in Table 17. Partial responses were seen in two patients, for an overall response rate of 17%. Five patients had stable disease and 5 progressive disease as their best response.

TABLE 17

| Tumor response to HyCAMP ™ | |
|---|---|
| Response | Number of patients (%) |
| Complete response | 0 |
| Partial response | 2 (17) |
| Stable disease | 5 (42) |
| Progressive disease | 5 (42) |

While irinotecan has an important role in the management of patients with metastatic colorectal cancer, unpredictable and potentially life threatening toxicity remains a major concern. (Rothenberg et al. *J Clin Oncol* 19:3801-7, 2001, Van Cutsem et al. *Br J Cancer* 92:1055-62, 2005, Ratain M J. *J Clin Oncol* 20:7-8, 2002). Improving the safety profile of irinotecan would likely lead to wider use of this important agent and potentially improved treatment outcomes, with several studies suggesting a dose response relationship. (Van Cutsem et al. 2005 supra, Merrouche et al. *J Clin Oncol* 15:1080-6, 1997, Ychou Ychou et al. *Cancer Chemother Pharmacol* 50:383-91, 2002, Rothenberg et al. *Cancer* 85:786-95, 1999). Here the results of a phase I trial exploring the safety of adding hyaluronic acid to a standard regimen of irinotecan in patients with metastatic colorectal cancer previously treated with 5-FU was evaluated.

Apart from the first patient enrolled, who had progressive disease after the first cycle of treatment, all subsequent patients received at least one cycle of HA plus irinotecan at the standard dose of 350 mg/m$^2$ every 3 weeks. Overall treatment was well tolerated, with only two patients requiring a dose reduction due to toxicity and, compared to historical controls, the rates of grade III and IV toxicity were low. Of note none of the 12 patients on this phase I study required a dose reduction for treatment related diarrhea after receiving the first two cycles. The only case of grade III diarrhea was observed in a patient, who having previously tolerated treatment well, had a short-lived episode of diarrhea during cycle five of treatment raising the possibility that this was not treatment related. The rate of severe neutropenia in this study was also low at 17%, and no episodes of grade III and IV nausea and/or vomiting were observed. Another way of expressing toxicity is to look at the number of patients requiring a dose reduction by the second cycle of treatment, which in this study was only 9% compared to 41% in a recent study.[14]

In this mixed patient population, including three patients who had previously received oxaliplatin chemotherapy, responses were seen in 2 of the 12 patients (17%), and stable disease in a further 5 patients (42%), suggesting that combining irinotecan with HA does not compromise treatment efficacy. However, as with the rates of toxicity much larger randomized studies could be done to more clearly define the benefit of adding HA to irinotecan.

REFERENCES

Andreutti D, Geinoz A, Gabbiani G. Effect of hyaluronic acid on migration, proliferation and alpha-smooth muscle actin expression by cultured rat and human fibroblasts. Submicrosc Cytol Pathol. 1999 April; 31(2):173-7.

Culty, M., Shizari, M., Erik, W., Thompson. and Underhill, C. B. (1994). Binding and degradation of hyaluronan by human breast cancer cell lines expressing different forms of CD44: Correlation with invasive potential. *Journal of Cellular Physiology* 160: pp 275-286.

Culty, M., Nguyen, H A, and Underhill, C B. (1992). The hyaluronan receptor (CD44) participates in the uptake and degradation of hyaluronan. *J Cell Biol* 116 (4): pp 1055-1062.

Dube B, Luke H J, Aumailley M, Prehm P. Hyaluronan reduces migration and proliferation in CHO cells. Bochim Biophys Acta. 2001 Apr. 23; 1538(2-3):283-9.

Ferns G A, Konneh M, Rutherford C, Woolaghan E, Anggard E E. Hyaluronan (HYAL-BV 5200) inhibits neo-intimal macrophage influx after balloon-catheter induced injury in the cholesterol-fed rabbit. Atherosclerosis. 1995 Apr. 24; 114(2):157-64.

Lang F., Ritter M., Volkl H and Haussinger D (1993). The biological Significance of cell volume Ren Physiol Biochem. 16: pp. 48-65.

Tamoto K, Nochi H, Tada M, Shimada S, Mori Y, Kataoka S, Suzuki Y, Nakamura T. High-molecular-weight hyaluronic acids inhibit chemotaxis and phagocytosis but not lysosomal enzyme release induced by receptor-mediated stimulations in guinea pig phagocytes. Mcrobiol Immunol. 1994; 38(1):73-80.

Wang, C., Zhang, S. and Turley, E A. (1996). The role of hyaluronan and hyaluronan receptors in breast cancer cell invasion, motility and proliferation. In: Fourth International Workshop on Hyaluronan in Drug Delivery. (Editor: Willoughby, D. A) Roy. Soc. Med. Press. pp 37-53.

Wang, C., Tammi, M., Guo, H. and Tammi, R. (1997). Hyaluronan distribution in the normal epithelium of esophagus, stomach, and colon and their cancers. *American Journal of Pathology*. 148 (6): pp 1861-1869.

INCORPORATION BY REFERENCE

The contents of all references, patents, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of treating a solid tumor cancer comprising the step of intravenously administering to a subject, with said solid tumor cancer in need thereof, a therapeutically effective amount of a composition comprising a cancer chemotherapeutic and a hyaluronan, wherein the hyaluronan has a size expressed as a molecular weight of 800,000 to 1,432,000 Daltons or an intrinsic viscosity of 10.0 dl/gm to 14.5 dl/gm, and wherein the cancer is selected from the group consisting of cancers of the lung, pancreas, and colorectal.

2. The method according to claim 1, wherein the subject is a mammal.

3. The method according to claim 2, wherein the mammal is selected from the group consisting of bovine, canine, equine, feline, porcine and human.

4. The method according to claim 1, wherein the cancer chemotherapeutic agent is selected from the group consisting of carmustine (BCNU), chlorambucil (Leukeran), cisplatin (Platinol), Cytarabine, doxorubicin (Adriamycin), fluorouracil (5-FU), methotrexate (mexate), CPT 11 (irinotecan), etoposide, pliamycin (Mithracin) and taxanes.

5. The method according to claim 4, wherein the cancer chemotherapeutic agent is fluorouracil (5-FU).

6. A method of treating a patient with a solid tumor cancer comprising the administration intravenously of a composition comprising a therapeutically effective amount of irinotecan (CPT 11) together with hyaluronan, wherein the hyaluronan has a size expressed as a molecular weight of 800,000 to 1,432,000 Daltons or an intrinsic viscosity of 10.0 dl/gm to 14.5 dl/gm, to a patient with said solid tumor cancer in need of such treatment, and wherein the cancer is selected from the group consisting of cancers of the lung, pancreas, and colorectal.

7. The method of claim 6, wherein the molecular weight of the hyaluronan is about 800,000 to 1,000,000 Daltons.

8. The method of claim 7, wherein the molecular weight of the hyaluronan is about 825,000 to 850,000 Daltons.

9. The method of claim 6, wherein the therapeutically effective amount of irinotecan (CPT 11) is about 100 to 500 mg/m$^2$.

10. The method of claim 9, wherein the therapeutically effective amount of irinotecan (CPT 11) is about 100 to 150 mg/m$^2$ administered every five to ten days for two or more cycles.

11. The method of claim 9, wherein the therapeutically effective amount of irinotecan (CPT11) is about 300 to 350 mg/m$^2$ administered every 15 to 30 days for two or more cycles.

12. The method according to claim 6, wherein the cancer is lung cancer.

13. The method of claim 6, wherein the cancer is pancreatic cancer.

14. The method of claim 1, wherein said cancer is metastatic.

15. The method according to claim 1, wherein said cancer is CD44 receptor positive.

16. The method according to claim 15, wherein the cancer is cancers of the lung.

17. The method according to claim 6, wherein said cancer is CD44 receptor positive.

18. The method according to claim 1, wherein the hyaluronan has a size expressed as an intrinsic viscosity of 10.0 dl/gm to 14.5 dl/gm.

19. The method according to claim 6, wherein the hyaluronan has a size expressed as an intrinsic viscosity of 10.0 dl/gm to 14.5 dl/gm.

20. The method of claim 6, wherein said hyaluronan is administered at a dose of about 750 to 1500 mg/m$^2$.

21. The method of claim 6, where said hyaluronan is administered at a dose of about 900 to 1100 mg/m$^2$.

22. The method of claim 6, wherein the dose of irinotecan is from about 125 mg/m$^2$ to about 350 mg/m$^2$.

23. The method of claim 6, wherein the dose of irinotecan is from about 100 mg/m$^2$ to about 200 mg/m2.

* * * * *